United States Patent
Li et al.

(10) Patent No.: US 11,807,663 B2
(45) Date of Patent: Nov. 7, 2023

(54) FULLY HUMANIZED ANTI-B CELL MATURATION ANTIGEN (BCMA) SINGLE-CHAIN ANTIBODY AND USE THEREOF

(71) Applicant: INNOVENT BIOLOGICS (SUZHOU) CO., LTD., Jiangsu (CN)

(72) Inventors: Zhiyuan Li, Jiangsu (CN); Tianhang Zhai, Jiangsu (CN); Shuaixiang Zhou, Jiangsu (CN); Dechao Yu, Jiangsu (CN)

(73) Assignee: INNOVENT BIOLOGICS (SUZHOU) CO., LTD., Suzhou (CN)

( * ) Notice: Subject to any disclaimer, the term of this patent is extended or adjusted under 35 U.S.C. 154(b) by 489 days.

(21) Appl. No.: 16/759,956

(22) PCT Filed: Feb. 1, 2019

(86) PCT No.: PCT/CN2019/074419
§ 371 (c)(1),
(2) Date: Apr. 28, 2020

(87) PCT Pub. No.: WO2019/149269
PCT Pub. Date: Aug. 8, 2019

(65) Prior Publication Data
US 2020/0339699 A1   Oct. 29, 2020

(30) Foreign Application Priority Data
Feb. 1, 2018 (CN) .......................... 201810100549.6

(51) Int. Cl.
*C07K 16/28* (2006.01)
*G01N 33/574* (2006.01)

(52) U.S. Cl.
CPC ... *C07K 16/2878* (2013.01); *G01N 33/57492* (2013.01); *C07K 2317/24* (2013.01); *C07K 2317/41* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,816,567 A | 3/1989 | Cabilly et al. |
| 5,091,513 A | 2/1992 | Huston et al. |
| 5,132,405 A | 7/1992 | Huston et al. |
| 5,208,020 A | 5/1993 | Chari et al. |
| 5,336,603 A | 8/1994 | Capon et al. |
| 5,500,362 A | 3/1996 | Robinson et al. |
| 5,622,929 A | 4/1997 | Willner et al. |
| 5,821,337 A | 10/1998 | Carter et al. |
| 5,959,177 A | 9/1999 | Hein et al. |
| 6,040,498 A | 3/2000 | Stomp et al. |
| 6,171,586 B1 | 1/2001 | Lam et al. |
| 6,194,551 B1 | 2/2001 | Dusogie et al. |
| 6,267,958 B1 | 7/2001 | Andya et al. |
| 6,417,429 B1 | 7/2002 | Hein et al. |
| 6,420,548 B1 | 7/2002 | Vézina et al. |
| 6,602,684 B1 | 8/2003 | Umaña et al. |
| 7,125,978 B1 | 10/2006 | Vézina et al. |
| 9,845,464 B2 | 12/2017 | Zha et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0123546 A1 | 6/2005 | Umana et al. |
| 2005/0196754 A1 | 9/2005 | Drmanac et al. |
| 2007/0274985 A1 | 11/2007 | Dubel et al. |
| 2011/0076752 A1 | 3/2011 | Wu et al. |
| 2016/0297885 A1 | 10/2016 | Kuo et al. |
| 2017/0226216 A1 | 8/2017 | Morgan et al. |

FOREIGN PATENT DOCUMENTS

| | | |
|---|---|---|
| CN | 105837693 A | 8/2016 |
| CN | 106279418 A | 1/2017 |
| CN | 106661109 A | 5/2017 |
| EP | 0367166 A1 | 5/1990 |
| EP | 0404097 B1 | 9/1996 |
| EP | 1176195 A1 | 1/2002 |

(Continued)

OTHER PUBLICATIONS

Rudikoff et al., Proc Natl Acad Sci USA 79: 1979-1983 (1982). (Year: 1982).*
Colman, Research in Immunology 145: 33-36, (1994). (Year: 1994).*
Kussie et al., J. Immunol. 152: 146-152 (1994). (Year: 1994).*
Chen et al., EMBO J., 14: 2784-2794, (1995). (Year: 1995).*
D'Angelo et al., Many Routes to an Antibody Heavy-Chain CDR3: Necessary, Yet Insufficient, for Specific Binding (Frontiers in Immunology vol. 9, Article 395 Mar. 2018; doi:10.3389/fimmu.2018.00395. (Year: 2018).*
Piche-Nicholas et al., Changes in complemetarity-determining regions significantly alter IgG binding to the neonatal Fc receptor (FcRN) and pharmacokinetics; MABS 2018, vol. 10, No. 1, 81-94, doi.org/10.1080/19420862.2017.1389355. (Year: 2018).*
Cho et al., Frontiers in Immunology 9:1821, 2018; 1028; doi.10.3389/immu.201801821 (Year: 2018).*

(Continued)

*Primary Examiner* — Zachary S Skelding
(74) *Attorney, Agent, or Firm* — Leason Ellis LLP

(57) ABSTRACT

The invention relates to a novel antibody and an antibody fragment thereof specifically binding to a B-cell maturation antigen (BCMA), and particularly relates to a fully humanized single-chain variable fragment (scFv). The invention further relates to a nucleic acid encoding the antibody, a vector, and a host cell expressing the nucleic acid. Furthermore, the invention also relates to a composition containing the antibody described herein, and use thereof in treatment and diagnosis.

19 Claims, 8 Drawing Sheets
Specification includes a Sequence Listing.

(56) References Cited

FOREIGN PATENT DOCUMENTS

| | | |
|---|---|---|
| EP | 3023437 A1 | 5/2016 |
| JP | 2015-535002 A | 12/2015 |
| JP | 2016-500256 A | 1/2016 |
| JP | 2017-515470 A | 6/2017 |
| JP | 2018-500014 A | 1/2018 |
| TW | 2017/06311 A | 2/2017 |
| WO | 1997/030087 A1 | 8/1997 |
| WO | 1998/058964 A1 | 12/1998 |
| WO | 1999/022764 A1 | 5/1999 |
| WO | 1999/051642 A1 | 10/1999 |
| WO | 2000/061739 A1 | 10/2000 |
| WO | 2001/029246 A1 | 4/2001 |
| WO | 2002/31140 A1 | 10/2001 |
| WO | 2003/011878 A2 | 2/2003 |
| WO | 2003/084570 A1 | 4/2003 |
| WO | 2003/085119 A1 | 4/2003 |
| WO | 2003/085107 A1 | 10/2003 |
| WO | 2004/056312 A2 | 7/2004 |
| WO | 2005/035586 A1 | 4/2005 |
| WO | 2005/035778 A1 | 4/2005 |
| WO | 2005/053742 A1 | 6/2005 |
| WO | 2005/100402 A1 | 10/2005 |
| WO | 2006/029879 A2 | 3/2006 |
| WO | 2006/044908 A2 | 4/2006 |
| WO | 2008/077546 A1 | 7/2008 |
| WO | 2009/036379 A2 | 3/2009 |
| WO | 2010/104949 A2 | 9/2010 |
| WO | 2010/105256 A1 | 9/2010 |
| WO | 2012/009568 A2 | 1/2012 |
| WO | 2012/138475 A1 | 10/2012 |
| WO | 2012/163805 A1 | 12/2012 |
| WO | 2014/087010 A1 | 6/2014 |
| WO | 2014/089335 A2 | 6/2014 |
| WO | 2015/166073 A1 | 11/2015 |
| WO | 2016/014789 A2 | 1/2016 |
| WO | 2016/090327 A2 | 6/2016 |
| WO | 2017/021450 A1 | 2/2017 |
| WO | 2017/083511 A1 | 5/2017 |
| WO | 2017/211900 A1 | 12/2017 |

OTHER PUBLICATIONS

Lee et al. Nature Reviews / Drug Discovery vol. 20: 179-199 Mar. 2021. (Year: 2021).*
Wuertzer. C.A. et al. "Accession No. ABX83198.1"; GenBank, 2016.
Lee. C.V. et al. "Synthetic Anti-BR3 Antibodies that Mimic BAFF Binding and Target Both Human and Murine B Cells" Blood, 2006, vol. 108. No. 9: 3103-3111.
International Search Report of corresponding International Application PCT/CN2019/074419, dated Jun. 13, 2019 and English translation.
Written Opinion of the International Searching Authority of corresponding International Application PCT/CN2019/074419, dated Jun. 13, 2019, with English translation.
Mather, J. P., Establishment and characterization of two distinct mouse testicular epithelial cell lines, Biol. Reprod. 23 (1980) 243-252.
Mather, J. P. et al., Culture of testicular cells in hormone-supplemented serum-free medium, Annals N.Y. Acad. Sci. 383 (1982) 44-68.
Urlaub, G. et al., Isolation of Chinese hamster cell mutants deficient in dihydrofolate reductase activity, Proc. Natl. Acad. Sci. USA 77 (1980) 4216-4220.
Chari et al., Immunoconjugates containing novel maytansinoids: promising anticancer drugs, Cancer Research, 52 (1992) 127-131.
Mattila et al., Fidelity of DNA synthesis by the Thermococcus litoralis DNA polymerase—an extremely heat stable enzyme with proofreading activity, Nucleic Acids Res. 19:4967, 1991.
Rickert et al., Signaling by the tumor necrosis factor receptor superfamily in B-cell biology and disease, Immunological Reviews, 2011, vol. 244: 115-133.
Hahne et al., April, a new ligand of the tumor necrosis factor family, stimulates tumor cell growth, T. Exp. Med., (1998) 188: 1185-90.
Tai et al., Novel anti-B-cell maturation antigen antibody-drug conjugate (GSK2857916) selectively induces killing of multiple myeloma, BLOOD, 2014, vol. 123, Issue 20, pp. 3128-3138.
Vincent et al., The BAFF/APRIL system in SLE pathogenesis, Nature Reviews Rheumatology, 2014, vol. 10: 365-373.
Chao et al., Isolating and engineering human antibodies using yeast surface display, Nature Protocols, 2006, vol. 1: 755-768.
Xu et al., Addressing polyspecificity of antibodies selected from an in vitro yeast presentation system: a FACS-based, high-throughput selection and analytical tool, Protein Engineering, Design & Selection, 2013, vol. 26, Issue 10: 663-670.
Estep, et al., High throughput solution Based measurement of antibody-antigen affinity and epitope binning. MAbs, 2013, 5 (2): p. 270-8.
Boder and Wittrup, Yeast surface display for screening conbinatorial polypeptide libraries, 1997, Nat. Biotechnol., 15, 553-557.
Blasie et al., Construction and diversification of yeast cell surface displayed libraries by yeast mating: application to the affinity maturation of Fab antibody fragments, 2004, Gene, 342, 211-218.
Sazinsky et al., Aglycosylated immunoglobulin G1 variants productively engage activating Fc receptors, 2008, Proc. Natl. Acad. Sci. USA, 105, 20167-20172.
Tasumi et al., High-affinity lamprey VLRA and VLRB monoclonal antibodies, 2009, Proc. Natl. Acad. Sci. USA, 106, 12891-12896.
Kuroda and Ueda, Cell surface engineering of yeast for applications in white biotechnology, 2011, Biotechnol. Lett., 33, 1-9.
Rakestraw et al., Secretion-and-capture cell-surface display for selection of target-binding proteins, 2011, PEDS, 24, 525-530.
Dernick, G. et al., Multidimensional profiling of plasma lipoproteins by size exclusion chromatography followed by reverse-phase protein arrays, J. Lipid Res., 52(2011) 2323-2331.
Clackson, et al., Making antibody fragments using phage display, Nature 352 (1991) 624-628.
Shen et al., Engineering Peptide Linkers for scFv Immunosensors, Anal. Chem. 80 (6):1910-1917 (2008).
Liu et al., Design of polydactyl zinc-finger proteins for unique addressing within complex genomes, PNAS, 5525-5530 (1997).
Kim et al., Hybrid restriction enzymes: Zinc finger fusions to Fok I cleavage domain, PNAS, 93,1156-1160 (1996).
Chaudhary et al., A rapid method of cloning functional variable-region antibody genes in *Escherichia coli* as single-chain immunotoxins, 1990, Proc. Natl. Acad. Sci. U.S.A., 87:1066-1070.
Bird et al., Single-Chain Antigen-Binding Proteins, 1988, Science, 242: 423-426.
Desjaais & Berg, Use of a zinc-finger consensus sequence framework and specificity rules to design specific DNA binding proteins, PNAS, 90:2256-2260 (1993).
Desjaais & Berg, Length-encoded multiplex binding site determination: Application to zinc finger proteins, PNAS 91:11099-11103 (1994).
Huston et al., Protein engineering of antibody binding sites: Recovery of specific activity in an anti-digoxin single-chain Fv analogue produced in *Escherichia coli*, Proc. Nat. Acad. Sci. USA, 85: 5879-5883, 1988.
Hudson et al., Engineered antibodies, Mat. Med. 9:129-134 (2003).
Hollinger et al., "Diabodies": Small bivalent and bispecific antibody fragments, PNAS, 90:6444-6448 (1993).
Flatman et al., Process analytics for purification of monoclonal antibodies, J. Chrom. B 848 (2007) 79-87.
Chothia and Lesk, Canonical structures for the hypervariable regions of immunoglobulins, J. mol. biol. 196:901-917 (1987).
Idusogie et al., Mapping of the C1q binding site on rituxan, a chimeric antibody with a human IgG1 Fc, J. Immunol. 164 (2000) 4178-4184.
Okazaki et al., Fucose Depletion from Human IgG1 Oligosaccharide Enhances Binding Enthalpy and Association Rate Between IgG1 and FcgRIIIa, J. Mol. Biol., 336 (2004) 1239-1249.
Yamane ohnuki et al., Establishment of FUT8 Knockout Chinese Hamster Ovary Cells: An Ideal Host Cell Line for Producing

(56) References Cited

OTHER PUBLICATIONS

Completely Defucosylated Antibodies With Enhanced Antibody-Dependent Cellular Cytotoxicity, Biotech. Bioeng. 87:614 (2004) 614-622.

Ripka et al., Two Chinese hamster ovary glycosylation mutants affected in the conversion of GDP-mannose to GDP-fucose, Arch. Biochem. Biophys. 249 (1986) : 533-545.

Kanda, et al., Comparison of Cell Lines for Stable Production of Fucose-Negative Antibodies With Enhanced ADCC, Biotechnol. Bioeng. 94 (2006) 680-688.

Hellstrom, et al., Antitumor effects of L6, an IgG2a antibody that reacts with most human carcinomas, Proc. Nat'l Acad. Sci. USA 83 (1986) 7059-7063.

Hellstrom et al., Strong antitumor activities of IgG3 antibodies to a human melanoma-associated ganglioside, Proc. Nat'l Acad. Sci. USA, 82 (1985) 1499-1502.

Bruggemann, et al., Comparison of the effector functions of human immunoglobulins using a matched set of chimeric antibodies, J. Exp. Med. 166 (1987) 1351-1361.

Clynes et al., Fc receptors are required in passive and active immunity to melanoma, Proc. Nat'l Acad. Sci. USA, 95 (1998) 652-656.

Gazzano-Santoro et al., A non-radioactive complement-dependent cytotoxicity assay for anti-CD20 monoclonal antibody, J. Immunol. Methods 202 (1997) 163-171.

Cragg et al., Complement-mediated lysis by anti-CD20 mAb correlates with segregation into lipid rafts, Blood 101 (2003) 1045-1052.

Cragg, M.S. and M.J. Glennie, Antibody specificity controls in vivo effector mechanisms of anti-CD20 reagents, Blood 103 (2004) 2738-2743.

Brown et al., Chemical synthesis and cloning of a tyrosine tRNA gene, Meth. Enzymol. 68:109-51, 1979.

Narang et al., Improved phosphotriester Method for the Synthesis of Gene Fragments, 1979, Meth. Enzymol. 68:90.

Beaucage et al., Deoxynucleoside phosphoramidites—A new class of key intermediates for deoxypolynucleotide synthesis, Tetra. Lett., 22:1859-1862, 1981.

Eckert et al., DNA polymerase fidelity and the polymerase chain reaction, PCR Methods and Applications 1:17-24, 1991.

Harrington et al., Formation of de novo centromeres and construction of first-generation human artificial microchromosomes, Nat. Genet. 15:345-355, 1997.

Smith, Annu. Viral vectors in gene therapy, Rev. Microbiol. 49:807-838, 1995.

Rosenfeld et al., In vivo transfer of the human cystic fibrosis transmembrane conductance regulator gene to the airway epithelium, Cell 68:143-155, 1992.

Bitter et al., Expression and secretion vectors for yeast, Meth. Enzymol., 153:516-544, 1987.

Gerngross, Advances in the production of human therapeutic proteins in yeasts and filamentous fungi, Nat. Biotech. 22 (2004) 1409-1414.

Li, et al., Optimization of humanized IgGs in glycoengineered Pichia pastoris, Nat. Biotech (2006) 24:210-215.

Graham, et al., Characteristics of a human cell line transformed by DNA from human adenovirus type 5, J. Gen Virol.36 (1977) 59-72.

\* cited by examiner

| Antibody | HCDR1 | SEQ ID NO | HCDR2 | SEQ ID NO | HCDR3 | SEQ ID NO | LCDR1 | SEQ ID NO | LCDR2 | SEQ ID NO | LCDR3 | SEQ ID NO |
|---|---|---|---|---|---|---|---|---|---|---|---|---|
| Kabat numbering position | H27-35B | | H50-65 | | H93-102 | | L24-34 | | L50-56 | | L89-97 | |
| ADI-34848 | FTFDDYAMH | 1 | GISWSSGSIGYADSVKG | 2 | AKDSPRRDSFGSIAFDI | 3 | RSSQSLLHSNGYNYLD | 28 | LGSNRAS | 29 | MQAKRLPIT | 30 |
| ADI-34849 | FTFDDYAMH | 1 | GISWSSGSIGYADSVKG | 2 | AKDSPRRDSFGSIAFDI | 3 | RASQSVSSYLA | 32 | DASKRAT | 35 | QQASALPLT | 38 |
| ADI-34850 | FTFDDYAMH | 1 | GISWSSGSIGYADSVKG | 2 | AKDSPRRDSFGSIAFDI | 3 | RASQSVGSNLA | 33 | GASTRAT | 36 | QQSVNLPIT | 39 |
| Consensus sequence | FTFDDYAMH | 1 | GISWSSGSIGYADSVKG | 2 | AKDSPRRDSFGSIAFDI | 3 | RASQSVXXXLA | 34 | XASXRAT | 37 | QQXXXXLPXT | 40 |
| ADI-34854 | FTFSSYGMH | 7 | VISYEGSNKYYADSVKG | 8 | ARDTSSYGDASYGMDV | 9 | RASQSVSSYLA | 32 | DASNRAT | 44 | QQYSHWPPT | 45 |
| ADI-34846 | GTFSNYAIS | 11 | GIIPIFGTANYAQKFQG | 12 | ARGSGYYSSWLFDI | 13 | KSSQSVLYSSNNKNYLA | 47 | WASTRES | 48 | QQYSDLT | 49 |
| ADI-34857 | GTFSNYAIS | 11 | GIIPIFGTANYAQKFQG | 12 | ARGRGYYSSWLFDI | 14 | QASQDINYLN | 51 | DASNLET | 54 | QQAFDLT | 55 |
| Consensus sequence | GTFSNYAIS | 11 | GIIPIFGTANYAQKFQG | 12 | ARGXGYYSSWLFDI | 15 | | | | | | |
| ADI-34832 | FSLSTSGVGVG | 20 | LIYWNDEKRYSPSLKS | 21 | ARDPGEQLQVFDY | 22 | RASQGISSWLA | 61 | AASSLQS | 62 | QQTLSLPLT | 63 |
| ADI-34859 | GSISSSSYYWG | 24 | SISYSGSTYYNPSLKS | 25 | ARDRGDTILDV | 26 | RASQSISSYLN | 52 | AASSLQS | 62 | QQKASAPIT | 56 |
| ADI-34860 | GSISSSSYYWG | 24 | SISYSGSTYYNPSLKS | 25 | ARDRGDTILDV | 26 | RASQSISSYLN | 65 | AASSLQS | 62 | QQKYDLLT | 68 |
| ADI-34861 | GSISSSSYYWG | 24 | SISYSGSTYYNPSLKS | 25 | ARDRGDTILDV | 26 | RASQSISRYLN | 66 | AASSLQS | 62 | QQKYFDI | 69 |
| Consensus sequence | GSISSSSYYWG | 24 | SISYSGSTYYNPSLKS | 25 | ARDRGDTILDV | 26 | RASQSISXYLN | 67 | AASSLQS | 62 | QQKYXXT | 70 |

FIG. 4

| Antibody | VH | | SEQ ID NO |
|---|---|---|---|
| ADI-34848 | EVQLLESGGGLVQPGGSLRLSCAASGFTFDDYAMHWVRQAPGKGLEWVSGISWSSGSIGYADSVKGRFTISRDNAKNSLYLQMNSLRAEDTAVYYCAKDSPRR DSFGSIAFDIWGQGTMVTVSS | | 4 |
| ADI-34849 | EVQLVESGGGLVQPGRSLRLSCAASGFTFDDYAMHWVRQAPGKGLEWVSGISWSSGSIGYADSVKGRFTISRDNAKNSLYLQMNSLRAEDTAVYYCAKDSPRR DSFGSIAFDIWGQGTMVTVSS | | 5 |
| ADI-34850 | EVQLVESGGGLVQPGRSLRLSCAASGFTFDDYAMHWVRQAPGKGLEWVSGISWSSGSIGYADSVKGRFTISRDNAKNSLYLQMNSLRAEDTAVYYCAKDSPRR DSFGSIAFDIWGQGTMVTVSS | | 5 |
| Consensus sequence | EVQLXESGGGLVQPGXSLRLSCAASGFTFDDYAMHWVRQAPGKGLEWVSGISWSSGSIGYADSVKGRFTISRDNAKNSLYLQMNSLRAEDTAVYYCAKDSPRR DSFGSIAFDIWGQGTMVTVSS | | 6 |

| Antibody | VH | | SEQ ID NO |
|---|---|---|---|
| ADI-34854 | QVQLVESGGGVVQPGRSLRLSCAASGFTFSSYGMHWVRQAPGKGLEWVAVISYEGSNKYYADSVKGRFTISRDNSKNTLYLQMNSLRAEDTAVYYCARDTSSY GDASYGMDVWGQGTTVTVSS | | 10 |

| Antibody | VH | | SEQ ID NO |
|---|---|---|---|
| ADI-34846 | QVQLVQSGAEVKKPGSSVKVSCKASGGTFSNYAISWVRQAPGQGLEWMGGIIPIFGTANYAQKFQGRVTITADESTSTAYMELSSLKSEDTAVYYCARGSGYYSS WLFDIWGQGTMVTVSS | | 16 |
| ADI-34857 | QVQLVQSGAEVKKPGSSVKVSCKASGGTFSNYAISWVRQAPGQGLEWMGGIIPIFGTANYAQKFQGRVTITADESTSTAYMELSSLRSEDTAVYYCARGRGYYSS WLFDIWGQGTMVTVSS | | 17 |
| Consensus sequence | QVQLVQSGAEVKKPGSSVKVSCKASGGTFSNYAISWVRQAPGQGLEWMGGIIPIFGTANYAQKFQGRVTITADESTSTAYMELSSLXSEDTAVYYCARGXGYYS SWLFDIWGQGTMVTVSS | | 19 |

| Antibody | VH | | SEQ ID NO |
|---|---|---|---|
| ADI-34832 | QHTLKESGPTLVKPTQTLTLTCTFSGFSLSTSGVGVGWIRQPPGKALEWLALIYWNDEKRYSPSLKSRLTITKDTSKNQVVLTMTNMDPVDTAVYYCARDPGEQL QVFDYWGQGTLVTVSS | | 23 |

| Antibody | VH | | SEQ ID NO |
|---|---|---|---|
| ADI-34859 | QLQLQESGPGLVKPSETLSLTCTVSGGSISSSSYYWGWIRQPPGKGLEWIGSISYSGSTYYNPSLKSRVTISVDTSKNQFSLKLSSVTAADTAVYYCARDRGDTFLD VWGQGTMVTVSS | | 27 |
| ADI-34860 | QLQLQESGPGLVKPSETLSLTCTVSGGSISSSSYYWGWIRQPPGKGLEWIGSISYSGSTYYNPSLKSRVTISVDTSKNQFSLKLSSVTAADTAVYYCARDRGDTFLD VWGQGTMVTVSS | | 27 |
| ADI-34861 | QLQLQESGPGLVKPSETLSLTCTVSGGSISSSSYYWGWIRQPPGKGLEWIGSISYSGSTYYNPSLKSRVTISVDTSKNQFSLKLSSVTAADTAVYYCARDRGDTFLD VWGQGTMVTVSS | | 27 |

FIG. 5

| Antibody | VL | SEQ ID NO: |
|---|---|---|
| ADI-34848 | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQAKRLPITFGGGTKVEIK | 31 |
| ADI-34849 | EIVLTQSPATLSLSPGERATLSCRASQVSSYLAWYQQKPGQAPRLLIYDASKRATGIPARFSGSGSGTDFTLTISSLEPEDFAVYYCQQASALPLTFGGGTKVEIK | 41 |
| ADI-34850 | EIVMTQSPATLSVSPGERATLSCRASQSVGSNLAWYQQKPGQAPRLLIYGASTRATGIPARFSGSGSGTEFTLTISSLQSEDFAVYYCQQSVNLPITFGGGTKVEI K | 42 |
| Consensus sequence | EIVXTQSPATLSXXSPGERATLSCRASQSVXXXLAWYQQKPGQAPRLLIYXASXRATGIPARFSGSGSGTXFTLTISSLXXEDFAVYYCQQXXXXLPXTFGGGTKVE IK | 43 |
| Antibody | VL | SEQ ID NO: |
| ADI-34854 | EIVLTQSPATLSLSPGERATLSCRASQSVSSYLAWYQQKPGQAPRLLIYDASNRATGIPARFSGSGSGTDFTLTISSLEPEDFAVYYCQQYSHWPPITFGGGTKVEI K | 46 |
| Antibody | VL | SEQ ID NO: |
| ADI-34846 | DIVLTQSPDSLAVSLGERATINCKSSQSVLYSSNNKNYLAWYQQKPGQPPKLLIYWASTRESGVPDRFSGSGSGTDFTLTISSLQAEDVAVYYCQQYSDLLTFG GGTKVEIK | 50 |
| Antibody | VL | SEQ ID NO: |
| ADI-34857 | DIQMTQSPSSLSASVGDRVTITCQASQDITNYLNWYQQKPGKAPKLLIYDASNLETGVPSRFSGSGSGTDFTFTISSLQPEDIATYYCQQAFDLITFGGGTKVEIK | 58 |
| Antibody | VL | SEQ ID NO: |
| ADI-34832 | DIQMTQSPSSVSASVGDRVTITCRASQGISSWLAWYQQKPGKAPKLLIYAASSLQSGVPSRFSGSGSGTDFTLTISSLQPEDFATYYCQQILSLPITFGGGTKVEIK | 64 |
| Antibody | VL | SEQ ID NO: |
| ADI-34859 | DIQMTQSPSSLSASVGDRVTITCRASQSINSYLNWYQQKPGKAPKLLIYAASSLQSGVPSRFSGSGSGTDFTLTISSLQPEDFATYYCQQKASAPITFGGGTKVEIK | 59 |
| ADI-34860 | DIQMTQSPSSLSASVGDRVTITCRASQSISSYLNWYQQKPGKAPKLLIYAASSLQSGVPSRFSGSGSGTDFTLTISSLQPEDFATYYCQQKYDLLTFGGGTKVEIK | 71 |
| ADI-34861 | DIQMTQSPSSLSASVGDRVTITCRASQSISRYLNWYQQKPGKAPKLLIYAASSLQSGVPSRFSGSGSGTDFTLTISSLQPEDFATYYCQQKYFDITFGGGTKVEIK | 72 |
| Consensus sequence | DIQMTQSPSSLSASVGDRVTITCRASQSISXYLNWYQQKPGKAPKLLIYAASSLQSGVPSRFSGSGSGTDFTLTISSLQPEDFATYYCQQKYXXXXTFGGGTKVEIK | 73 |

FIG. 6

Human BCMA antigen sequence:

MLQMAGQCSQNEYFDSLLHACIPCQLRCSSNTPPLTCQRYCNASVTNSVKGTNAILWTCLGLSLIISLAVFVLMFLLRKINSEPLKDEFKNTGSGLLGMANIDLEKSRTGDEIILPRGLEYTVEECTCEDCIKSKPKVDSDHCFPLPAMEEGATILVTTKTNDYCKSLPAALSATEIEKSISAR (SEQ ID NO: 74)

Extracellular domain (ECD) of human BCMA

MLQMAGQCSQNEYFDSLLHACIPCQLRCSSNTPPLTCQRYCNASVTNSVKGT

FIG. 7

Linker

GSTSGSGKPGSGEGSTKG (SEQ ID NO: 93)

GGCAGCACCAGCGGCTCCGGCAAGCCTGGCTCTGGCGAGGGCAGCACAAAGGGA (SEQ ID NO: 94, used for scFv-Fc of the invention)

GGCAGCACCAGCGGCAGCGGCAAGCCCGGCTCCGGAGAGGGCAGCACCAAGGGC (SEQ ID NO: 97, used for reference scFv-Fc)

CD8 hinge region

TTTPAPRPPTPAPTIASQPLSLRPEACRPAAGGAVHTRGLDFACD (SEQ ID NO: 95)

ACCACCACCCCTGCCCCTAGACCTCCAACCCCAGCCCCAACAATGGCCAGCCAGCCTCTGTCTCTGCGGCCCGAAGCCTGTAGACCTGCT
GCCGGCGGAGCCGTGCACACCAGAGGCCTGGACTTCGCCTGCGAC (SEQ ID NO: 96, used for scFv-Fc of the invention)

ACCACAACACCTGCTCCAAGGCCCCCAACCCCCAGCCCCCGCTCCAACTATAGCCAGCCAACCATTGAGACCTCAGACCTGAAGCTTGCAGGCCCGC
AGCAGGAGGCCGTCCATACGCCGAGGCCTGGACTTCGCGTGTGAT (SEQ ID NO: 98, used for reference scFv-Fc)

Human IgG1 Fc sequence

DKTHTCPPCPAPELLGGPSVFLFPPKPKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPGK (SEQ ID NO: 132)

SEQUENCE LISTING

```
<160> NUMBER OF SEQ ID NOS: 135

<210> SEQ ID NO 1
<211> LENGTH: 9
<212> TYPE: PRT
<213> ORGANISM: artificial sequence
<220> FEATURE:
<223> OTHER INFORMATION: HCDR1

<400> SEQUENCE: 1

Phe Thr Phe Asp Asp Tyr Ala Met His
1               5

<210> SEQ ID NO 2
<211> LENGTH: 17
<212> TYPE: PRT
<213> ORGANISM: artificial sequence
<220> FEATURE:
<223> OTHER INFORMATION: HCDR2

<400> SEQUENCE: 2

Gly Ile Ser Trp Ser Ser Gly Ser Ile Gly Tyr Ala Asp Ser Val Lys
1               5                   10                  15

Gly

<210> SEQ ID NO 3
<211> LENGTH: 17
<212> TYPE: PRT
<213> ORGANISM: artificial sequence
<220> FEATURE:
<223> OTHER INFORMATION: HCDR3
```

```
<400> SEQUENCE: 3

Ala Lys Asp Ser Pro Arg Arg Asp Ser Phe Gly Ser Ile Ala Phe Asp
1               5                   10                  15

Ile

<210> SEQ ID NO 4
<211> LENGTH: 124
<212> TYPE: PRT
<213> ORGANISM: artificial sequence
<220> FEATURE:
<223> OTHER INFORMATION: VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ser Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Arg Arg Asp Ser Phe Gly Ser Ile Ala Phe Asp
            100                 105                 110

Ile Trp Gly Gln Gly Thr Met Val Thr Val Ser Ser
        115                 120

<210> SEQ ID NO 5
<211> LENGTH: 124
<212> TYPE: PRT
<213> ORGANISM: artificial sequence
<220> FEATURE:
<223> OTHER INFORMATION: VH

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ser Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Arg Arg Asp Ser Phe Gly Ser Ile Ala Phe Asp
            100                 105                 110

Ile Trp Gly Gln Gly Thr Met Val Thr Val Ser Ser
        115                 120

<210> SEQ ID NO 6
<211> LENGTH: 124
<212> TYPE: PRT
```

-continued

```
<213> ORGANISM: artificial sequence
<220> FEATURE:
<223> OTHER INFORMATION: consensus
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 6

Glu Val Gln Leu Xaa Glu Ser Gly Gly Gly Leu Val Gln Pro Gly Xaa
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ser Ser Gly Ser Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Arg Arg Ser Phe Gly Ser Ile Ala Phe Asp
            100                 105                 110

Ile Trp Gly Gln Gly Thr Met Val Thr Val Ser Ser
        115                 120

<210> SEQ ID NO 7
<211> LENGTH: 9
<212> TYPE: PRT
<213> ORGANISM: artificial sequence
<220> FEATURE:
<223> OTHER INFORMATION: HCDR1

<400> SEQUENCE: 7

Phe Thr Phe Ser Ser Tyr Gly Met His
1               5

<210> SEQ ID NO 8
<211> LENGTH: 17
<212> TYPE: PRT
<213> ORGANISM: artificial sequence
<220> FEATURE:
<223> OTHER INFORMATION: HCDR2

<400> SEQUENCE: 8

Val Ile Ser Tyr Glu Gly Ser Asn Lys Tyr Tyr Ala Asp Ser Val Lys
1               5                   10                  15

Gly

<210> SEQ ID NO 9
<211> LENGTH: 16
<212> TYPE: PRT
<213> ORGANISM: artificial sequence
<220> FEATURE:
<223> OTHER INFORMATION: HCDR3

<400> SEQUENCE: 9

Ala Arg Asp Thr Ser Ser Tyr Gly Asp Ala Ser Tyr Gly Met Asp Val
1               5                   10                  15
```

<210> SEQ ID NO 10
<211> LENGTH: 123
<212> TYPE: PRT
<213> ORGANISM: artificial sequence
<220> FEATURE:
<223> OTHER INFORMATION: VH

<400> SEQUENCE: 10

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Glu Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Ser Ser Tyr Gly Asp Ala Ser Tyr Gly Met Asp Val
            100                 105                 110

Trp Gly Gln Gly Thr Thr Val Thr Val Ser Ser
        115                 120

<210> SEQ ID NO 11
<211> LENGTH: 9
<212> TYPE: PRT
<213> ORGANISM: artificial sequence
<220> FEATURE:
<223> OTHER INFORMATION: HCDR1

<400> SEQUENCE: 11

Gly Thr Phe Ser Asn Tyr Ala Ile Ser
1               5

<210> SEQ ID NO 12
<211> LENGTH: 17
<212> TYPE: PRT
<213> ORGANISM: artificial sequence
<220> FEATURE:
<223> OTHER INFORMATION: HCDR2

<400> SEQUENCE: 12

Gly Ile Ile Pro Ile Phe Gly Thr Ala Asn Tyr Ala Gln Lys Phe Gln
1               5                   10                  15

Gly

<210> SEQ ID NO 13
<211> LENGTH: 14
<212> TYPE: PRT
<213> ORGANISM: artificial sequence
<220> FEATURE:
<223> OTHER INFORMATION: HCDR3

<400> SEQUENCE: 13

Ala Arg Gly Ser Gly Tyr Tyr Ser Ser Trp Leu Phe Asp Ile
1               5                   10

<210> SEQ ID NO 14
<211> LENGTH: 14
<212> TYPE: PRT

-continued

```
<213> ORGANISM: artificial sequence
<220> FEATURE:
<223> OTHER INFORMATION: HCDR3

<400> SEQUENCE: 14

Ala Arg Gly Arg Gly Tyr Tyr Ser Ser Trp Leu Phe Asp Ile
1               5                   10

<210> SEQ ID NO 15
<211> LENGTH: 14
<212> TYPE: PRT
<213> ORGANISM: artificial sequence
<220> FEATURE:
<223> OTHER INFORMATION: CONSENSUS
<220> FEATURE:
<221> NAME/KEY: misc_feature
<222> LOCATION: (4)..(4)
<223> OTHER INFORMATION: Xaa can be any naturally occurring amino acid

<400> SEQUENCE: 15

Ala Arg Gly Xaa Gly Tyr Tyr Ser Ser Trp Leu Phe Asp Ile
1               5                   10

<210> SEQ ID NO 16
<211> LENGTH: 121
<212> TYPE: PRT
<213> ORGANISM: artificial sequence
<220> FEATURE:
<223> OTHER INFORMATION: VH

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Lys Ser Glu Asp Thr Ala Val Tyr Tyr Cys
                85                  90                  95

Ala Arg Gly Ser Gly Tyr Tyr Ser Ser Trp Leu Phe Asp Ile Trp Gly
            100                 105                 110

Gln Gly Thr Met Val Thr Val Ser Ser
        115                 120

<210> SEQ ID NO 17
<211> LENGTH: 121
<212> TYPE: PRT
<213> ORGANISM: artificial sequence
<220> FEATURE:
<223> OTHER INFORMATION: VH

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45
```

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gly Tyr Tyr Ser Ser Trp Leu Phe Asp Ile Trp Gly
                100                 105                 110

Gln Gly Thr Met Val Thr Val Ser Ser
            115                 120

<210> SEQ ID NO 18

<400> SEQUENCE: 18

000

<210> SEQ ID NO 19
<211> LENGTH: 121
<212> TYPE: PRT
<213> ORGANISM: artificial sequence
<220> FEATURE:
<223> OTHER INFORMATION: CONSENSUS
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
65                  70                  75                  80

Met Glu Leu Ser Ser Leu Xaa Ser Glu Asp Thr Ala Val Tyr Tyr Cys
                85                  90                  95

Ala Arg Gly Xaa Gly Tyr Tyr Ser Ser Trp Leu Phe Asp Ile Trp Gly
                100                 105                 110

Gln Gly Thr Met Val Thr Val Ser Ser
            115                 120

<210> SEQ ID NO 20
<211> LENGTH: 11
<212> TYPE: PRT
<213> ORGANISM: artificial sequence
<220> FEATURE:
<223> OTHER INFORMATION: HCDR1

<400> SEQUENCE: 20

Phe Ser Leu Ser Thr Ser Gly Val Gly Val Gly
1               5                   10

<210> SEQ ID NO 21

```
<211> LENGTH: 16
<212> TYPE: PRT
<213> ORGANISM: artificial sequence
<220> FEATURE:
<223> OTHER INFORMATION: HCDR2

<400> SEQUENCE: 21

Leu Ile Tyr Trp Asn Asp Glu Lys Arg Tyr Ser Pro Ser Leu Lys Ser
1               5                   10                  15

<210> SEQ ID NO 22
<211> LENGTH: 13
<212> TYPE: PRT
<213> ORGANISM: artificial sequence
<220> FEATURE:
<223> OTHER INFORMATION: HCDR3

<400> SEQUENCE: 22

Ala Arg Asp Pro Gly Glu Gln Leu Gln Val Phe Asp Tyr
1               5                   10

<210> SEQ ID NO 23
<211> LENGTH: 121
<212> TYPE: PRT
<213> ORGANISM: artificial sequence
<220> FEATURE:
<223> OTHER INFORMATION: VH

<400> SEQUENCE: 23

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Glu Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Val Tyr Tyr
                85                  90                  95

Cys Ala Arg Asp Pro Gly Glu Gln Leu Gln Val Phe Asp Tyr Trp Gly
            100                 105                 110

Gln Gly Thr Leu Val Thr Val Ser Ser
        115                 120

<210> SEQ ID NO 24
<211> LENGTH: 11
<212> TYPE: PRT
<213> ORGANISM: artificial sequence
<220> FEATURE:
<223> OTHER INFORMATION: HCDR1

<400> SEQUENCE: 24

Gly Ser Ile Ser Ser Ser Ser Tyr Tyr Trp Gly
1               5                   10

<210> SEQ ID NO 25
<211> LENGTH: 16
<212> TYPE: PRT
<213> ORGANISM: artificial sequence
<220> FEATURE:
<223> OTHER INFORMATION: HCDR2
```

```
<400> SEQUENCE: 25

Ser Ile Ser Tyr Ser Gly Ser Thr Tyr Tyr Asn Pro Ser Leu Lys Ser
1               5                   10                  15

<210> SEQ ID NO 26
<211> LENGTH: 11
<212> TYPE: PRT
<213> ORGANISM: artificial sequence
<220> FEATURE:
<223> OTHER INFORMATION: HCDR3

<400> SEQUENCE: 26

Ala Arg Asp Arg Gly Asp Thr Ile Leu Asp Val
1               5                   10

<210> SEQ ID NO 27
<211> LENGTH: 119
<212> TYPE: PRT
<213> ORGANISM: artificial sequence
<220> FEATURE:
<223> OTHER INFORMATION: VH

<400> SEQUENCE: 27

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Gly Asp Thr Ile Leu Asp Val Trp Gly Gln Gly
            100                 105                 110

Thr Met Val Thr Val Ser Ser
        115

<210> SEQ ID NO 28
<211> LENGTH: 16
<212> TYPE: PRT
<213> ORGANISM: artificial sequence
<220> FEATURE:
<223> OTHER INFORMATION: LCDR1

<400> SEQUENCE: 28

Arg Ser Ser Gln Ser Leu Leu His Ser Asn Gly Tyr Asn Tyr Leu Asp
1               5                   10                  15

<210> SEQ ID NO 29
<211> LENGTH: 7
<212> TYPE: PRT
<213> ORGANISM: artificial sequence
<220> FEATURE:
<223> OTHER INFORMATION: LCDR2

<400> SEQUENCE: 29

Leu Gly Ser Asn Arg Ala Ser
1               5
```

<210> SEQ ID NO 30
<211> LENGTH: 9
<212> TYPE: PRT
<213> ORGANISM: artificial sequence
<220> FEATURE:
<223> OTHER INFORMATION: LCDR3

<400> SEQUENCE: 30

Met Gln Ala Lys Arg Leu Pro Ile Thr
1               5

<210> SEQ ID NO 31
<211> LENGTH: 112
<212> TYPE: PRT
<213> ORGANISM: artificial sequence
<220> FEATURE:
<223> OTHER INFORMATION: VL

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Lys Arg Leu Pro Ile Thr Phe Gly Gly Gly Thr Lys Val Glu Ile Lys
            100                 105                 110

<210> SEQ ID NO 32
<211> LENGTH: 11
<212> TYPE: PRT
<213> ORGANISM: artificial sequence
<220> FEATURE:
<223> OTHER INFORMATION: LCDR1

<400> SEQUENCE: 32

Arg Ala Ser Gln Ser Val Ser Ser Tyr Leu Ala
1               5                   10

<210> SEQ ID NO 33
<211> LENGTH: 11
<212> TYPE: PRT
<213> ORGANISM: artificial sequence
<220> FEATURE:
<223> OTHER INFORMATION: LCDR1

<400> SEQUENCE: 33

Arg Ala Ser Gln Ser Val Gly Ser Asn Leu Ala
1               5                   10

<210> SEQ ID NO 34
<211> LENGTH: 11
<212> TYPE: PRT
<213> ORGANISM: artificial sequence
<220> FEATURE:
<223> OTHER INFORMATION: CONSENSUS
<220> FEATURE:
<221> NAME/KEY: misc_feature
<222> LOCATION: (7)..(7)

```
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 34

Arg Ala Ser Gln Ser Val Xaa Ser Xaa Leu Ala
1               5                   10

<210> SEQ ID NO 35
<211> LENGTH: 7
<212> TYPE: PRT
<213> ORGANISM: artificial sequence
<220> FEATURE:
<223> OTHER INFORMATION: LCDR2

<400> SEQUENCE: 35

Asp Ala Ser Lys Arg Ala Thr
1               5

<210> SEQ ID NO 36
<211> LENGTH: 7
<212> TYPE: PRT
<213> ORGANISM: artificial sequence
<220> FEATURE:
<223> OTHER INFORMATION: LCDR2

<400> SEQUENCE: 36

Gly Ala Ser Thr Arg Ala Thr
1               5

<210> SEQ ID NO 37
<211> LENGTH: 7
<212> TYPE: PRT
<213> ORGANISM: artificial sequence
<220> FEATURE:
<223> OTHER INFORMATION: CONSENSUS
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 37

Xaa Ala Ser Xaa Arg Ala Thr
1               5

<210> SEQ ID NO 38
<211> LENGTH: 9
<212> TYPE: PRT
<213> ORGANISM: artificial sequence
<220> FEATURE:
<223> OTHER INFORMATION: LCDR3

<400> SEQUENCE: 38

Gln Gln Ala Ser Ala Leu Pro Leu Thr
1               5

<210> SEQ ID NO 39
<211> LENGTH: 9
<212> TYPE: PRT
<213> ORGANISM: artificial sequence
<220> FEATURE:
<223> OTHER INFORMATION: LCDR3
```

```
<400> SEQUENCE: 39

Gln Gln Ser Val Asn Leu Pro Ile Thr
1               5

<210> SEQ ID NO 40
<211> LENGTH: 9
<212> TYPE: PRT
<213> ORGANISM: artificial sequence
<220> FEATURE:
<223> OTHER INFORMATION: CONSENSUS
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 40

Gln Gln Xaa Xaa Xaa Leu Pro Xaa Thr
1               5

<210> SEQ ID NO 41
<211> LENGTH: 107
<212> TYPE: PRT
<213> ORGANISM: artificial sequence
<220> FEATURE:
<223> OTHER INFORMATION: VL

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Ser Ala Leu Pro Leu
                85                  90                  95

Thr Phe Gly Gly Gly Thr Lys Val Glu Ile Lys
            100                 105

<210> SEQ ID NO 42
<211> LENGTH: 107
<212> TYPE: PRT
<213> ORGANISM: artificial sequence
<220> FEATURE:
<223> OTHER INFORMATION: VL

<400> SEQUENCE: 42

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60
```

-continued

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Val Asn Leu Pro Ile
                85                  90                  95

Thr Phe Gly Gly Gly Thr Lys Val Glu Ile Lys
            100                 105

<210> SEQ ID NO 43
<211> LENGTH: 107
<212> TYPE: PRT
<213> ORGANISM: artificial sequence
<220> FEATURE:
<223> OTHER INFORMATION: CONSENSUS
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (91)..(93)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid

<400> SEQUENCE: 43

Glu Ile Val Xaa Thr Gln Ser Pro Ala Thr Leu Ser Xaa Ser Pro Gly
1               5                   10                  15

Glu Arg Ala Thr Leu Ser Cys Arg Ala Ser Gln Ser Val Xaa Ser Xaa
                20                  25                  30

Leu Ala Trp Tyr Gln Gln Lys Pro Gly Gln Ala Pro Arg Leu Leu Ile
            35                  40                  45

Tyr Xaa Ala Ser Xaa Arg Ala Thr Gly Ile Pro Ala Arg Phe Ser Gly
    50                  55                  60

Ser Gly Ser Gly Thr Xaa Phe Thr Leu Thr Ile Ser Ser Leu Xaa Xaa
65                  70                  75                  80

Glu Asp Phe Ala Val Tyr Tyr Cys Gln Gln Xaa Xaa Xaa Leu Pro Xaa
                85                  90                  95

Thr Phe Gly Gly Gly Thr Lys Val Glu Ile Lys
            100                 105

<210> SEQ ID NO 44
<211> LENGTH: 7
<212> TYPE: PRT
<213> ORGANISM: artificial sequence
<220> FEATURE:
<223> OTHER INFORMATION: LCDR2

<400> SEQUENCE: 44

Asp Ala Ser Asn Arg Ala Thr
1               5

<210> SEQ ID NO 45
<211> LENGTH: 9
<212> TYPE: PRT
<213> ORGANISM: artificial sequence
<220> FEATURE:
<223> OTHER INFORMATION: LCDR3

<400> SEQUENCE: 45

Gln Gln Tyr Ser His Trp Pro Pro Thr
1               5

<210> SEQ ID NO 46
<211> LENGTH: 107
<212> TYPE: PRT
<213> ORGANISM: artificial sequence
<220> FEATURE:
<223> OTHER INFORMATION: VL

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser His Trp Pro Pro
                85                  90                  95

Thr Phe Gly Gly Gly Thr Lys Val Glu Ile Lys
            100                 105

<210> SEQ ID NO 47
<211> LENGTH: 17
<212> TYPE: PRT
<213> ORGANISM: artificial sequence
<220> FEATURE:
<223> OTHER INFORMATION: LCDR1

<400> SEQUENCE: 47

Lys Ser Ser Gln Ser Val Leu Tyr Ser Ser Asn Asn Lys Asn Tyr Leu
1               5                   10                  15

Ala

<210> SEQ ID NO 48
<211> LENGTH: 7
<212> TYPE: PRT
<213> ORGANISM: artificial sequence
<220> FEATURE:

<223> OTHER INFORMATION: LCDR2

<400> SEQUENCE: 48

Trp Ala Ser Thr Arg Glu Ser
1               5

<210> SEQ ID NO 49
<211> LENGTH: 8
<212> TYPE: PRT
<213> ORGANISM: artificial sequence
<220> FEATURE:
<223> OTHER INFORMATION: LCDR3

<400> SEQUENCE: 49

Gln Gln Tyr Ser Asp Leu Leu Thr
1               5

<210> SEQ ID NO 50
<211> LENGTH: 112
<212> TYPE: PRT
<213> ORGANISM: artificial sequence
<220> FEATURE:
<223> OTHER INFORMATION: VL

<400> SEQUENCE: 50

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Asp Leu Leu Thr Phe Gly Gly Gly Thr Lys Val Glu Ile Lys
            100                 105                 110

<210> SEQ ID NO 51
<211> LENGTH: 11
<212> TYPE: PRT
<213> ORGANISM: artificial sequence
<220> FEATURE:
<223> OTHER INFORMATION: LCDR1

<400> SEQUENCE: 51

Gln Ala Ser Gln Asp Ile Thr Asn Tyr Leu Asn
1               5                   10

<210> SEQ ID NO 52
<211> LENGTH: 11
<212> TYPE: PRT
<213> ORGANISM: artificial sequence
<220> FEATURE:
<223> OTHER INFORMATION: LCDR1

<400> SEQUENCE: 52

Arg Ala Ser Gln Ser Ile Asn Ser Tyr Leu Asn
1               5                   10

<210> SEQ ID NO 53

<400> SEQUENCE: 53

000

<210> SEQ ID NO 54
<211> LENGTH: 7
<212> TYPE: PRT
<213> ORGANISM: artificial sequence
<220> FEATURE:
<223> OTHER INFORMATION: LCDR2

<400> SEQUENCE: 54

Asp Ala Ser Asn Leu Glu Thr
1               5

<210> SEQ ID NO 55
<211> LENGTH: 8
<212> TYPE: PRT
<213> ORGANISM: artificial sequence
<220> FEATURE:
<223> OTHER INFORMATION: LCDR3

<400> SEQUENCE: 55

Gln Gln Ala Phe Asp Leu Ile Thr
1               5

<210> SEQ ID NO 56
<211> LENGTH: 9
<212> TYPE: PRT
<213> ORGANISM: artificial sequence
<220> FEATURE:
<223> OTHER INFORMATION: LCDR3

<400> SEQUENCE: 56

Gln Gln Lys Ala Ser Ala Pro Ile Thr
1               5

<210> SEQ ID NO 57

<400> SEQUENCE: 57

000

<210> SEQ ID NO 58
<211> LENGTH: 106
<212> TYPE: PRT
<213> ORGANISM: artificial sequence
<220> FEATURE:
<223> OTHER INFORMATION: VL

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Phe Asp Leu Ile Thr
                85                  90                  95

```
Phe Gly Gly Gly Thr Lys Val Glu Ile Lys
            100                 105

<210> SEQ ID NO 59
<211> LENGTH: 107
<212> TYPE: PRT
<213> ORGANISM: artificial sequence
<220> FEATURE:
<223> OTHER INFORMATION: VL

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Ala Ser Ala Pro Ile
                85                  90                  95

Thr Phe Gly Gly Gly Thr Lys Val Glu Ile Lys
            100                 105

<210> SEQ ID NO 60

<400> SEQUENCE: 60

000

<210> SEQ ID NO 61
<211> LENGTH: 11
<212> TYPE: PRT
<213> ORGANISM: artificial sequence
<220> FEATURE:
<223> OTHER INFORMATION: LCDR1

<400> SEQUENCE: 61

Arg Ala Ser Gln Gly Ile Ser Ser Trp Leu Ala
1               5                   10

<210> SEQ ID NO 62
<211> LENGTH: 7
<212> TYPE: PRT
<213> ORGANISM: artificial sequence
<220> FEATURE:
<223> OTHER INFORMATION: LCDR2

<400> SEQUENCE: 62

Ala Ala Ser Ser Leu Gln Ser
1               5

<210> SEQ ID NO 63
<211> LENGTH: 9
<212> TYPE: PRT
<213> ORGANISM: artificial sequence
<220> FEATURE:
<223> OTHER INFORMATION: LCDR3

<400> SEQUENCE: 63

Gln Gln Thr Leu Ser Leu Pro Ile Thr
1               5
```

<210> SEQ ID NO 64
<211> LENGTH: 107
<212> TYPE: PRT
<213> ORGANISM: artificial sequence
<220> FEATURE:
<223> OTHER INFORMATION: VL

<400> SEQUENCE: 64

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Leu Ser Leu Pro Ile
                85                  90                  95

Thr Phe Gly Gly Gly Thr Lys Val Glu Ile Lys
            100                 105

<210> SEQ ID NO 65
<211> LENGTH: 11
<212> TYPE: PRT
<213> ORGANISM: artificial sequence
<220> FEATURE:
<223> OTHER INFORMATION: LCDR1

<400> SEQUENCE: 65

Arg Ala Ser Gln Ser Ile Ser Ser Tyr Leu Asn
1               5                   10

<210> SEQ ID NO 66
<211> LENGTH: 11
<212> TYPE: PRT
<213> ORGANISM: artificial sequence
<220> FEATURE:
<223> OTHER INFORMATION: LCDR1

<400> SEQUENCE: 66

Arg Ala Ser Gln Ser Ile Ser Arg Tyr Leu Asn
1               5                   10

<210> SEQ ID NO 67
<211> LENGTH: 11
<212> TYPE: PRT
<213> ORGANISM: artificial sequence
<220> FEATURE:
<223> OTHER INFORMATION: CONSENSUS
<220> FEATURE:
<221> NAME/KEY: misc_feature
<222> LOCATION: (8)..(8)
<223> OTHER INFORMATION: Xaa can be any naturally occurring amino acid

<400> SEQUENCE: 67

Arg Ala Ser Gln Ser Ile Ser Xaa Tyr Leu Asn
1               5                   10

<210> SEQ ID NO 68
<211> LENGTH: 8
<212> TYPE: PRT

```
<213> ORGANISM: artificial sequence
<220> FEATURE:
<223> OTHER INFORMATION: LCDR3

<400> SEQUENCE: 68

Gln Gln Lys Tyr Asp Leu Leu Thr
1               5

<210> SEQ ID NO 69
<211> LENGTH: 8
<212> TYPE: PRT
<213> ORGANISM: artificial sequence
<220> FEATURE:
<223> OTHER INFORMATION: LCDR3

<400> SEQUENCE: 69

Gln Gln Lys Tyr Phe Asp Ile Thr
1               5

<210> SEQ ID NO 70
<211> LENGTH: 8
<212> TYPE: PRT
<213> ORGANISM: artificial sequence
<220> FEATURE:
<223> OTHER INFORMATION: CONSENSUS
<220> FEATURE:
<221> NAME/KEY: misc_feature
<222> LOCATION: (5)..(7)
<223> OTHER INFORMATION: Xaa can be any naturally occurring amino acid

<400> SEQUENCE: 70

Gln Gln Lys Tyr Xaa Xaa Xaa Thr
1               5

<210> SEQ ID NO 71
<211> LENGTH: 106
<212> TYPE: PRT
<213> ORGANISM: artificial sequence
<220> FEATURE:
<223> OTHER INFORMATION: VL

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Asp Leu Leu Thr
                85                  90                  95

Phe Gly Gly Gly Thr Lys Val Glu Ile Lys
            100                 105

<210> SEQ ID NO 72
<211> LENGTH: 106
<212> TYPE: PRT
<213> ORGANISM: artificial sequence
<220> FEATURE:
<223> OTHER INFORMATION: VL

<400> SEQUENCE: 72
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Phe Asp Ile Thr
                85                  90                  95

Phe Gly Gly Gly Thr Lys Val Glu Ile Lys
            100                 105

<210> SEQ ID NO 73
<211> LENGTH: 106
<212> TYPE: PRT
<213> ORGANISM: artificial sequence
<220> FEATURE:
<223> OTHER INFORMATION: CONSENSUS
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (93)..(95)
<223> OTHER INFORMATION: Xaa can be any naturally occurring amino acid

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Xaa Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Xaa Xaa Xaa Thr
                85                  90                  95

Phe Gly Gly Gly Thr Lys Val Glu Ile Lys
            100                 105

<210> SEQ ID NO 74
<211> LENGTH: 184
<212> TYPE: PRT
<213> ORGANISM: artificial sequence
<220> FEATURE:
<223> OTHER INFORMATION: BCMA SEQUENCE

<400> SEQUENCE: 74

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
            35                  40                  45
```

Val Lys Gly Thr Asn Ala Ile Leu Trp Thr Cys Leu Gly Leu Ser Leu
 50                  55                  60

Ile Ile Ser Leu Ala Val Phe Val Leu Met Phe Leu Leu Arg Lys Ile
 65                  70                  75                  80

Asn Ser Glu Pro Leu Lys Asp Glu Phe Lys Asn Thr Gly Ser Gly Leu
                 85                  90                  95

Leu Gly Met Ala Asn Ile Asp Leu Glu Lys Ser Arg Thr Gly Asp Glu
             100                 105                 110

Ile Ile Leu Pro Arg Gly Leu Glu Tyr Thr Val Glu Glu Cys Thr Cys
         115                 120                 125

Glu Asp Cys Ile Lys Ser Lys Pro Lys Val Asp Ser Asp His Cys Phe
     130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 75
<211> LENGTH: 372
<212> TYPE: DNA
<213> ORGANISM: artificial sequence
<220> FEATURE:
<223> OTHER INFORMATION: DNA VH

<400> SEQUENCE: 75
gaggtgcagc tgttggagtc tgggggaggc ttggtacagc ctggggggtc cctgagactc      60
tcctgtgcag cctctggatt cacctttgat gattatgcca tgcactgggt ccggcaagct     120
ccagggaagg gcctggagtg gtctcaggt attagttgga gtagtggtag cataggctat     180
gcggactctg tgaagggccg attcaccatc tccagagaca cgccaagaa ctccctgtat      240 ctgcaaatga acagtctgag agctgaggac acggcggtgt actactgcgc caaggactcc     300
cctagaaggg acagcttcgg aagcatagca ttcgacatat ggggtcaggg tacaatggtc     360
accgtctcct ca                                                         372

<210> SEQ ID NO 76
<211> LENGTH: 372
<212> TYPE: DNA
<213> ORGANISM: artificial sequence
<220> FEATURE:
<223> OTHER INFORMATION: DNA VH

<400> SEQUENCE: 76
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga gtagtggtag cataggctat     180
gcggactctg tgaagggccg attcaccatc tccagagaca cgccaagaa ctccctgtat      240 ctgcaaatga acagtctgag agctgaggac acggcggtgt actactgcgc caaggactcc     300
cctagaaggg acagcttcgg aagcatagca ttcgacatat ggggtcaggg tacaatggtc     360
accgtctcct ca                                                         372

<210> SEQ ID NO 77
<211> LENGTH: 369

```
<212> TYPE: DNA
<213> ORGANISM: artificial sequence
<220> FEATURE:
<223> OTHER INFORMATION: DNA VH

<400> SEQUENCE: 77
caggtgcagc tggtggagtc tgggggaggc gtggtccagc ctggagagtc cctaagactc      60
tcctgtgcag cgtctggatt caccttcagt agctatggca tgcactgggt ccgccaggct     120
ccaggcaagg ggctggagtg gtggcagtt atatcgtatg agggaagtaa taaatactat     180
gcagactccg tgaagggccg attcaccatc tccagagaca attccaagaa cacgctgtat     240
ctgcaaatga acagcctgag agccgaggac acggcggtgt actactgcgc cagagatact     300
tcctcctacg agacgctag ctacggaatg gacgtatggg gccagggaac aactgtcacc      360
gtctcctca                                                             369

<210> SEQ ID NO 78
<211> LENGTH: 363
<212> TYPE: DNA
<213> ORGANISM: artificial sequence
<220> FEATURE:
<223> OTHER INFORMATION: DNA VH

<400> SEQUENCE: 78
caggtgcagc tggtgcagtc tggggctgag gtgaagaagc ctgggtcctc ggtgaaggtc      60
tcctgcaagg cttctggagg caccttcagc aactatgcta tcagctgggt gcgacaggcc     120
cctggacaag gcttgagtg gatgggaggg atcatcccta tctttggtac agcaaactac     180
gcacagaagt tccagggcag agtcacgatt accgcggacg aatccacgag cacagcctac     240
atggagctga gcagcctgaa atctgaggac acggcggtgt actactgcgc cagaggctct     300
ggatactact caagctggct attcgacata tggggtcagg gtacaatggt caccgtctcc     360
tca                                                                    363

<210> SEQ ID NO 79
<211> LENGTH: 363
<212> TYPE: DNA
<213> ORGANISM: artificial sequence
<220> FEATURE:
<223> OTHER INFORMATION: DNA VH

<400> SEQUENCE: 79
caggtgcagc tggtgcagtc tggggctgag gtgaagaagc ctgggtcctc ggtgaaggtc      60
tcctgcaagg cttctggagg caccttcagc aactatgcta tcagctgggt gcgacaggcc     120
cctggacaag gcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggcggtgt actactgcgc cagaggcagg     300
ggatactact caagctggct attcgacata tggggtcagg gtacaatggt caccgtctcc     360
tca                                                                    363

<210> SEQ ID NO 80
<211> LENGTH: 357
<212> TYPE: DNA
<213> ORGANISM: artificial sequence
<220> FEATURE:
<223> OTHER INFORMATION: DNA VH

<400> SEQUENCE: 80
```

```
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag ggaaggggct ggagtggatt gggagtatct cctatagtgg gagcacctac   180
tacaacccgt ccctcaagag tcgagtcacc atatccgtgg acacgtccaa gaaccagttc   240
tccctgaagc tgagttctgt gaccgccgca gacacggcgg tgtactactg cgccagggat   300
cgtggagaca ccatactaga cgtatggggt cagggtacaa tggtcaccgt ctcctca      357
```

<210> SEQ ID NO 81
<211> LENGTH: 363
<212> TYPE: DNA
<213> ORGANISM: artificial sequence
<220> FEATURE:
<223> OTHER INFORMATION: DNA VH

<400> SEQUENCE: 81

```
cagatcacct tgaaggagtc tggtcctacg ctggtgaaac ccacacagac cctcacgctg    60
acctgcacct tctctggggtt ctcactcagc actagtggag tgggtgtggg ctggatccgt   120
cagcccccag gaaaggccct ggagtggctt gcactcattt attggaatga tgaaaagcgc   180
tacagcccat ctctgaagag caggctcacc atcaccaagg acacctccaa aaaccaggtg   240
gtccttacaa tgaccaacat ggaccctgtg gacacggcgg tgtactactg cgccagagat   300
ccaggagagc aactacaggt tttcgattac tggggacagg gtacattggt caccgtctcc   360
tca                                                                 363
```

<210> SEQ ID NO 82
<211> LENGTH: 357
<212> TYPE: DNA
<213> ORGANISM: artificial sequence
<220> FEATURE:
<223> OTHER INFORMATION: DNA VH

<400> SEQUENCE: 82

```
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag ggaaggggct ggagtggatt gggagtatct cctatagtgg gagcacctac   180
tacaacccgt ccctcaagag tcgagtcacc atatccgtag acacgtccaa gaaccagttc   240
tccctgaagc tgagttctgt gaccgccgca gacacggcgg tgtactactg cgccagagat   300
cgtggagaca ccatactaga cgtatggggt cagggtacaa tggtcaccgt ctcctca      357
```

<210> SEQ ID NO 83
<211> LENGTH: 336
<212> TYPE: DNA
<213> ORGANISM: artificial sequence
<220> FEATURE:
<223> OTHER INFORMATION: DNA VL

<400> SEQUENCE: 83

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagatttac actgaaaatc   240 agcagagtgg aggctgagga tgttgggggtt tattactgca tgcaggcaaa acgcctccct   300
atcacttttg gcggagggac caaggttgag atcaaa                             336
```

<210> SEQ ID NO 84
<211> LENGTH: 321
<212> TYPE: DNA
<213> ORGANISM: artificial sequence
<220> FEATURE:
<223> OTHER INFORMATION: DNA VL

<400> SEQUENCE: 84
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaaa gggccactgg catcccagcc     180
aggttcagtg gcagtgggtc tgggacagac ttcactctca ccatcagcag cctagagcct     240
gaagattttg cagtttatta ctgtcagcag gccagtgccc tccctctcac ttttggcgga     300
gggaccaagg ttgagatcaa a                                                321

<210> SEQ ID NO 85
<211> LENGTH: 321
<212> TYPE: DNA
<213> ORGANISM: artificial sequence
<220> FEATURE:
<223> OTHER INFORMATION: DNA VL

<400> SEQUENCE: 85
gaaatagtga tgacgcagtc tccagccacc ctgtctgtgt ctccagggga aagagccacc      60
ctctcctgca gggccagtca gagtgttggc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tccgtcaatc tccctatcac ttttggcgga     300
gggaccaagg ttgagatcaa a                                                321

<210> SEQ ID NO 86
<211> LENGTH: 321
<212> TYPE: DNA
<213> ORGANISM: artificial sequence
<220> FEATURE:
<223> OTHER INFORMATION: DNA VL

<400> SEQUENCE: 86
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag tactcccact ggcctcctac ttttggcgga     300
gggaccaagg ttgagatcaa a                                                321

<210> SEQ ID NO 87
<211> LENGTH: 336
<212> TYPE: DNA
<213> ORGANISM: artificial sequence
<220> FEATURE:
<223> OTHER INFORMATION: DNA VL

<400> SEQUENCE: 87
gacatcgtgc tgacccagtc tccagactcc ctggctgtgt ctctgggcga gagggccacc      60

```
atcaactgca agtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcagta ctccgacctc    300 ctcactttg gcggagggac caaggttgag atcaaa                                336
```

<210> SEQ ID NO 88
<211> LENGTH: 318
<212> TYPE: DNA
<213> ORGANISM: artificial sequence
<220> FEATURE:
<223> OTHER INFORMATION: DNA VL

<400> SEQUENCE: 88

```
gacatccaga tgacccagtc tccatcctcc ctgtctgcat ctgtaggaga cagagtcacc     60
atcacttgcc aggcgagtca ggacattacc aactatttaa attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcagcag gccttcgacc tcatcacttt tggcggaggg    300
accaaggttg agatcaaa                                                  318
```

<210> SEQ ID NO 89
<211> LENGTH: 321
<212> TYPE: DNA
<213> ORGANISM: artificial sequence
<220> FEATURE:
<223> OTHER INFORMATION: DNA VL

<400> SEQUENCE: 89

```
gacatccaga tgacccagtc tccatcctcc ctgtctgcat ctgtaggaga cagagtcacc     60
atcacttgcc gggcaagtca gagcattaac agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcaa aaagccagtg cccctatcac ttttggcgga    300
gggaccaagg ttgagatcaa a                                              321
```

<210> SEQ ID NO 90
<211> LENGTH: 321
<212> TYPE: DNA
<213> ORGANISM: artificial sequence
<220> FEATURE:
<223> OTHER INFORMATION: DNA VL

<400> SEQUENCE: 90

```
gacatccaga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ctgtcagcag acactcagtc tccctatcac ttttggcgga    300
gggaccaagg ttgagatcaa a                                              321
```

<210> SEQ ID NO 91
<211> LENGTH: 318

```
<212> TYPE: DNA
<213> ORGANISM: artificial sequence
<220> FEATURE:
<223> OTHER INFORMATION: DNA VL

<400> SEQUENCE: 91
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcaa aaatacgacc tcctcacttt tggcggaggg    300
accaaggttg agatcaaa                                                   318

<210> SEQ ID NO 92
<211> LENGTH: 318
<212> TYPE: DNA
<213> ORGANISM: artificial sequence
<220> FEATURE:
<223> OTHER INFORMATION: DNA VL

<400> SEQUENCE: 92
gacatccaga tgacccagtc tccatcctcc ctgtctgcat ctgtaggaga cagagtcacc     60
atcacttgcc gggcaagtca gagcattagc agatatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcaa aaatacttcg acatcacttt tggcggaggg    300
accaaggttg agatcaaa                                                   318

<210> SEQ ID NO 93
<211> LENGTH: 18
<212> TYPE: PRT
<213> ORGANISM: artificial sequence
<220> FEATURE:
<223> OTHER INFORMATION: LINKER

<400> SEQUENCE: 93

Gly Ser Thr Ser Gly Ser Gly Lys Pro Gly Ser Gly Glu Gly Ser Thr
1               5                  10                  15

Lys Gly

<210> SEQ ID NO 94
<211> LENGTH: 54
<212> TYPE: DNA
<213> ORGANISM: artificial sequence
<220> FEATURE:
<223> OTHER INFORMATION: LINKER DNA

<400> SEQUENCE: 94
ggcagcacca gcggctccgg caagcctggc tctggcgagg gcagcacaaa ggga           54

<210> SEQ ID NO 95
<211> LENGTH: 45
<212> TYPE: PRT
<213> ORGANISM: artificial sequence
<220> FEATURE:
<223> OTHER INFORMATION: HINGE

<400> SEQUENCE: 95

Thr Thr Thr Pro Ala Pro Arg Pro Pro Thr Pro Ala Pro Thr Ile Ala
```

```
                1               5                  10                 15
Ser Gln Pro Leu Ser Leu Arg Pro Glu Ala Cys Arg Pro Ala Ala Gly
            20                  25                 30

Gly Ala Val His Thr Arg Gly Leu Asp Phe Ala Cys Asp
            35                  40                 45
```

<210> SEQ ID NO 96
<211> LENGTH: 135
<212> TYPE: DNA
<213> ORGANISM: artificial sequence
<220> FEATURE:
<223> OTHER INFORMATION: HINGE DNA

<400> SEQUENCE: 96

```
accaccaccc ctgcccctag acctcccacc ccagccccaa caatcgccag ccagcctctg     60
tctctgcggc ccgaagcctg tagacctgct gccggcggag ccgtgcacac cagaggcctg    120
gacttcgcct gcgac                                                     135
```

<210> SEQ ID NO 97
<211> LENGTH: 54
<212> TYPE: DNA
<213> ORGANISM: artificial sequence
<220> FEATURE:
<223> OTHER INFORMATION: LINKER DNA

<400> SEQUENCE: 97

```
ggcagcacca gcggcagcgg caagcccggc tccggagagg gcagcaccaa gggc           54
```

<210> SEQ ID NO 98
<211> LENGTH: 135
<212> TYPE: DNA
<213> ORGANISM: artificial sequence
<220> FEATURE:
<223> OTHER INFORMATION: HINGE DNA

<400> SEQUENCE: 98

```
accacaacac ctgctccaag gccccccaca cccgctccaa ctatagccag ccaaccattg     60
agcctcagac ctgaagcttg caggcccgca gcaggaggcg ccgtccatac gcgaggcctg    120
gacttcgcgt gtgat                                                     135
```

<210> SEQ ID NO 99
<211> LENGTH: 254
<212> TYPE: PRT
<213> ORGANISM: artificial sequence
<220> FEATURE:
<223> OTHER INFORMATION: scFv

<400> SEQUENCE: 99

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

Lys Arg Leu Pro Ile Thr Phe Gly Gly Gly Thr Lys Val Glu Ile Lys
                100                 105                 110

Gly Ser Thr Ser Gly Ser Gly Lys Pro Gly Ser Gly Glu Gly Ser Thr
            115                 120                 125

Lys Gly Glu Val Gln Leu Leu Glu Ser Gly Gly Gly Leu Val Gln Pro
130                 135                 140

Gly Gly Ser Leu Arg Leu Ser Cys Ala Ala Ser Gly Phe Thr Phe Asp
145                 150                 155                 160

Asp Tyr Ala Met His Trp Val Arg Gln Ala Pro Gly Lys Gly Leu Glu
                165                 170                 175

Trp Val Ser Gly Ile Ser Trp Ser Gly Ser Ile Gly Tyr Ala Asp
                180                 185                 190

Ser Val Lys Gly Arg Phe Thr Ile Ser Arg Asp Asn Ala Lys Asn Ser
                195                 200                 205

Leu Tyr Leu Gln Met Asn Ser Leu Arg Ala Glu Asp Thr Ala Val Tyr
            210                 215                 220

Tyr Cys Ala Lys Asp Ser Pro Arg Arg Asp Ser Phe Gly Ser Ile Ala
225                 230                 235                 240

Phe Asp Ile Trp Gly Gln Gly Thr Met Val Thr Val Ser Ser
                245                 250

<210> SEQ ID NO 100
<211> LENGTH: 762
<212> TYPE: DNA
<213> ORGANISM: artificial sequence
<220> FEATURE:
<223> OTHER INFORMATION: scFv DNA

<400> SEQUENCE: 100

```
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaggcaaa acgcctccct     300
atcactttg cggagggac caaggttgag atcaaaggca gcaccagcgg ctccggcaag     360
cctggctctg gcgagggcag cacaaaggga gaggtgcagc tgttggagtc tggggaggc      420
ttggtacagc ctgggggtc cctgagactc tcctgtgcag cctctggatt cacctttgat     480
gattatgcca tgcactgggt ccggcaagct ccagggaagg gcctggagtg gtctctcaggt     540
attagttgga gtagtggtag cataggctat gcggactctg tgaagggccg attcaccatc     600
tccagagaca acgccaagaa ctccctgtat ctgcaaatga acagtctgag agctgaggac     660
acggcggtgt actactgcgc caaggactcc cctagaaggg acagcttcgg aagcatagca     720
ttcgacatat ggggtcaggg tacaatggtc accgtctcct ca                        762
```

<210> SEQ ID NO 101
<211> LENGTH: 526
<212> TYPE: PRT
<213> ORGANISM: artificial sequence
<220> FEATURE:
<223> OTHER INFORMATION: scFv-hFc

<400> SEQUENCE: 101

Asp Ile Val Met Thr Gln Ser Pro Leu Ser Leu Pro Val Thr Pro Gly
1               5                   10                  15

```
Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Lys Arg Leu Pro Ile Thr Phe Gly Gly Gly Thr Lys Val Glu Ile Lys
            100                 105                 110

Gly Ser Thr Ser Gly Ser Gly Lys Pro Gly Ser Gly Glu Gly Ser Thr
        115                 120                 125

Lys Gly Glu Val Gln Leu Leu Glu Ser Gly Gly Gly Leu Val Gln Pro
130                 135                 140

Gly Gly Ser Leu Arg Leu Ser Cys Ala Ala Ser Gly Phe Thr Phe Asp
145                 150                 155                 160

Asp Tyr Ala Met His Trp Val Arg Gln Ala Pro Gly Lys Gly Leu Glu
                165                 170                 175

Trp Val Ser Gly Ile Ser Trp Ser Ser Gly Ser Ile Gly Tyr Ala Asp
            180                 185                 190

Ser Val Lys Gly Arg Phe Thr Ile Ser Arg Asp Asn Ala Lys Asn Ser
        195                 200                 205

Leu Tyr Leu Gln Met Asn Ser Leu Arg Ala Glu Asp Thr Ala Val Tyr
210                 215                 220

Tyr Cys Ala Lys Asp Ser Pro Arg Arg Asp Ser Phe Gly Ser Ile Ala
225                 230                 235                 240

Phe Asp Ile Trp Gly Gln Gly Thr Met Val Thr Val Ser Ser Thr Thr
                245                 250                 255

Thr Pro Ala Pro Arg Pro Pro Thr Pro Ala Pro Thr Ile Ala Ser Gln
            260                 265                 270

Pro Leu Ser Leu Arg Pro Glu Ala Cys Arg Pro Ala Ala Gly Gly Ala
        275                 280                 285

Val His Thr Arg Gly Leu Asp Phe Ala Cys Asp Asp Lys Thr His Thr
290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
        355                 360                 365

Lys Pro Arg Glu Glu Gln Tyr Asn Ser Thr Tyr Arg Val Val Ser Val
370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
            420                 425                 430
```

Ser Arg Asp Glu Leu Thr Lys Asn Gln Val Ser Leu Thr Cys Leu Val
435                 440                 445

Lys Gly Phe Tyr Pro Ser Asp Ile Ala Val Glu Trp Glu Ser Asn Gly
450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Ala Leu His
                500                 505                 510

Asn His Tyr Thr Gln Lys Ser Leu Ser Leu Ser Pro Gly Lys
515                 520                 525

<210> SEQ ID NO 102
<211> LENGTH: 249
<212> TYPE: PRT
<213> ORGANISM: artificial sequence
<220> FEATURE:
<223> OTHER INFORMATION: scFv

<400> SEQUENCE: 102

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Ser Ala Leu Pro Leu
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Gln Pro Gly Arg Ser Leu Arg
    130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Ser Ser Gly Ser Ile Gly Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Lys Asp
    210                 215                 220

Ser Pro Arg Arg Asp Ser Phe Gly Ser Ile Ala Phe Asp Ile Trp Gly
225                 230                 235                 240

Gln Gly Thr Met Val Thr Val Ser Ser
                245

<210> SEQ ID NO 103
<211> LENGTH: 747

<212> TYPE: DNA
<213> ORGANISM: artificial sequence
<220> FEATURE:
<223> OTHER INFORMATION: scFv DNA

<400> SEQUENCE: 103

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaaa gggccactgg catcccagcc     180
aggttcagtg gcagtgggtc tgggacagac ttcactctca ccatcagcag cctagagcct     240
gaagattttg cagtttatta ctgtcagcag gccagtgccc tccctctcac ttttggcgga     300
gggaccaagg ttgagatcaa aggcagcacc agcggctccg gcaagcctgg ctctggcgag     360
ggcagcacaa aggagaagt gcagctggtg gagtctgggg gaggcttggt acagcctggc     420
aggtccctga gactctcctg tgcagcctct ggattcacct ttgatgatta tgccatgcac     480
tgggtccggc aagctccagg aagggcctg gagtgggtct caggtattag ttggagtagt     540
ggtagcatag gctatgcgga ctctgtgaag gccgattca ccatctccag agacaacgcc     600
aagaactccc tgtatctgca aatgaacagt ctgagagctg aggacacggc ggtgtactac     660
tgcgccaagg actcccctag aagggacagc ttcggaagca tagcattcga catatggggt     720
cagggtacaa tggtcaccgt ctcctca                                          747
```

<210> SEQ ID NO 104
<211> LENGTH: 521
<212> TYPE: PRT
<213> ORGANISM: artificial sequence
<220> FEATURE:
<223> OTHER INFORMATION: scFv-hFc

<400> SEQUENCE: 104

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
                20                  25                  30
Leu Ala Trp Tyr Gln Gln Lys Pro Gly Gln Ala Pro Arg Leu Leu Ile
            35                  40                  45
Tyr Asp Ala Ser Lys Arg Ala Thr Gly Ile Pro Ala Arg Phe Ser Gly
50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Ala Ser Ala Leu Pro Leu
                85                  90                  95
Thr Phe Gly Gly Gly Thr Lys Val Glu Ile Lys Gly Ser Thr Ser Gly
            100                 105                 110
Ser Gly Lys Pro Gly Ser Gly Glu Gly Ser Thr Lys Gly Glu Val Gln
        115                 120                 125
Leu Val Glu Ser Gly Gly Gly Leu Val Gln Pro Gly Arg Ser Leu Arg
    130                 135                 140
Leu Ser Cys Ala Ala Ser Gly Phe Thr Phe Asp Asp Tyr Ala Met His
145                 150                 155                 160
Trp Val Arg Gln Ala Pro Gly Lys Gly Leu Glu Trp Val Ser Gly Ile
                165                 170                 175
Ser Trp Ser Ser Gly Ser Ile Gly Tyr Ala Asp Ser Val Lys Gly Arg
            180                 185                 190
```

Phe Thr Ile Ser Arg Asp Asn Ala Lys Asn Ser Leu Tyr Leu Gln Met
                195                 200                 205

Asn Ser Leu Arg Ala Glu Asp Thr Ala Val Tyr Tyr Cys Ala Lys Asp
        210                 215                 220

Ser Pro Arg Arg Asp Ser Phe Gly Ser Ile Ala Phe Asp Ile Trp Gly
225                 230                 235                 240

Gln Gly Thr Met Val Thr Val Ser Ser Thr Thr Pro Ala Pro Arg
                245                 250                 255

Pro Pro Thr Pro Ala Pro Thr Ile Ala Ser Gln Pro Leu Ser Leu Arg
                260                 265                 270

Pro Glu Ala Cys Arg Pro Ala Ala Gly Gly Ala Val His Thr Arg Gly
                275                 280                 285

Leu Asp Phe Ala Cys Asp Asp Lys Thr His Thr Cys Pro Pro Cys Pro
        290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
                340                 345                 350

Val Asp Gly Val Glu Val His Asn Ala Lys Thr Lys Pro Arg Glu Glu
                355                 360                 365

Gln Tyr Asn Ser Thr Tyr Arg Val Val Ser Val Leu Thr Val Leu His
        370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Asp Glu Leu
                420                 425                 430

Thr Lys Asn Gln Val Ser Leu Thr Cys Leu Val Lys Gly Phe Tyr Pro
        435                 440                 445

Ser Asp Ile Ala Val Glu Trp Glu Ser Asn Gly Gln Pro Glu Asn Asn
450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
        500                 505                 510

Lys Ser Leu Ser Leu Ser Pro Gly Lys
        515                 520

<210> SEQ ID NO 105
<211> LENGTH: 249
<212> TYPE: PRT
<213> ORGANISM: artificial sequence
<220> FEATURE:
<223> OTHER INFORMATION: scFv

<400> SEQUENCE: 105

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
                20                  25                  30

```
Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Ser Val Asn Leu Pro Ile
                 85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
            115                 120                 125

Leu Val Glu Ser Gly Gly Gly Leu Val Gln Pro Gly Arg Ser Leu Arg
130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Ser Ser Gly Ser Ile Gly Tyr Ala Asp Ser Val Lys Gly Arg
            180                 185                 190

Phe Thr Ile Ser Arg Asp Asn Ala Lys Asn Ser Leu Tyr Leu Gln Met
            195                 200                 205

Asn Ser Leu Arg Ala Glu Asp Thr Ala Val Tyr Tyr Cys Ala Lys Asp
210                 215                 220

Ser Pro Arg Arg Asp Ser Phe Gly Ser Ile Ala Phe Asp Ile Trp Gly
225                 230                 235                 240

Gln Gly Thr Met Val Thr Val Ser Ser
            245

<210> SEQ ID NO 106
<211> LENGTH: 747
<212> TYPE: DNA
<213> ORGANISM: artificial sequence
<220> FEATURE:
<223> OTHER INFORMATION: scFv DNA

<400> SEQUENCE: 106
gaaatagtga tgacgcagtc tccagccacc ctgtctgtgt ctccagggga agagccacc     60 ctctcctgca gggccagtca gagtgttggc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tccgtcaatc tccctatcac ttttggcgga   300
gggaccaagg ttgagatcaa aggcagcacc agcggctccg gcaagcctgg ctctggcgag   360
ggcagcacaa agggagaagt gcagctggtg gagtctgggg gaggcttggt acagcctggc   420
aggtccctga ctctcctgtg cagcctct ggattcacct ttgatgatta cgccatgcac   480
tgggtccggc aagctccagg aagggcctg gagtgggtct caggtattag ttggagtagt   540
ggtagcatag ctatgcgga ctctgtgaag ggccgattca ccatctccag agacaacgcc   600
aagaactccc tgtatctgca aatgaacagt ctgagagctg aggacacggc ggtgtactac   660
tgcgccaagg actcccctag aagggacagc ttcggaagca tagcattcga catatgggt   720 cagggtacaa tggtcaccgt ctcctca                                      747
```

<210> SEQ ID NO 107
<211> LENGTH: 521
<212> TYPE: PRT
<213> ORGANISM: artificial sequence
<220> FEATURE:
<223> OTHER INFORMATION: scFv-hFc

<400> SEQUENCE: 107

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Val Asn Leu Pro Ile
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Gln Pro Gly Arg Ser Leu Arg
130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Ser Ser Gly Ser Ile Gly Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Lys Asp
210                 215                 220

Ser Pro Arg Arg Asp Ser Phe Gly Ser Ile Ala Phe Asp Ile Trp Gly
225                 230                 235                 240

Gln Gly Thr Met Val Thr Val Ser Ser Thr Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Asp Lys Thr His Thr Cys Pro Pro Cys Pro
290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
            340                 345                 350

Val Asp Gly Val Glu Val His Asn Ala Lys Thr Lys Pro Arg Glu Glu
        355                 360                 365

Gln Tyr Asn Ser Thr Tyr Arg Val Val Ser Val Leu Thr Val Leu His
```

```
            370                 375                 380
Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Asp Glu Leu
            420                 425                 430

Thr Lys Asn Gln Val Ser Leu Thr Cys Leu Val Lys Gly Phe Tyr Pro
            435                 440                 445

Ser Asp Ile Ala Val Glu Trp Glu Ser Asn Gly Gln Pro Glu Asn Asn
        450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
            485                 490                 495

Phe Ser Cys Ser Val Met His Glu Ala Leu His Asn His Tyr Thr Gln
                500                 505                 510

Lys Ser Leu Ser Leu Ser Pro Gly Lys
            515                 520

<210> SEQ ID NO 108
<211> LENGTH: 248
<212> TYPE: PRT
<213> ORGANISM: artificial sequence
<220> FEATURE:
<223> OTHER INFORMATION: scFv

<400> SEQUENCE: 108

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser His Trp Pro Pro
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Val Gln
            115                 120                 125

Leu Val Glu Ser Gly Gly Gly Val Val Gln Pro Gly Arg Ser Leu Arg
        130                 135                 140

Leu Ser Cys Ala Ala Ser Gly Phe Thr Phe Ser Ser Tyr Gly Met His
145                 150                 155                 160

Trp Val Arg Gln Ala Pro Gly Lys Gly Leu Glu Trp Val Ala Val Ile
                165                 170                 175

Ser Tyr Glu Gly Ser Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Arg Asp
```

Thr Ser Ser Tyr Gly Asp Ala Ser Tyr Gly Met Asp Val Trp Gly Gln
225                 230                 235                 240

Gly Thr Thr Val Thr Val Ser Ser
                245

<210> SEQ ID NO 109
<211> LENGTH: 744
<212> TYPE: DNA
<213> ORGANISM: artificial sequence
<220> FEATURE:
<223> OTHER INFORMATION: scFv DNA

<400> SEQUENCE: 109

| | | | | | | |
|---|---|---|---|---|---|---|
| gaaattgtgt | tgacacagtc | tccagccacc | ctgtctttgt | ctccagggga | aagagccacc | 60 |
| ctctcctgca | gggccagtca | gagtgttagc | agctacttag | cctggtacca | acagaaacct | 120 |
| ggccaggctc | ccaggctcct | catctatgat | gcatccaaca | gggccactgg | catcccagcc | 180 |
| aggttcagtg | gcagtgggtc | tgggacagac | ttcactctca | ccatcagcag | cctagagcct | 240 |
| gaagattttg | cagtttatta | ctgtcagcag | tactcccact | ggcctcctac | ttttggcgga | 300 |
| gggaccaagg | ttgagatcaa | aggcagcacc | agcggctccg | gcaagcctgg | ctctggcgag | 360 |
| ggcagcacaa | agggacaggt | gcagctggtg | gagtctgggg | gaggcgtggt | ccagcctggg | 420 |
| aggtccctaa | gactctcctg | tgcagcgtct | ggattcacct | tcagtagcta | tggcatgcac | 480 |
| tgggtccgcc | aggctccagg | caaggggctg | gagtgggtgg | cagttatatc | gtatgaggga | 540 |
| agtaataaat | actatgcaga | ctccgtgaag | ggccgattca | ccatctccag | agacaattcc | 600 |
| aagaacacgc | tgtatctgca | aatgaacagc | ctgagagccg | aggacacggc | ggtgtactac | 660 |
| tgcgccagag | atacttcctc | ctacggagac | gctagctacg | gaatggacgt | atggggccag | 720 |
| ggaacaactg | tcaccgtctc | ctca | | | | 744 |

<210> SEQ ID NO 110
<211> LENGTH: 520
<212> TYPE: PRT
<213> ORGANISM: artificial sequence
<220> FEATURE:
<223> OTHER INFORMATION: scFv-hFc

<400> SEQUENCE: 110

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser His Trp Pro Pro
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Ser Thr Lys Gly Gln Val Gln
        115                 120                 125

Leu Val Glu Ser Gly Gly Gly Val Val Gln Pro Gly Arg Ser Leu Arg

```
                    130                 135                 140
Leu Ser Cys Ala Ala Ser Gly Phe Thr Phe Ser Ser Tyr Gly Met His
145                 150                 155                 160

Trp Val Arg Gln Ala Pro Gly Lys Gly Leu Glu Trp Val Ala Val Ile
                    165                 170                 175

Ser Tyr Glu Gly Ser Asn Lys Tyr Tyr Ala Asp Ser Val Lys Gly Arg
                180                 185                 190

Phe Thr Ile Ser Arg Asp Asn Ser Lys Asn Thr Leu Tyr Leu Gln Met
            195                 200                 205

Asn Ser Leu Arg Ala Glu Asp Thr Ala Val Tyr Tyr Cys Ala Arg Asp
210                 215                 220

Thr Ser Tyr Gly Asp Ala Ser Tyr Gly Met Asp Val Trp Gly Gln Gly
225                 230                 235                 240

Thr Thr Val Thr Val Ser Ser Thr Thr Pro Ala Pro Arg Pro
                245                 250                 255

Pro Thr Pro Ala Pro Thr Ile Ala Ser Gln Pro Leu Ser Leu Arg Pro
                260                 265                 270

Glu Ala Cys Arg Pro Ala Ala Gly Gly Ala Val His Thr Arg Gly Leu
                275                 280                 285

Asp Phe Ala Cys Asp Asp Lys Thr His Thr Cys Pro Pro Cys Pro Ala
            290                 295                 300

Pro Glu Leu Leu Gly Gly Pro Ser Val Phe Leu Phe Pro Pro Lys Pro
305                 310                 315                 320

Lys Asp Thr Leu Met Ile Ser Arg Thr Pro Glu Val Thr Cys Val Val
                325                 330                 335

Val Asp Val Ser His Glu Asp Pro Glu Val Lys Phe Asn Trp Tyr Val
                340                 345                 350

Asp Gly Val Glu Val His Asn Ala Lys Thr Lys Pro Arg Glu Glu Gln
                355                 360                 365

Tyr Asn Ser Thr Tyr Arg Val Val Ser Val Leu Thr Val Leu His Gln
            370                 375                 380

Asp Trp Leu Asn Gly Lys Glu Tyr Lys Cys Lys Val Ser Asn Lys Ala
385                 390                 395                 400

Leu Pro Ala Pro Ile Glu Lys Thr Ile Ser Lys Ala Lys Gly Gln Pro
                405                 410                 415

Arg Glu Pro Gln Val Tyr Thr Leu Pro Pro Ser Arg Asp Glu Leu Thr
                420                 425                 430

Lys Asn Gln Val Ser Leu Thr Cys Leu Val Lys Gly Phe Tyr Pro Ser
            435                 440                 445

Asp Ile Ala Val Glu Trp Glu Ser Asn Gly Gln Pro Glu Asn Asn Tyr
    450                 455                 460

Lys Thr Thr Pro Pro Val Leu Asp Ser Asp Gly Ser Phe Phe Leu Tyr
465                 470                 475                 480

Ser Lys Leu Thr Val Asp Lys Ser Arg Trp Gln Gln Gly Asn Val Phe
                485                 490                 495

Ser Cys Ser Val Met His Glu Ala Leu His Asn His Tyr Thr Gln Lys
                500                 505                 510

Ser Leu Ser Leu Ser Pro Gly Lys
                515                 520

<210> SEQ ID NO 111
<211> LENGTH: 251
<212> TYPE: PRT
<213> ORGANISM: artificial sequence
```

<220> FEATURE:
<223> OTHER INFORMATION: scFv

<400> SEQUENCE: 111

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Asp Leu Leu Thr Phe Gly Gly Gly Thr Lys Val Glu Ile Lys
            100                 105                 110

Gly Ser Thr Ser Gly Ser Gly Lys Pro Gly Ser Gly Glu Gly Ser Thr
        115                 120                 125

Lys Gly Gln Val Gln Leu Val Gln Ser Gly Ala Glu Val Lys Lys Pro
    130                 135                 140

Gly Ser Ser Val Lys Val Ser Cys Lys Ala Ser Gly Gly Thr Phe Ser
145                 150                 155                 160

Asn Tyr Ala Ile Ser Trp Val Arg Gln Ala Pro Gly Gln Gly Leu Glu
                165                 170                 175

Trp Met Gly Gly Ile Ile Pro Ile Phe Gly Thr Ala Asn Tyr Ala Gln
            180                 185                 190

Lys Phe Gln Gly Arg Val Thr Ile Thr Ala Asp Glu Ser Thr Ser Thr
        195                 200                 205

Ala Tyr Met Glu Leu Ser Ser Leu Lys Ser Glu Asp Thr Ala Val Tyr
    210                 215                 220

Tyr Cys Ala Arg Gly Ser Gly Tyr Tyr Ser Ser Trp Leu Phe Asp Ile
225                 230                 235                 240

Trp Gly Gln Gly Thr Met Val Thr Val Ser Ser
            245                 250

<210> SEQ ID NO 112
<211> LENGTH: 753
<212> TYPE: DNA
<213> ORGANISM: artificial sequence
<220> FEATURE:
<223> OTHER INFORMATION: scFv DNA

<400> SEQUENCE: 112
gacatcgtgc tgacccagtc tccagactcc ctggctgtgt ctctgggcga gagggccacc     60
atcaactgca gtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg gacagatttt cactctcacc    240
atcagcagcc tgcaggctga agatgtggca gtttattact gtcagcagta ctccgacctc    300 ctcactttg gcggagggac caaggttgag atcaaaggca gcaccagcgg ctccggcaag    360
cctggctctg gcgagggcag cacaaaggga caggtgcagc tggtgcagtc tggggctgag    420
gtgaagaagc ctgggtcctc ggtgaaggtc tcctgcaagg cttctggagg caccttcagc    480

```
aactatgcta tcagctgggt gcgacaggcc cctggacaag ggcttgagtg gatgggaggg      540 atcatccota tctttggtac agcaaactac gcacagaagt tccagggcag agtcacgatt      600
accgcggacg aatccacgag cacagcctac atggagctga gcagcctgaa atctgaggac      660
acggcggtgt actactgcgc cagaggctct ggatactact caagctggct attcgacata      720
tggggtcagg gtacaatggt caccgtctcc tca                                   753
```

<210> SEQ ID NO 113
<211> LENGTH: 523
<212> TYPE: PRT
<213> ORGANISM: artificial sequence
<220> FEATURE:
<223> OTHER INFORMATION: scFv-hFc

<400> SEQUENCE: 113

```
Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Asp Leu Leu Thr Phe Gly Gly Gly Thr Lys Val Glu Ile Lys
            100                 105                 110

Gly Ser Thr Ser Gly Ser Gly Lys Pro Gly Ser Gly Glu Gly Ser Thr
        115                 120                 125

Lys Gly Gln Val Gln Leu Val Gln Ser Gly Ala Glu Val Lys Lys Pro
    130                 135                 140

Gly Ser Ser Val Lys Val Ser Cys Lys Ala Ser Gly Gly Thr Phe Ser
145                 150                 155                 160

Asn Tyr Ala Ile Ser Trp Val Arg Gln Ala Pro Gly Gln Gly Leu Glu
                165                 170                 175

Trp Met Gly Gly Ile Ile Pro Ile Phe Gly Thr Ala Asn Tyr Ala Gln
            180                 185                 190

Lys Phe Gln Gly Arg Val Thr Ile Thr Ala Asp Glu Ser Thr Ser Thr
        195                 200                 205

Ala Tyr Met Glu Leu Ser Ser Leu Lys Ser Glu Asp Thr Ala Val Tyr
    210                 215                 220

Tyr Cys Ala Arg Gly Ser Gly Tyr Tyr Ser Ser Trp Leu Phe Asp Ile
225                 230                 235                 240

Trp Gly Gln Gly Thr Met Val Thr Val Ser Ser Thr Thr Thr Pro Ala
                245                 250                 255

Pro Arg Pro Pro Thr Pro Ala Pro Thr Ile Ala Ser Gln Pro Leu Ser
            260                 265                 270

Leu Arg Pro Glu Ala Cys Arg Pro Ala Ala Gly Gly Ala Val His Thr
        275                 280                 285

Arg Gly Leu Asp Phe Ala Cys Asp Asp Lys Thr His Thr Cys Pro Pro
    290                 295                 300

Cys Pro Ala Pro Glu Leu Leu Gly Gly Pro Ser Val Phe Leu Phe Pro
305                 310                 315                 320
```

```
Pro Lys Pro Lys Asp Thr Leu Met Ile Ser Arg Thr Pro Glu Val Thr
            325                 330                 335

Cys Val Val Val Asp Val Ser His Glu Asp Pro Glu Val Lys Phe Asn
            340                 345                 350

Trp Tyr Val Asp Gly Val Glu Val His Asn Ala Lys Thr Lys Pro Arg
            355                 360                 365

Glu Glu Gln Tyr Asn Ser Thr Tyr Arg Val Val Ser Val Leu Thr Val
            370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
            405                 410                 415

Gly Gln Pro Arg Glu Pro Gln Val Tyr Thr Leu Pro Pro Ser Arg Asp
            420                 425                 430

Glu Leu Thr Lys Asn Gln Val Ser Leu Thr Cys Leu Val Lys Gly Phe
            435                 440                 445

Tyr Pro Ser Asp Ile Ala Val Glu Trp Glu Ser Asn Gly Gln Pro Glu
            450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
            485                 490                 495

Asn Val Phe Ser Cys Ser Val Met His Glu Ala Leu His Asn His Tyr
            500                 505                 510

Thr Gln Lys Ser Leu Ser Leu Ser Pro Gly Lys
            515                 520

<210> SEQ ID NO 114
<211> LENGTH: 245
<212> TYPE: PRT
<213> ORGANISM: artificial sequence
<220> FEATURE:
<223> OTHER INFORMATION: scFv

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Phe Asp Leu Ile Thr
            85                  90                  95

Phe Gly Gly Gly Thr Lys Val Glu Ile Lys Gly Ser Thr Ser Gly Ser
            100                 105                 110

Gly Lys Pro Gly Ser Gly Glu Gly Ser Thr Lys Gly Gln Val Gln Leu
            115                 120                 125

Val Gln Ser Gly Ala Glu Val Lys Lys Pro Gly Ser Ser Val Lys Val
            130                 135                 140

Ser Cys Lys Ala Ser Gly Gly Thr Phe Ser Asn Tyr Ala Ile Ser Trp
145                 150                 155                 160
```

Val Arg Gln Ala Pro Gly Gln Gly Leu Glu Trp Met Gly Ile Ile
            165                 170                 175

Pro Ile Phe Gly Thr Ala Asn Tyr Ala Gln Lys Phe Gln Gly Arg Val
            180                 185                 190

Thr Ile Thr Ala Asp Glu Ser Thr Ser Thr Ala Tyr Met Glu Leu Ser
        195                 200                 205

Ser Leu Arg Ser Glu Asp Thr Ala Val Tyr Tyr Cys Ala Arg Gly Arg
    210                 215                 220

Gly Tyr Tyr Ser Ser Trp Leu Phe Asp Ile Trp Gly Gln Gly Thr Met
225                 230                 235                 240

Val Thr Val Ser Ser
            245

<210> SEQ ID NO 115
<211> LENGTH: 735
<212> TYPE: DNA
<213> ORGANISM: artificial sequence
<220> FEATURE:
<223> OTHER INFORMATION: scFv DNA

<400> SEQUENCE: 115
gacatccaga tgacccagtc tccatcctcc ctgtctgcat ctgtaggaga cagagtcacc        60
atcacttgcc aggcgagtca ggacattacc aactatttaa attggtatca gcagaaacca      120
gggaaagccc ctaagctcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcagcag gccttcgacc tcatcacttt tggcggaggg      300
accaaggttg agatcaaagg cagcaccagc ggctccggca gcctggctc tggcgagggc       360 agcacaaagg gacaggtgca gctggtgcag tctggggctg aggtgaagaa gcctgggtcc      420
tcggtgaagg tctcctgcaa ggcttctgga ggcaccttca gcaactatgc tatcagctgg      480
gtgcgacagg cccctggaca agggcttgag tggatgggag ggatcatccc tatctttggt      540
acagcaaact acgcacagaa gttccagggc agagtcacga ttaccgcgga cgaatccacg      600
agcacagcct acatggagct gagcagcctg agatctgagg acacggcggt gtactactgc      660
gccagaggca gggatactac tcaagctggg ctattcgaca tatggggtca gggtacaatg      720
gtcaccgtct cctca                                                      735

<210> SEQ ID NO 116
<211> LENGTH: 517
<212> TYPE: PRT
<213> ORGANISM: artificial sequence
<220> FEATURE:
<223> OTHER INFORMATION: scFv-hFc

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Tyr Cys Gln Gln Ala Phe Asp Leu Ile Thr
                85                  90                  95

Phe Gly Gly Gly Thr Lys Val Glu Ile Lys Gly Ser Thr Ser Gly Ser
            100                 105                 110

Gly Lys Pro Gly Ser Gly Glu Gly Ser Thr Lys Gly Gln Val Gln Leu
        115                 120                 125

Val Gln Ser Gly Ala Glu Val Lys Lys Pro Gly Ser Ser Val Lys Val
    130                 135                 140

Ser Cys Lys Ala Ser Gly Gly Thr Phe Ser Asn Tyr Ala Ile Ser Trp
145                 150                 155                 160

Val Arg Gln Ala Pro Gly Gln Gly Leu Glu Trp Met Gly Gly Ile Ile
                165                 170                 175

Pro Ile Phe Gly Thr Ala Asn Tyr Ala Gln Lys Phe Gln Gly Arg Val
            180                 185                 190

Thr Ile Thr Ala Asp Glu Ser Thr Ser Thr Ala Tyr Met Glu Leu Ser
        195                 200                 205

Ser Leu Arg Ser Glu Asp Thr Ala Val Tyr Tyr Cys Ala Arg Gly Arg
    210                 215                 220

Gly Tyr Tyr Ser Ser Trp Leu Phe Asp Ile Trp Gly Gln Gly Thr Met
225                 230                 235                 240

Val Thr Val Ser Ser Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Asp Lys Thr His Thr Cys Pro Pro Cys Pro Ala Pro Glu Leu
290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
                325                 330                 335

Ser His Glu Asp Pro Glu Val Lys Phe Asn Trp Tyr Val Asp Gly Val
            340                 345                 350

Glu Val His Asn Ala Lys Thr Lys Pro Arg Glu Glu Gln Tyr Asn Ser
        355                 360                 365

Thr Tyr Arg Val Val Ser Val Leu Thr Val Leu His Gln Asp Trp Leu
    370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
                405                 410                 415

Gln Val Tyr Thr Leu Pro Pro Ser Arg Asp Glu Leu Thr Lys Asn Gln
            420                 425                 430

Val Ser Leu Thr Cys Leu Val Lys Gly Phe Tyr Pro Ser Asp Ile Ala
        435                 440                 445

Val Glu Trp Glu Ser Asn Gly Gln Pro Glu Asn Asn Tyr Lys Thr Thr
    450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
                485                 490                 495
```

Val Met His Glu Ala Leu His Asn His Tyr Thr Gln Lys Ser Leu Ser
            500                 505                 510

Leu Ser Pro Gly Lys
        515

<210> SEQ ID NO 117
<211> LENGTH: 244
<212> TYPE: PRT
<213> ORGANISM: artificial sequence
<220> FEATURE:
<223> OTHER INFORMATION: scFv

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Ala Ser Ala Pro Ile
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Leu Gln
        115                 120                 125

Leu Gln Glu Ser Gly Pro Gly Leu Val Lys Pro Ser Glu Thr Leu Ser
    130                 135                 140

Leu Thr Cys Thr Val Ser Gly Gly Ser Ile Ser Ser Ser Ser Tyr Tyr
145                 150                 155                 160

Trp Gly Trp Ile Arg Gln Pro Pro Gly Lys Gly Leu Glu Trp Ile Gly
                165                 170                 175

Ser Ile Ser Tyr Ser Gly Ser Thr Tyr Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Arg
    210                 215                 220

Asp Arg Gly Asp Thr Ile Leu Asp Val Trp Gly Gln Gly Thr Met Val
225                 230                 235                 240

Thr Val Ser Ser

<210> SEQ ID NO 118
<211> LENGTH: 732
<212> TYPE: DNA
<213> ORGANISM: artificial sequence
<220> FEATURE:
<223> OTHER INFORMATION: scFv DNA

<400> SEQUENCE: 118
gacatccaga tgacccagtc tccatcctcc ctgtctgcat ctgtaggaga cagagtcacc        60
atcacttgcc gggcaagtca gagcattaac agctatttaa attggtatca gcagaaacca      120
gggaaagccc ctaagctcct gatctatgct gcatccagtt tgcaaagtgg ggtcccatca      180

-continued

```
aggttcagtg gcagtggatc tgggacagat ttcactctca ccatcagcag tctgcaacct    240
gaagattttg caacttacta ctgtcagcaa aaagccagtg cccctatcac ttttggcgga    300
gggaccaagg ttgagatcaa aggcagcacc agcggctccg gcaagcctgg ctctggcgag    360
ggcagcacaa agggacagct gcagctgcag gagtcgggcc caggactggt gaagccttcg    420
gagaccctgt ccctcacctg cactgtctct ggtggctcca tcagcagtag tagttactac    480
tggggctgga tccgccagcc cccagggaag gggctggagt ggattgggag tatctcctat    540
agtgggagca cctactacaa cccgtccctc aagagtcgag tcaccatatc cgtggacacg    600
tccaagaacc agttctccct gaagctgagt tctgtgaccg ccgcagacac ggcggtgtac    660
tactgcgcca gggatcgtgg agacaccata ctagacgtat ggggtcaggg tacaatggtc    720
accgtctcct ca                                                        732
```

<210> SEQ ID NO 119
<211> LENGTH: 516
<212> TYPE: PRT
<213> ORGANISM: artificial sequence
<220> FEATURE:
<223> OTHER INFORMATION: scFv-hFc

<400> SEQUENCE: 119

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Ala Ser Ala Pro Ile
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Leu Gln
        115                 120                 125

Leu Gln Glu Ser Gly Pro Gly Leu Val Lys Pro Ser Glu Thr Leu Ser
    130                 135                 140

Leu Thr Cys Thr Val Ser Gly Gly Ser Ile Ser Ser Ser Tyr Tyr
145                 150                 155                 160

Trp Gly Trp Ile Arg Gln Pro Pro Gly Lys Gly Leu Glu Trp Ile Gly
                165                 170                 175

Ser Ile Ser Tyr Ser Gly Ser Thr Tyr Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Arg
    210                 215                 220

Asp Arg Gly Asp Thr Ile Leu Asp Val Trp Gly Gln Gly Thr Met Val
225                 230                 235                 240

Thr Val Ser Ser Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
```

```
            260                 265                 270
Pro Ala Ala Gly Gly Ala Val His Thr Arg Gly Leu Asp Phe Ala Cys
        275                 280                 285

Asp Asp Lys Thr His Thr Cys Pro Pro Cys Pro Ala Pro Glu Leu Leu
        290                 295                 300

Gly Gly Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Lys Phe Asn Trp Tyr Val Asp Gly Val Glu
            340                 345                 350

Val His Asn Ala Lys Thr Lys Pro Arg Glu Glu Gln Tyr Asn Ser Thr
        355                 360                 365

Tyr Arg Val Val Ser Val Leu Thr Val Leu His Gln Asp Trp Leu Asn
    370                 375                 380

Gly Lys Glu Tyr Lys Cys Lys Val Ser Asn Lys Ala Leu Pro Ala Pro
385                 390                 395                 400

Ile Glu Lys Thr Ile Ser Lys Ala Lys Gly Gln Pro Arg Glu Pro Gln
                405                 410                 415

Val Tyr Thr Leu Pro Pro Ser Arg Asp Glu Leu Thr Lys Asn Gln Val
            420                 425                 430

Ser Leu Thr Cys Leu Val Lys Gly Phe Tyr Pro Ser Asp Ile Ala Val
        435                 440                 445

Glu Trp Glu Ser Asn Gly Gln Pro Glu Asn Asn Tyr Lys Thr Thr Pro
    450                 455                 460

Pro Val Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
            500                 505                 510

Ser Pro Gly Lys
        515

<210> SEQ ID NO 120
<211> LENGTH: 246
<212> TYPE: PRT
<213> ORGANISM: artificial sequence
<220> FEATURE:
<223> OTHER INFORMATION: scFv

<400> SEQUENCE: 120

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Leu Ser Leu Pro Ile
                85                  90                  95

Thr Phe Gly Gly Gly Thr Lys Val Glu Ile Lys Gly Ser Thr Ser Gly
```

```
            100                 105                 110
Ser Gly Lys Pro Gly Ser Gly Glu Gly Ser Thr Lys Gly Gln Ile Thr
            115                 120                 125

Leu Lys Glu Ser Gly Pro Thr Leu Val Lys Pro Thr Gln Thr Leu Thr
            130                 135                 140

Leu Thr Cys Thr Phe Ser Gly Phe Ser Leu Ser Thr Ser Gly Val Gly
145                 150                 155                 160

Val Gly Trp Ile Arg Gln Pro Pro Gly Lys Ala Leu Glu Trp Leu Ala
                165                 170                 175

Leu Ile Tyr Trp Asn Asp Glu Lys Arg Tyr Ser Pro Ser Leu Lys Ser
            180                 185                 190

Arg Leu Thr Ile Thr Lys Asp Thr Ser Lys Asn Gln Val Val Leu Thr
            195                 200                 205

Met Thr Asn Met Asp Pro Val Asp Thr Ala Val Tyr Tyr Cys Ala Arg
            210                 215                 220

Asp Pro Gly Glu Gln Leu Gln Val Phe Asp Tyr Trp Gly Gln Gly Thr
225                 230                 235                 240

Leu Val Thr Val Ser Ser
                245

<210> SEQ ID NO 121
<211> LENGTH: 738
<212> TYPE: DNA
<213> ORGANISM: artificial sequence
<220> FEATURE:
<223> OTHER INFORMATION: scFv DNA

<400> SEQUENCE: 121
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ctgtcagcag acactcagtc ccctatcac ttttggcgga     300 gggaccaagg ttgagatcaa aggcagcacc agcggctccg gcaagcctgg ctctggcgag     360
ggcagcacaa agggacagat caccttgaag gagtctggtc ctacgctggt gaaacccaca     420
cagaccctca cgctgacctg cacctttctct gggttctcac tcagcactag tggagtgggt     480
gtgggctgga tccgtcagcc cccaggaaag gccctggagt ggcttgcact catttattgg     540
aatgatgaaa agcgctacag cccatctctg aagagcaggc tcaccatcac caaggacacc     600
tccaaaaacc aggtggtcct tacaatgacc aacatggacc ctgtggacac ggcggtgtac     660
tactgcgcca gagatccagg agagcaacta caggttttcg attactgggg acagggtaca     720
ttggtcaccg tctcctca                                                   738

<210> SEQ ID NO 122
<211> LENGTH: 518
<212> TYPE: PRT
<213> ORGANISM: artificial sequence
<220> FEATURE:
<223> OTHER INFORMATION: scFv-hFc

<400> SEQUENCE: 122

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
```

```
                20                  25                  30
Leu Ala Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Leu Ser Leu Pro Ile
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Ile Thr
        115                 120                 125

Leu Lys Glu Ser Gly Pro Thr Leu Val Lys Pro Thr Gln Thr Leu Thr
            130                 135                 140

Leu Thr Cys Thr Phe Ser Gly Phe Ser Leu Ser Thr Ser Gly Val Gly
145                 150                 155                 160

Val Gly Trp Ile Arg Gln Pro Pro Gly Lys Ala Leu Glu Trp Leu Ala
                165                 170                 175

Leu Ile Tyr Trp Asn Asp Glu Lys Arg Tyr Ser Pro Ser Leu Lys Ser
            180                 185                 190

Arg Leu Thr Ile Thr Lys Asp Thr Ser Lys Asn Gln Val Val Leu Thr
        195                 200                 205

Met Thr Asn Met Asp Pro Val Asp Thr Ala Val Tyr Tyr Cys Ala Arg
    210                 215                 220

Asp Pro Gly Glu Gln Leu Gln Val Phe Asp Tyr Trp Gly Gln Gly Thr
225                 230                 235                 240

Leu Val Thr Val Ser Ser Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Asp Lys Thr His Thr Cys Pro Pro Cys Pro Ala Pro Glu
    290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
            340                 345                 350

Val Glu Val His Asn Ala Lys Thr Lys Pro Arg Glu Glu Gln Tyr Asn
        355                 360                 365

Ser Thr Tyr Arg Val Val Ser Val Leu Thr Val Leu His Gln Asp Trp
    370                 375                 380

Leu Asn Gly Lys Glu Tyr Lys Cys Lys Val Ser Asn Lys Ala Leu Pro
385                 390                 395                 400

Ala Pro Ile Glu Lys Thr Ile Ser Lys Ala Lys Gly Gln Pro Arg Glu
                405                 410                 415

Pro Gln Val Tyr Thr Leu Pro Pro Ser Arg Asp Glu Leu Thr Lys Asn
            420                 425                 430

Gln Val Ser Leu Thr Cys Leu Val Lys Gly Phe Tyr Pro Ser Asp Ile
        435                 440                 445
```

Ala Val Glu Trp Glu Ser Asn Gly Gln Pro Glu Asn Tyr Lys Thr
    450                 455                 460

Thr Pro Pro Val Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
            500                 505                 510

Ser Leu Ser Pro Gly Lys
        515

<210> SEQ ID NO 123
<211> LENGTH: 243
<212> TYPE: PRT
<213> ORGANISM: artificial sequence
<220> FEATURE:
<223> OTHER INFORMATION: scFv

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Asp Leu Leu Thr
                85                  90                  95

Phe Gly Gly Gly Thr Lys Val Glu Ile Lys Gly Ser Thr Ser Gly Ser
            100                 105                 110

Gly Lys Pro Gly Ser Gly Glu Gly Ser Thr Lys Gly Gln Leu Gln Leu
        115                 120                 125

Gln Glu Ser Gly Pro Gly Leu Val Lys Pro Ser Glu Thr Leu Ser Leu
    130                 135                 140

Thr Cys Thr Val Ser Gly Gly Ser Ile Ser Ser Ser Ser Tyr Tyr Trp
145                 150                 155                 160

Gly Trp Ile Arg Gln Pro Pro Gly Lys Gly Leu Glu Trp Ile Gly Ser
                165                 170                 175

Ile Ser Tyr Ser Gly Ser Thr Tyr Tyr Asn Pro Ser Leu Lys Ser Arg
            180                 185                 190

Val Thr Ile Ser Val Asp Thr Ser Lys Asn Gln Phe Ser Leu Lys Leu
        195                 200                 205

Ser Ser Val Thr Ala Ala Asp Thr Ala Val Tyr Tyr Cys Ala Arg Asp
    210                 215                 220

Arg Gly Asp Thr Ile Leu Asp Val Trp Gly Gln Gly Thr Met Val Thr
225                 230                 235                 240

Val Ser Ser

<210> SEQ ID NO 124
<211> LENGTH: 729
<212> TYPE: DNA
<213> ORGANISM: artificial sequence
<220> FEATURE:

<223> OTHER INFORMATION: scFv DNA

<400> SEQUENCE: 124

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa aaatacgacc tcctcacttt tggcggaggg     300
accaaggttg agatcaaagg cagcaccagc ggctccggca agcctggctc tggcgagggc     360
agcacaaagg gacagctgca gctgcaggag tcgggcccag gactggtgaa gccttcggag     420
accctgtccc tcacctgcac tgtctctggt ggctccatca gcagtagtag ttactactgg     480
ggctggatcc gccagccccc agggaagggg ctggagtgga ttgggagtat ctcctatagt     540
gggagcacct actacaaccc gtccctcaag agtcgagtca ccatatccgt agacacgtcc     600
aagaaccagt tctccctgaa gctgagttct gtgaccgccg cagacacggc ggtgtactac     660
tgcgccagag atcgtggaga caccatacta gacgtatggg gtcagggtac aatggtcacc     720
gtctcctca                                                             729
```

<210> SEQ ID NO 125
<211> LENGTH: 515
<212> TYPE: PRT
<213> ORGANISM: artificial sequence
<220> FEATURE:
<223> OTHER INFORMATION: scFv-hFc

<400> SEQUENCE: 125

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Asp Leu Leu Thr
                85                  90                  95

Phe Gly Gly Gly Thr Lys Val Glu Ile Lys Gly Ser Thr Ser Gly Ser
            100                 105                 110

Gly Lys Pro Gly Ser Gly Glu Gly Ser Thr Lys Gly Gln Leu Gln Leu
        115                 120                 125

Gln Glu Ser Gly Pro Gly Leu Val Lys Pro Ser Glu Thr Leu Ser Leu
    130                 135                 140

Thr Cys Thr Val Ser Gly Gly Ser Ile Ser Ser Ser Ser Tyr Tyr Trp
145                 150                 155                 160

Gly Trp Ile Arg Gln Pro Pro Gly Lys Gly Leu Glu Trp Ile Gly Ser
                165                 170                 175

Ile Ser Tyr Ser Gly Ser Thr Tyr Tyr Asn Pro Ser Leu Lys Ser Arg
            180                 185                 190

Val Thr Ile Ser Val Asp Thr Ser Lys Asn Gln Phe Ser Leu Lys Leu
        195                 200                 205
```

Ser Ser Val Thr Ala Ala Asp Thr Ala Val Tyr Tyr Cys Ala Arg Asp
210                 215                 220

Arg Gly Asp Thr Ile Leu Asp Val Trp Gly Gln Gly Thr Met Val Thr
225                 230                 235                 240

Val Ser Ser Thr Thr Thr Pro Ala Pro Arg Pro Pro Thr Pro Ala Pro
            245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
            275                 280                 285

Asp Lys Thr His Thr Cys Pro Pro Cys Pro Ala Pro Glu Leu Leu Gly
290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
            325                 330                 335

Glu Asp Pro Glu Val Lys Phe Asn Trp Tyr Val Asp Gly Val Glu Val
            340                 345                 350

His Asn Ala Lys Thr Lys Pro Arg Glu Glu Gln Tyr Asn Ser Thr Tyr
            355                 360                 365

Arg Val Val Ser Val Leu Thr Val Leu His Gln Asp Trp Leu Asn Gly
370                 375                 380

Lys Glu Tyr Lys Cys Lys Val Ser Asn Lys Ala Leu Pro Ala Pro Ile
385                 390                 395                 400

Glu Lys Thr Ile Ser Lys Ala Lys Gly Gln Pro Arg Glu Pro Gln Val
            405                 410                 415

Tyr Thr Leu Pro Pro Ser Arg Asp Glu Leu Thr Lys Asn Gln Val Ser
            420                 425                 430

Leu Thr Cys Leu Val Lys Gly Phe Tyr Pro Ser Asp Ile Ala Val Glu
            435                 440                 445

Trp Glu Ser Asn Gly Gln Pro Glu Asn Asn Tyr Lys Thr Thr Pro Pro
450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
            485                 490                 495

His Glu Ala Leu His Asn His Tyr Thr Gln Lys Ser Leu Ser Leu Ser
            500                 505                 510

Pro Gly Lys
        515

<210> SEQ ID NO 126
<211> LENGTH: 243
<212> TYPE: PRT
<213> ORGANISM: artificial sequence
<220> FEATURE:
<223> OTHER INFORMATION: scFv

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

| | | | | | | | | | | | |
|---|---|---|---|---|---|---|---|---|---|---|---|
|Tyr|Ala|Ser|Ser|Leu|Gln|Ser|Gly|Val|Pro|Ser|Arg|Phe|Ser|Gly|
| |50| | | |55| | | |60| | |

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Phe Asp Ile Thr
                85                  90                  95

Phe Gly Gly Gly Thr Lys Val Glu Ile Lys Gly Ser Thr Ser Gly Ser
            100                 105                 110

Gly Lys Pro Gly Ser Gly Glu Gly Ser Thr Lys Gly Gln Leu Gln Leu
        115                 120                 125

Gln Glu Ser Gly Pro Gly Leu Val Lys Pro Ser Glu Thr Leu Ser Leu
130                 135                 140

Thr Cys Thr Val Ser Gly Gly Ser Ile Ser Ser Ser Ser Tyr Tyr Trp
145                 150                 155                 160

Gly Trp Ile Arg Gln Pro Pro Gly Lys Gly Leu Glu Trp Ile Gly Ser
                165                 170                 175

Ile Ser Tyr Ser Gly Ser Thr Tyr Tyr Asn Pro Ser Leu Lys Ser Arg
            180                 185                 190

Val Thr Ile Ser Val Asp Thr Ser Lys Asn Gln Phe Ser Leu Lys Leu
        195                 200                 205

Ser Ser Val Thr Ala Ala Asp Thr Ala Val Tyr Tyr Cys Ala Arg Asp
210                 215                 220

Arg Gly Asp Thr Ile Leu Asp Val Trp Gly Gln Gly Thr Met Val Thr
225                 230                 235                 240

Val Ser Ser

```
<210> SEQ ID NO 127
<211> LENGTH: 729
<212> TYPE: DNA
<213> ORGANISM: artificial sequence
<220> FEATURE:
<223> OTHER INFORMATION: scFv DNA

<400> SEQUENCE: 127
gacatccaga tgacccagtc tccatcctcc ctgtctgcat ctgtaggaga cagagtcacc     60
atcacttgcc gggcaagtca gagcattagc agatatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcaa aaatacttcg acatcacttt tggcggaggg    300
accaaggttg agatcaaagg cagcaccagc ggctccggca gcctggctc tggcgagggc     360 agcacaaagg gacagctgca gctgcaggag tcgggcccag gactggtgaa gccttcggag    420
accctgtccc tcacctgcac tgtctctggt ggctccatca gcagtagtag ttactactgg    480
ggctggatcc gccagccccc agggaagggg ctggagtgga ttgggagtat ctcctatagt    540
gggagcacct actacaaccc gtccctcaag agtcgagtca ccatatccgt agacacgtcc    600
aagaaccagt tctccctgaa gctgagttct gtgaccgccg cagacacggc ggtgtactac    660
tgcgccagag atcgtggaga caccatacta gacgtatggg gtcagggtac aatggtcacc    720
gtctcctca                                                            729

<210> SEQ ID NO 128
<211> LENGTH: 515
<212> TYPE: PRT
<213> ORGANISM: artificial sequence
```

<220> FEATURE:
<223> OTHER INFORMATION: scFv-hFc

<400> SEQUENCE: 128

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Phe Asp Ile Thr
                85                  90                  95

Phe Gly Gly Gly Thr Lys Val Glu Ile Lys Gly Ser Thr Ser Gly Ser
            100                 105                 110

Gly Lys Pro Gly Ser Gly Glu Gly Ser Thr Lys Gly Gln Leu Gln Leu
        115                 120                 125

Gln Glu Ser Gly Pro Gly Leu Val Lys Pro Ser Glu Thr Leu Ser Leu
130                 135                 140

Thr Cys Thr Val Ser Gly Gly Ser Ile Ser Ser Ser Ser Tyr Tyr Trp
145                 150                 155                 160

Gly Trp Ile Arg Gln Pro Pro Gly Lys Gly Leu Glu Trp Ile Gly Ser
                165                 170                 175

Ile Ser Tyr Ser Gly Ser Thr Tyr Tyr Asn Pro Ser Leu Lys Ser Arg
            180                 185                 190

Val Thr Ile Ser Val Asp Thr Ser Lys Asn Gln Phe Ser Leu Lys Leu
        195                 200                 205

Ser Ser Val Thr Ala Ala Asp Thr Ala Val Tyr Tyr Cys Ala Arg Asp
    210                 215                 220

Arg Gly Asp Thr Ile Leu Asp Val Trp Gly Gln Gly Thr Met Val Thr
225                 230                 235                 240

Val Ser Ser Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Asp Lys Thr His Thr Cys Pro Pro Cys Pro Ala Pro Glu Leu Leu Gly
290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Lys Phe Asn Trp Tyr Val Asp Gly Val Glu Val
            340                 345                 350

His Asn Ala Lys Thr Lys Pro Arg Glu Glu Gln Tyr Asn Ser Thr Tyr
        355                 360                 365

Arg Val Val Ser Val Leu Thr Val Leu His Gln Asp Trp Leu Asn Gly
    370                 375                 380

Lys Glu Tyr Lys Cys Lys Val Ser Asn Lys Ala Leu Pro Ala Pro Ile
385                 390                 395                 400
```

Glu Lys Thr Ile Ser Lys Ala Lys Gly Gln Pro Arg Glu Pro Gln Val
            405                 410                 415

Tyr Thr Leu Pro Pro Ser Arg Asp Glu Leu Thr Lys Asn Gln Val Ser
        420                 425                 430

Leu Thr Cys Leu Val Lys Gly Phe Tyr Pro Ser Asp Ile Ala Val Glu
    435                 440                 445

Trp Glu Ser Asn Gly Gln Pro Glu Asn Asn Tyr Lys Thr Thr Pro Pro
450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
            500                 505                 510

Pro Gly Lys
        515

<210> SEQ ID NO 129
<211> LENGTH: 246
<212> TYPE: PRT
<213> ORGANISM: artificial sequence
<220> FEATURE:
<223> OTHER INFORMATION: scFv

<400> SEQUENCE: 129

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Val Gln Leu Val Gln Ser Gly Ser Glu Leu Lys Lys Pro Gly
    130                 135                 140

Ala Ser Val Lys Val Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205

Tyr Leu Gln Ile Ser Ser Leu Lys Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

Leu Val Thr Val Ser Ser
                245

<210> SEQ ID NO 130
<211> LENGTH: 738
<212> TYPE: DNA
<213> ORGANISM: artificial sequence
<220> FEATURE:
<223> OTHER INFORMATION: scFv DNA

<400> SEQUENCE: 130

```
gacatcgtgc tgacacagag ccctgccagc ctggccgtga gcctgggaga aagggccacc      60
atcaactgca gggcctccga aagcgtgagc gtgatcggcg cccacctgat ccactggtat     120
cagcagaagc ccggccagcc tcccaagctg ctgatctacc tggccagcaa cctggaaacc     180
ggcgtgcctg ccaggtttag cgggagcggc agcggcaccg atttcaccct gaccatcagc     240
agcctgcagg ccgaggacgc tgccatctac tactgcctgc agtccaggat cttccccagg     300
accttcggcc agggcaccaa gctggagatc aaggcagca ccagcggcag cggcaagccc      360
ggctccggag agggcagcac caagggccag gtgcagctgg tgcagagcgg cagcgagctg     420
aagaaacccg gcgccagcgt gaaggtgagc tgcaaggcca gcggctacac cttcaccgac     480
tacagcatca actgggtgag gcaggcccct ggacagggac tggagtggat gggctggatc     540
aacaccgaga ccagggagcc cgcctacgcc tacgacttca ggggcaggtt cgtgttcagc     600
ctggacacca gcgtgagcac cgcctacctg cagatcagca gcctgaaggc cgaggacacc     660
gccgtgtact actgcgccag ggactacagc tacgccatgg actactgggg ccagggcacc     720
ctggtgacag tgtccagc                                                    738
```

<210> SEQ ID NO 131
<211> LENGTH: 521
<212> TYPE: PRT
<213> ORGANISM: artificial sequence
<220> FEATURE:
<223> OTHER INFORMATION: scFv-hFc

<400> SEQUENCE: 131

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Val Gln Leu Val Gln Ser Gly Ser Glu Leu Lys Lys Pro Gly
    130                 135                 140

Ala Ser Val Lys Val Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205

Tyr Leu Gln Ile Ser Ser Leu Lys Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

Leu Val Thr Val Ser Ser Ala Ala Thr Thr Thr Pro Ala Pro Arg
                245                 250                 255

Pro Pro Thr Pro Ala Pro Thr Ile Ala Ser Gln Pro Leu Ser Leu Arg
                260                 265                 270

Pro Glu Ala Cys Arg Pro Ala Ala Gly Gly Ala Val His Thr Arg Gly
                275                 280                 285

Leu Asp Phe Ala Cys Asp Asp Lys Thr His Thr Cys Pro Pro Cys Pro
    290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
                340                 345                 350

Val Asp Gly Val Glu Val His Asn Ala Lys Thr Lys Pro Arg Glu Glu
            355                 360                 365

Gln Tyr Asn Ser Thr Tyr Arg Val Val Ser Val Leu Thr Val Leu His
    370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Asp Glu Leu
                420                 425                 430

Thr Lys Asn Gln Val Ser Leu Thr Cys Leu Val Lys Gly Phe Tyr Pro
    435                 440                 445

Ser Asp Ile Ala Val Glu Trp Glu Ser Asn Gly Gln Pro Glu Asn Asn
450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
                500                 505                 510

Lys Ser Leu Ser Leu Ser Pro Gly Lys
                515                 520

<210> SEQ ID NO 132
<211> LENGTH: 227
<212> TYPE: PRT
<213> ORGANISM: artificial sequence
<220> FEATURE:
<223> OTHER INFORMATION: human IgG1 Fc

<400> SEQUENCE: 132

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 133
<211> LENGTH: 20
<212> TYPE: PRT
<213> ORGANISM: artificial sequence
<220> FEATURE:
<223> OTHER INFORMATION: murine Ig?? signal peptide

<400> SEQUENCE: 133

Met Glu Thr Asp Thr Leu Leu Leu Trp Val Leu Leu Leu Trp Val Pro
1               5                   10                  15

Gly Ser Thr Gly
            20

<210> SEQ ID NO 134
<211> LENGTH: 60
<212> TYPE: DNA
<213> ORGANISM: artificial sequence
<220> FEATURE:
<223> OTHER INFORMATION: DNA encoding murine Ig?? signal peptide

<400> SEQUENCE: 134
atggagaccg acaccctgct gctctgggtc ctgctgctgt gggtgcccgg atccacagga     60

<210> SEQ ID NO 135
<211> LENGTH: 516
<212> TYPE: PRT
<213> ORGANISM: artificial sequence
```

```
<220> FEATURE:
<223> OTHER INFORMATION: ADI-34819 scFv-hFc

<400> SEQUENCE: 135

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser His Val Arg
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Gln Leu Gln
        115                 120                 125

Leu Gln Glu Ser Gly Pro Gly Leu Val Lys Pro Ser Glu Thr Leu Ser
130                 135                 140

Leu Thr Cys Thr Val Ser Gly Gly Ser Ile Ser Ser Ser Ser Tyr Tyr
145                 150                 155                 160

Trp Gly Trp Ile Arg Gln Pro Pro Gly Lys Gly Leu Glu Trp Ile Gly
                165                 170                 175

Ser Ile Ser Tyr Ser Gly Ser Thr Tyr Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Arg
    210                 215                 220

Asp Arg Gly Asp Thr Ile Leu Asp Val Trp Gly Gln Gly Thr Met Val
225                 230                 235                 240

Thr Val Ser Ser Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Asp Lys Thr His Thr Cys Pro Pro Cys Pro Ala Pro Glu Leu Leu
290                 295                 300

Gly Gly Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Lys Phe Asn Trp Tyr Val Asp Gly Val Glu
            340                 345                 350

Val His Asn Ala Lys Thr Lys Pro Arg Glu Glu Gln Tyr Asn Ser Thr
        355                 360                 365

Tyr Arg Val Val Ser Val Leu Thr Val Leu His Gln Asp Trp Leu Asn
    370                 375                 380

Gly Lys Glu Tyr Lys Cys Lys Val Ser Asn Lys Ala Leu Pro Ala Pro
385                 390                 395                 400
```

```
Ile Glu Lys Thr Ile Ser Lys Ala Lys Gly Gln Pro Arg Glu Pro Gln
                405                 410                 415

Val Tyr Thr Leu Pro Pro Ser Arg Asp Glu Leu Thr Lys Asn Gln Val
            420                 425                 430

Ser Leu Thr Cys Leu Val Lys Gly Phe Tyr Pro Ser Asp Ile Ala Val
        435                 440                 445

Glu Trp Glu Ser Asn Gly Gln Pro Glu Asn Asn Tyr Lys Thr Thr Pro
    450                 455                 460

Pro Val Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
            500                 505                 510

Ser Pro Gly Lys
        515
```

FULLY HUMANIZED ANTI-B CELL MATURATION ANTIGEN (BCMA) SINGLE-CHAIN ANTIBODY AND USE THEREOF

TECHNICAL FIELD

The invention relates to a novel antibody and an antibody fragment, particularly a single-chain antibody (e.g., scFv), that specifically bind to B-cell maturation antigen (BCMA). The invention further relates to nucleic acids encoding the antibodies and the antibody fragments, vectors, and host cells expressing the nucleic acids. Furthermore, the invention also relates to compositions comprising the antibodies described herein, and their use in treatment and diagnosis.

BACKGROUND

B-cell maturation antigen (BCMA), also known as CD269 or TNFRSF17, is a member of the tumor necrosis factor receptor superfamily. BCMA is a type III transmembrane protein with a cysteine-rich domain (CRD) forming a ligand binding motif in its extracellular domain (ECD), which is distinctive to TNFR superfamily. BCMA is functionally related to TNFR superfamily members, transmembrane activator and CMAL interactor (TACI) and BAFF receptors (BAFF-R). BCMA demonstrates certain similarity to TACI in CRD at the N-terminus of the transmembrane domain. Furthermore, human BCMA has approximately 65% and 85% amino acid sequence identity to murine and cynomolgus BCMA on the extracellular domain (ECD) respectively.

Studies have shown that BCMA can bind to B cell activating factor (BAFF) receptors and a proliferation-inducing ligands (APRIL), promoting survival of B cells at different developmental stages. Abnormal signaling can promote abnormal proliferation of B cells, leading to autoimmune diseases and tumor formation. See Rickert et al., Immunological Reviews 2011, Vol. 244: 115-133.

APRIL, also known as G70, is a member of the TNF ligand family. It has been reported in the literature that APRIL is associated with prostate cancer, breast cancer, alzheimer's disease, immune disorder, inflammation and gastrointestinal disorder. See Hahne et al. (1998), T. Exp. Med. 188: 1185-90. Binding of soluble APRIL to BCMA can promote survival of plasma cells and plasmablasts in bone marrow (BM) (see, BLOOD, May 2014, Vol. 123, Issue 20, pp. 3128-3138); whereas binding to TACI may result in T-cell independent antibody response, B-cell regulation, and class-switch recombination (see Vincent et. al., Nature Reviews Rheumatology, 2014, Vol. 10: 365-373).

BAFF is another TNF ligand family member. The binding of BAFF to BCMA can promote the survival of plasma cells. The binding of BAFF to BAFF receptors (BAFF-R) expressed on the surface of B cells, plasmablasts and plasma cells can promote the survival and maturation of immature B cells. Furthermore, BAFF may also bind to TACI, resulting in T-cell independent antibody response, B-cell regulation, and class-switch recombination (see Vincent et. al., Nature Reviews Rheumatology, 2014, Vol. 10: 365-373).

In non-tumor cells, BCMA is predominantly expressed in plasma cell and mature B cell subpopulations. In 60-70% of patients with multiple myeloma (MM), BCMA is also expressed on the surfaces of cancerous plasma cells. Serum BCMA levels are elevated in MM patients, and the elevated levels are correlated with disease status, treatment response, and overall survival. BCMA-deficient mice have normal B cell levels, but significantly shortened plasma cell life cycle. Therefore, BCMA is an ideal target for multiple myeloma immunotherapy.

Single-chain scFv antibody is a small-molecule genetically engineered antibody, and a small-molecule recombinant antibody obtained by connecting (usually via a synthetic linker peptide or a linker) a heavy chain variable region (VH) with a light chain variable region (VL) of a natural antibody at the DNA level by genetic engineering. Compared with an intact antibody molecule, the single-chain scFv antibody has the following advantages: having the variable regions of an intact antibody, thereby retaining the antigen specificity and antigen-binding activity of the original antibody; having no Fc region, and thus weak immunogenicity; small molecular weight, high penetrability, and capability to permeate into tissues that are inaccessible for intact antibodies in radiological imaging diagnosis or treatment; requiring no glycosylation modification for generating a functional antibody molecule, facilitating mass production by a prokaryotic expression system; easy-to-operate and suitable for use as a genetically engineered component in preparing other antigen-specific binding molecules with new properties, such as full-length antibodies, scFv-Fc antibodies, etc.

In view of the effectiveness of BCMA as a therapeutic target in B cell malignancies, particularly multiple myeloma, there is a need in the art for new BCMA-specific binding molecules. The invention satisfies this need by providing fully human single-chain antibodies that bind to BCMA, in particular to BCMA expressed on the surfaces of tumor cells, with high specificity and high affinity, and have mild side effects. The fully human single-chain antibodies disclosed herein are not only suitable for use alone in the diagnosis or treatment of tumors and cancers, but are more advantageously suitable as a genetically engineered component to produce other diagnostic and therapeutic molecules targeting BCMA, such as various forms of antibodies, scFv-Fc, and antibody-based fusions and conjugates.

SUMMARY

The invention provides a fully humanized anti-human-BCMA antibody, a coding gene thereof, and use thereof. Through genetic engineering and yeast display, the inventor found a fully humanized anti-human-BCMA antibody from a human antibody library displayed on the surface of yeast, obtained a variable region gene sequence of the fully humanized antibody, constructed a fully human single-chain scFv antibody and a fusion of the scFv with a human Fc region, and obtained a scFv-hFc recombinant single-chain antibody molecule through expression in mammalian cells and purification. The recombinant single-chain antibody molecule disclosed herein binds to not only free human BCMA with high affinity but also BCMA expressed on cell surface with high affinity.

Accordingly, the invention provides antibodies, particularly single-chain antibodies, that specifically bind to BCMA, nucleic acid molecules encoding the antibodies, and use of the antibodies in treatment and diagnosis.

In one aspect, the invention provides an antibody or an antigen-binding fragment thereof that specifically binds to BCMA, preferably human BCMA protein. In one preferred embodiment, the antibody disclosed herein is a single-chain antibody. In one preferred embodiment, the antibody disclosed herein is a single-chain scFv antibody. In another preferred embodiment, the antibody disclosed herein is an scFv-Fc antibody. In some embodiments, the antibody disclosed herein binds to human BCMA protein with a $K_D$ of about 100 nM to 5 nM, wherein the $K_D$ is measured, for example, by biolayer interferometry (e.g., Fortebio assay). In some embodiments, the antibody disclosed herein binds to human BCMA protein expressed on the cell surfaces with an $EC_{50}$ of about 40 nM to 4 nM, wherein the $EC_{50}$ is measured, for example, by flow cytometry (e.g., FACS). In some embodiments of the invention, provided is use of the anti-BCMA antibodies or the fragments thereof disclosed herein in treating BCMA-associated disorders.

In some embodiments, the antibody disclosed herein comprises a VH region sequence of any one of the antibodies shown in Table 1, or a variant thereof. In some other embodiments, the antibody disclosed herein comprises a VL region sequence of any one of the antibodies shown in Table 1, or a variant thereof. In some other embodiments, the antibody disclosed herein comprises a VH and VL sequence pair of any one of the antibodies shown in Table 1, or a variant thereof. In some other embodiments, the antibody disclosed herein comprises one, two or three CDRs (preferably three CDRs), or variants thereof, of a VH region sequence of any one of the antibodies shown in Table 1. In some other embodiments, the antibody disclosed herein comprises one, two or three CDRs (preferably three CDRs), or variants thereof, of a VL region sequence of any one of the antibodies shown in Table 1. In some embodiments, the antibody disclosed herein comprises 6 CDR region sequences of any one of the antibodies shown in Table 1, or variants thereof. In one embodiment, the CDR sequences of the antibody are the CDR sequences shown in Table 2.

In some embodiments, the antibody disclosed herein is a single-chain scFv antibody. Preferably, the scFv antibody comprises a VH, a VL, and a linker. Preferably, the scFv antibody comprises VL domain-linker-VH domain or VH domain-linker-VL domain from the N terminus to the C terminus.

In some embodiments, the invention also provides an scFv-Fc antibody formed by fusion of a single-chain scFv antibody disclosed herein and a wild type or modified Fc region. In some embodiments, the Fc region of the antibody disclosed herein is low- or non-fucosylated. In some embodiments, the scFv antibody is connected with the Fc region by a hinge region.

In yet another aspect, the invention relates to a fusion and a conjugate based on the antibody disclosed herein, especially the single-chain antibody.

In yet another aspect, the invention relates to a method and a composition for treating B-cell related disorders, wherein an effective amount of the antibody or the antigen-binding fragment thereof, or the fusion or the conjugate disclosed herein is administered to a subject. In some embodiments, the B-cell related disorder is selected from B-cell malignancies, plasmocytic malignancies and autoimmune diseases, and preferably selected from multiple myeloma, non-Hodgkin's lymphoma, B-cell proliferation with indeterminate malignant potential, lymphomatoid granulomatosis, post-transplant lymphoproliferative disorder, immunomodulatory disorder, rheumatoid arthritis, myasthenia gravis, idiopathic thrombocytopenic purpura, antiphospholipid syndrome, Chagas disease, Graves disease, Wegener's granulomatosis, polyarteritis nodosa, Sjogren's syndrome, pemphigus vulgaris, scleroderma, multiple sclerosis, ANCA-associated vasculitis, Goodpasture syndrome, Kawasaki disease, autoimmune hemolytic anemia, acute glomerulonephritis, heavy chain disease, primary or immune cell-associated amyloidosis, and monoclonal gammopathy of undetermined significance. In some preferred embodiments, the B-cell related disorder refers to B-cell malignancy, preferably multiple myeloma (MM) or non-hodgkin's lymphoma (NHL). In some embodiments, the antibody molecule, the fusion, or the conjugate disclosed herein is used in combination with other therapeutic agents.

In yet another aspect, the invention relates to a method and kit for detecting BCMA in a sample, wherein the method comprises the steps of (a) contacting the sample with the antibody or the antigen-binding fragment, the fusion or the conjugate thereof disclosed herein; and (b) detecting a complex formed by the antibody or the antigen-binding fragment, the fusion or the conjugate thereof and BCMA protein. In some embodiments, the sample is derived from a patient with multiple myeloma (MM). The detection may be in vitro or in vivo.

BRIEF DESCRIPTION OF DRAWINGS

FIG. 4 shows exemplary CDR sequences of antibodies disclosed herein.

FIG. 5 shows exemplary VH sequences of antibodies disclosed herein.

FIG. 6 shows exemplary VL sequences of antibodies disclosed herein.

FIG. 7 shows exemplary amino acid sequences of human BCMA and extracellular domain (ECD) thereof.

FIG. 8 shows the amino acid and nucleotide sequences of the linkers, the hinge regions, and the Fc region of an exemplary scFv-Fc construct disclosed herein and a reference scFv-Fc construct.

DETAILED DESCRIPTION

Figure 1:
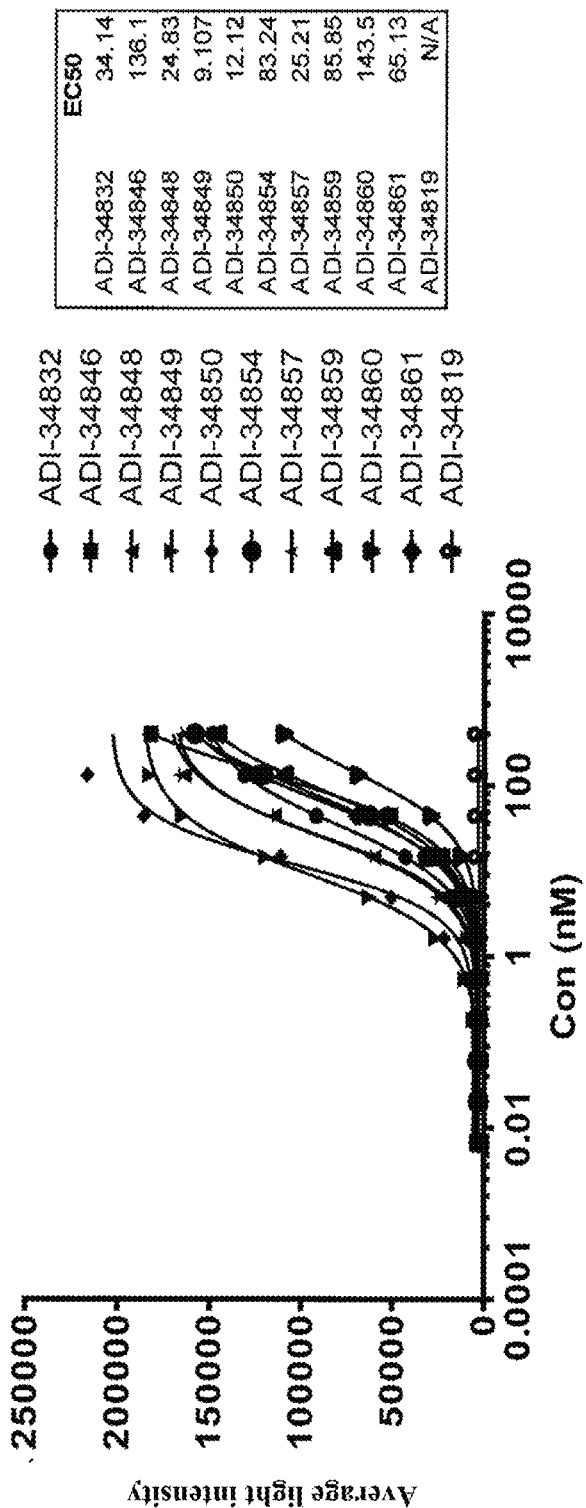
FIG. 1 shows the affinity of exemplary anti-BCMA antibodies disclosed herein screened from a yeast display library with multiple myeloma cell line NCI-H929 as determined by flow cytometry.

Unless otherwise indicated, conventional methods of chemistry, biochemistry, organic chemistry, molecular biology, microbiology, recombinant DNA techniques, genetics, immunology and cell biology that are known in the art will be employed for the implementation of the present invention. Descriptions of such methods can be found, for example, in Sambrook et. al., Molecular Cloning: A Laboratory Manual (3rd edition, 2001); Sambrook et. al., Molecular Cloning: A Laboratory Manual (2nd edition, 1989); Maniatis et. al., Molecular Cloning: A Laboratory Manual (1982); Ausubel et. al., Current Protocols in Molecular Biology (John Wiley and Sons, updated in July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I&II (IRL Press, Oxford, 1985); Anand, Techniques for the Analysis of Complex Genomes, (Academic Press, New York, 1992); Transcription and Translation (B. Hames&S. Higgins, Eds., 1984); Perbal, A Practical Guide to Molecular Cloning (1984); Harlow and Lane, Antibodies, (Cold Spring Harbor Laboratory Press, Cold Spring Harbor, N.Y., 1998) Current Protocols in Immunology Q. E. Coligan, A. M. Kruisbeek, D. H. Margulies, E. M. Shevach and W. Strober, eds., 1991); Annual Review of Immunology; and journals and monographs such as Advances in Immunology.

Definitions

Unless defined otherwise, all technical and scientific terms used herein have the same meaning as commonly understood by those of ordinary skill in the art. For the purposes of the invention, the following terms are defined below.

The term "about" used in combination with a numerical value is intended to encompass the numerical values in a range from a lower limit less than the specified numerical value by 5% to an upper limit greater than the specified numerical value by 5%.

The term "and/or", when used to connect two or more options, should be understood to refer to any one of the options or any two or more of the options.

As used herein, the term "comprise" or "include" is intended to include the described elements, integers or steps, but not to exclude any other elements, integers or steps. The term "comprise" or "include" used herein, unless indicated otherwise, also encompasses the situation where the entirety consists of the described elements, integers or steps. For example, when referring to "comprise" an antibody variable region of a particular sequence, it is also intended to include an antibody variable region consisting of the particular sequence.

As used herein, the term "antigen-binding molecule" refers to a molecule, such as a protein or polypeptide, that comprises an antigen-binding region or antigen-binding portion capable of binding to a target antigen. In the present invention, when the target antigen is B-cell maturation antigen (BCMA), the antigen-binding molecule that binds to BCMA is also referred to as a BCMA-binding molecule. The antigen-binding molecules include, for example, antibodies and antigen-binding fragments thereof, single-chain scFv antibodies, and various scFv-based fusions and conjugates, such as scFv-Fc antibodies. It will be appreciated by those skilled in the art that the antigen-binding portion of an antibody typically comprises amino acid residues from a "complementarity determining region" or "CDR". In some cases, depending on the context, the "BCMA-binding molecule" may be used interchangeably with the "antibody of the invention" or the "anti-BCMA antibody".

As used herein, the term "antibody" refers to a polypeptide comprising at least an immunoglobulin light chain or heavy chain variable region that specifically recognizes and binds to an antigen. The term "antibody" includes a variety of antibody structures, including, but not limited to, monoclonal antibody, polyclonal antibody, single-chain or multi-chain antibodies, monospecific or multispecific antibodies (e.g., bispecific antibodies), fully human or chimeric or humanized antibodies, and full-length antibodies and antibody fragments so long as they exhibit the desired antigen-binding activity.

It will be understood by those of skill in the art that a "whole antibody" (used interchangeably herein with "full-length antibody", "complete antibody" and "intact antibody") comprises at least two heavy chains (Hs) and two light chains (Ls). Each heavy chain consists of a heavy chain variable region (abbreviated herein as VH) and a heavy chain constant region. Each heavy chain constant region consists of 3 domains CH1, CH2 and CH3. Each light chain consists of a light chain variable region (abbreviated herein as VL) and a light chain constant region. Each light chain constant region consists of one domain CL. The variable regions are domains involved in binding of antibodies to their antigens in the heavy or light chains of antibodies. The constant regions are not directly involved in binding of antibodies to antigens, but exhibit a variety of effector functions. The light chains of an antibody can be assigned to one of two types, called kappa (κ) and lambda (λ), based on the amino acid sequence of constant domain thereof. The heavy chains of an antibody can be divided into 5 major types (e.g., IgA, IgD, IgE, IgG, and IgM) depending on the amino acid sequences of heavy chain constant regions thereof, some of which can be further divided into subtypes, e.g., IgG1, IgG2, IgG3, IgG4, IgA1 and IgA2. The heavy chain constant regions corresponding to different antibody types are called α, δ, ε, γ and μ respectively. See, e.g., Fundamental Immunology, Ch. 7 (Paul, w. editions, second edition, Raven Press, N.Y. (1989)) which is incorporated herein by reference in its entirety for all purposes.

The term "antibody fragment" refers to an incomplete antibody molecule comprising a portion of a complete antibody for binding to an antigen to which the complete antibody binds. The antigen-binding fragment may be prepared by recombinant DNA techniques, or by enzymatic or chemical cleavage of the complete antibody. The antigen-binding fragment includes, but is not limited to, an Fab, an scFab, an Fab', an F(ab')$_2$, an Fab'-SH, an Fv, a single-chain Fv fragment, a diabody, a triabody, a tetrabody, a minibody, and a single-domain antibody (sdAb), and a multispecific antibody formed by the antibody fragment. The Fab fragment is a monovalent fragment consisting of VL, VH, CL, and CH1 domains, and can be obtained, for example, by papain digestion of the complete antibody. The light chains (L chains) and heavy chains (H chains) of the Fab can be fused into a single polypeptide chain, i.e., a single-chain Fab (scFab), by means of a linker (see e.g., US20070274985A1). Furthermore, the F(ab')$_2$, a dimer of the Fab', is a bivalent antibody fragment and can be produced by pepsin digestion of the complete antibody below a disulfide bond in a hinge region. The F(ab')$_2$ can be reduced under neutral conditions by disrupting the disulfide bonds in the hinge region and converted to Fab' monomer from the F(ab')$_2$ dimer. The Fab' monomer is essentially an Fab fragment with a hinge region. The Fv fragment consists of the VL and VH domains of a single arm of an antibody. Alternatively, genes independently encoding the two domains VL and VH of the Fv fragment can be linked together through a nucleic acid sequence encoding a linker peptide (linker) by recombinant techniques to form, through recombinant expression, a single-chain Fv in which the VH and VL regions are paired to provide an antigen-binding site. The diabody is an antibody fragment with two antigen-binding sites, which comprises a VL and a VH connected by a short linker in the same polypeptide chain. In the diabody, due to the short linker, the two domains VH and VL on the same chain cannot be paired, but are forced to pair with the complementarity domain on the other chain to form two antigen-binding sites. The diabody can be bivalent or bispecific. More detailed descriptions of the diabody can be found, for example, in EP 404,097; WO 1993/01161; Hudson et. al., Mat. Med. 9:129-134 (2003); and Hollinger et. al., PNAS USA 90:6444-6448 (1993). The triabody, the tetrabody and the minibody are also described in Hudson et. al., Nat. Med. 9:129-134 (2003), and Shao Rongguang et al. (eds.), Antibody Drug Research and Application, People's Medical Publishing House (2013). The single-domain antibody (sdAb) generally refers to an antibody in which a single variable domain (e.g., a heavy chain variable domain (VH) or a light chain variable domain (VL)), a heavy chain variable domain derived from a camelid heavy chain antibody, and a VH-like single domain (v-NAR) derived from fish IgNAR that can bind to an antigen without the need to interact with another variable domain to recognize the target antigen. (More detailed descriptions of the antibody fragment can be also seen in Fundamental Immunology, W. E. Paul eds., Raven Press, N.Y. (1993).

The term "monoclonal antibody" used herein refers to an antibody obtained from a substantially homogeneous population of antibodies, i.e., the antibodies constituting the population are identical and/or bind to same epitopes except for variant antibodies that are typically present in minor amounts (e.g., variant antibodies containing natural mutations or produced during the production of a monoclonal antibody preparation). Monoclonal antibodies can be prepared by a variety of techniques including, but not limited to, hybridoma, recombinant DNA, yeast display, and methods using transgenic animals comprising all or part of human immunoglobulin loci.

The terms "human antibody" and "fully humanized antibody" are used interchangeably herein and refer to an antibody comprising variable regions in which both framework regions and CDR regions are derived from human germline immunoglobulin sequences. Furthermore, if the antibody contains constant regions, the constant regions are also derived from human germline immunoglobulin sequences. The human antibody disclosed herein can include amino acids (e.g., mutations introduced by in-vitro random or site-directed mutagenesis or in-vivo somatic mutation) not encoded by human germline immunoglobulin sequences, for example, in CDRs, particularly in CDR3. However, as used herein, the term "human antibody" is not intended to include antibodies in which the CDR sequences, derived from the germline of other mammalian species (e.g., mice), are grafted into human framework sequences.

As used herein, the term "recombinant human antibody" includes all human antibodies that are prepared, expressed, produced or isolated by recombinant means, e.g., (a) antibodies isolated from transgenic or transchromosomal animals (e.g., mice) using human immunoglobulin genes or from hybridomas prepared from the human immunoglobulin genes; (b) antibodies isolated from host cells, e.g., transfectomas, that transform to express human antibodies; (c) antibodies isolated from recombinant and combinatorial human antibody libraries, e.g., yeast display libraries; and (d) antibodies prepared, expressed, produced or isolated in any other ways including splicing of human immunoglobulin genes to other DNA sequences. These recombinant human antibodies have variable regions in which both framework regions and CDR regions are derived from human germline immunoglobulin sequences. However, in certain embodiments, the recombinant human antibodies can be subjected to in-vitro mutagenesis (or in-vivo somatic mutagenesis in the case of transgenic animals using human Ig sequences), and the amino acid sequences of the VH and VL regions of the resulting recombinant antibodies, although derived from and related to human germline VH and VL sequences, do not naturally occur in a human antibody germline library.

The term "chimeric antibody" refers to an antibody in which the variable region sequences are derived from one species and the constant region sequences are derived from another species, e.g., an antibody in which the variable region sequences are derived from a mouse antibody and the constant region sequences are derived from a human antibody.

The term "humanized antibody" refers to an antibody in which CDR sequences derived from another mammalian species, such as mice, are linked to human framework sequences. Additional framework region modifications can be introduced within the human framework sequences.

An "isolated" antibody is one that has been separated from components of its natural environment. In some embodiments, the antibody is purified to be greater than 95% or 99% in purity as determined, for example, by electrophoresis (e.g., SDS-PAGE, isoelectric focusing (IEF), capillary electrophoresis), or chromatography (e.g., ion exchange or reverse-phase HPLC). A review of methods for assessing antibody purity is described in, e.g., Flatman, S. et al., J. Chrom. B, 848 (2007) 79-87.

An epitope is an antigen region to which an antibody binds. Epitopes can be formed by contiguous amino acids or noncontiguous amino acids juxtaposed by tertiary folding of a protein.

The terms "BCMA" and "B-cell maturation antigen" are used interchangeably and include variants, isoforms, species homologs of human BCMA and analogs that share at least one common epitope with BCMA (e.g., human BCMA). FIG. 7 shows an exemplary human BCMA sequence (SEQ ID NO: 74). BCMA protein can also include fragments of BCMA, such as extracellular domains and fragments of the extracellular domains, e.g., fragments that retain the ability to bind to any antibody disclosed herein.

The term "specifically binds" means that an antibody selectively or preferentially binds to an antigen. If an antibody binds to human BCMA with a $K_D$ of about $5\times10^{-7}$ M or less, about $1\times10^{-7}$ M or less, about $5\times10^{-8}$ M or less, about $1\times10^{-8}$ M or less, about $5\times10^{-9}$ M or less measured by biolayer interferometry, it is the antibody that "specifically binds" to human BCMA.

The "affinity" or "binding affinity" refers to the inherent binding affinity that reflects the interaction between members of a binding pair. The affinity of a molecule X for its partner Y can be generally represented by the equilibrium dissociation constant ($K_D$), which is the ratio of a dissociation rate constant ($k_{dis}$) to an association rate constant ($k_{on}$). The affinity can be measured by common methods known in the art. One particular method for measuring the affinity is the ForteBio kinetic binding assay described herein.

The "antibody that competes for binding" is an antibody that competes against a reference antibody for binding to an antigen such as BCMA, and it blocks the binding of the reference antibody to the antigen (e.g., BCMA) by 50% or more in a competition assay, and conversely, the reference antibody also blocks binding of the antibody to the antigen (e.g., BCMA) by 50% or more in a competition assay. Exemplary competition assays are described in: "Antibodies", Harbor and Lane (Cold Spring Harbor Press, Cold Spring Harbor, N.Y.). The antibody that competes for binding and the reference antibody can bind to the same epitope region, e.g., the same epitope, adjacent epitopes or overlapping epitopes.

The term "Fc region" is used herein to define the C-terminal region of an immunoglobulin heavy chain that contains at least a portion of constant regions. The term includes a Fc-region of native sequence and a variant Fc-region. In one embodiment, a human IgG heavy chain Fc-region extends from Cys226 or from Pro230 of a heavy chain to a carboxyl terminal. However, the C-terminal lysine (Lys447) of the Fc region may or may not be present. Unless otherwise indicated herein, the numbering of amino acid residues in the Fc-region or constant region is based on the EU numbering system, also known as the EU index, as described in Kabat, E. A., et. al., Sequences of Proteins of Immunological Interest, 5th edition, Public Health Service, National Institutes of Health, Bethesda, Md. (1991), NIH Publication 91-3242.

The term "variant" related to the antibody herein refers to an antibody comprising a target antibody region (e.g. a heavy chain variable region, a light chain variable region, a heavy chain CDR region or a light chain CDR region) which has amino acid alterations by virtue of at least one, for example, 1-30, 1-20 or 1-10, e.g., 1, 2, 3, 4 or 5 amino acid substitutions, deletions and/or insertions, wherein the variant substantially retains the biological properties of the antibody molecule prior to alteration. In one aspect, the invention encompasses variants of any of the antibodies described herein. In one embodiment, the antibody variant retains at least 60%, 70%, 80%, 90% or 100% of the biological activity (e.g., antigen-binding capacity) of the antibody prior to alteration. In some embodiments, the alteration does not result in loss of the capability of antibody variants to bind to the antigen, but optionally may confer properties such as increased antigen affinity and different effector functions. It will be appreciated that the heavy or light chain variable regions of the antibody, or the CDR regions of the heavy or light variable regions may be altered individually or in combination. In some embodiments, there are no more than 1, 2, 3, 4, 5, 6, 7, 8, 9, or 10 amino acid alterations in one or more or all of the three heavy chain CDRs. In some embodiments, there are no more than 1, 2, 3, 4, 5, 6, 7, 8, 9 or 10 amino acid alterations in one or more or all of the three light chain CDRs. In some embodiments, there are no more than 1, 2, 3, 4, 5, 6, 7, 8, 9, or 10 amino acid alterations in one or more or all of the six CDRs. Preferably, the amino acid alteration refers to an amino acid substitution, preferably conservative substitution. In some embodiments, the antibody variant has at least 80%, 85%, 90%, 95%, 99% or higher amino acid identity to a parent antibody in target antibody sequence region. For example, in one embodiment, the antibody disclosed herein has at least 80%, 85%, 90%, 91%, 92%, 93%, 94%, 95%, 96%, 97%, 98%, 99% or higher sequence identity to any of the antibodies listed in Table 1 in heavy chain variable region. In yet another embodiment, the antibody disclosed herein has at least 80%, 85%, 90%, 91%, 92%, 93%, 94%, 95%, 96%, 97%, 98%, 99% or higher sequence identity to any of the antibodies listed in Table 1 in light chain variable region. In yet another embodiment, the antibody disclosed herein has at least 80%, 85%, 90%, 91%, 92%, 93%, 94%, 95%, 96%, 97%, 98%, 99% or higher sequence identity to any of the antibodies listed in Table 1 in heavy and light chain variable regions.

As used herein, the term "sequence identity" refers to the degree to which sequences are identical on a nucleotide-by-nucleotide or amino acid-by-amino acid basis in a comparison window. The "percent sequence identity" can be calculated by the following steps: comparing two optimally aligned sequences in a comparison window; determining a number of positions in which nucleic acid bases (e.g., A, T, C, G and I) or amino acid residues (e.g., Ala, Pro, Ser, Thr, Gly, Val, Leu, Ile, Phe, Tyr, Trp, Lys, Arg, His, Asp, Glu, Asn, Gln, Cys, and Met) are the same in the two sequences to yield the number of matched positions; dividing the number of matched positions by the total number of positions in the comparison window (i.e., the window size); and multiplying the result by 100 to yield a percent sequence identity. Optimal alignment for determining the percent sequence identity can be achieved in a variety of ways known in the art, for example, using publicly available computer software such as BLAST™, BLAST-2™, ALIGN™, or Megalign (DNASTAR™) software. Those skilled in the art can determine suitable parameters for alignment of the sequences, including any algorithms necessary to achieve optimal alignment in a full-length sequence range or target sequence region being compared.

Herein, with respect to antibody sequences, the percent amino acid sequence identity is determined by optimally aligning a candidate antibody sequence with a reference antibody sequence, and in one preferred embodiment, optimal alignment is performed according to the Kabat numbering scheme. After alignment, a target antibody region (e.g., the entire heavy or light chain variable region, or a portion thereof such as one or more CDR regions) is compared to the same region of a reference antibody. The percent sequence identity between the target antibody region and the reference antibody region is a percent obtained by the following steps: dividing the number of positions having same amino acids in both target and reference antibody regions by the total number of aligned positions for both regions (gaps are not counted); and multiplying the result by 100. Herein, without specifying the target antibody region, it will be applicable to the alignment over the full length of the reference antibody sequence. In some embodiments, with respect to antibodies, the sequence identity may be achieved throughout the heavy chain variable region and/or the light chain variable region, or the percent sequence identity may be limited to the framework regions only, while the sequences of corresponding CDR regions remain 100% identical.

A. BCMA-binding molecules and compositions disclosed herein

I. Anti-BCMA antibodies disclosed herein

In one aspect, the invention provides an antibody, particularly a single-chain antibody (e.g., a single-chain scFv antibody), that binds to BCMA (particularly membrane-bound BCMA) with high target specificity and high affinity.

The antibodies disclosed herein have one or more of the following properties:

(i) binding to BCMA (e.g., human BCMA) with high affinity, e.g., with a $K_D$ of less than 100 nM, e.g., less than 50 nM, e.g., 5-30 nM, preferably less than 10 nM;

(ii) binding to BCMA (e.g., human BCMA) expressed on the cell surfaces with high affinity, e.g., with an $EC_{50}$ of less than 100 nM, e.g., less than 50 nM, e.g., 1-40 nM, preferably less than 20 nM, more preferably less than 10 or 5 nM;

(iii) specifically binding to an epitope on BCMA, particularly on the extracellular domain (ECD) of BCMA (e.g., recognizing the same or a similar epitope as any of the antibodies listed in Table 1);

(iv) exhibiting the same or similar binding affinity and/or specificity as any of the antibodies listed in Table 1;

(v) inhibiting (e.g., competitively inhibiting) the binding of the antibody molecules described herein, e.g., any of the antibody molecules shown in Table 1, to BCMA;

(vi) binding to the same or an overlapping epitope with any one of the antibodies shown in Table 1;

(vii) competitively binding to BCMA and/or to the same epitope on BCMA with any one of the antibodies shown in Table 1;

(viii) binding to human BCMA and cross-reacting with monkey BCMA;

(ix) having one or more biological properties of an antibody molecule described herein, e.g., any one of the antibody molecules listed in Table 1;

(x) having one or more pharmacokinetic properties of an antibody described herein, e.g., any one of the antibodies shown in Table 1;

(xi) inhibiting one or more activities of BCMA, resulting in, for example, one or more phenomena of reduced B cells or plasma cells expressing BCMA, and inhibition of survival or proliferation of the said cells;

(xii) substantially not binding to BAFF-R or TACI;

(xiii) Inhibiting or reducing the binding of BCMA to ligands thereof, e.g., to BAFF or APRIL or to both.

In some embodiments, the anti-BCMA antibody molecule disclosed herein binds to human BCMA (e.g., the polypeptide of SEQ ID NO: 74) with high affinity, e.g., with a dissociation equilibrium constant ($K_D$) less than about 100 nM, less than or equal to about 80 nM, 70 nM, 60 nM, or 50 nM, preferably less than or equal to about 40 nM, 30 nM, or 20 nM, more preferably less than or equal to about 10 nM, 9 nM, 8 nM, 7 nM, 6 nM, 5 nM, 4 nM, 3 nM, or 2 nM, e.g., as determined by biolayer interferometry (e.g., Fortebio affinity assay).

In some embodiments, the anti-BCMA antibody molecule disclosed herein binds to human BCMA (e.g., the polypeptide of SEQ ID NO: 74) with a dissociation rate constant (Kais) less than $3 \times 10^{-2}$, $1.5 \times 10^{-2}$, $5 \times 10^{-3}$, or $3 \times 10^{-3}$ s$^{-1}$, e.g., about $1.46 \times 10^{-3}$ s$^{-1}$. In some embodiments, the anti-BCMA antibody molecule binds to BCMA with an association rate constant ($K_{on}$) greater than $1 \times 10^4$, $5 \times 10^4$, $1 \times 10^5$, $5 \times 10^5$, or $8 \times 10^5$ M$^{-1}$s$^{-1}$, for example, the anti-BCMA antibody molecule binds to BCMA with the $K_a$ of about $7.29 \times 10^5$ M$^{-1}$s$^{-1}$.

In some embodiments, the anti-BCMA antibody molecule disclosed herein binds to BCMA-expressing cells, preferably a multiple myeloma cell line (e.g., NCI-H929) expressing human BCMA on cell surface, with high affinity, preferably with an EC$_{50}$, as measured by flow cytometry (e.g., FACS™), less than about 200 nM, 150 nM or 100 nM, preferably less than or equal to about 80 nM, 70 nM, 60 nM or 50 nM, and more preferably less than or equal to about 40 nM, 30 nM or 20 nM, most preferably less than or equal to about 10 nM, 9 nM, 8 nM, 7 nM, 6 nM, 5 nM, 4 nM, 3 nM, or 2 nM.

In one embodiment, an antibody molecule binds to human BCMA comprising an amino acid sequence of SEQ ID NO: 74. In some embodiments, the antibody molecule binds to an epitope on BCMA, preferably on the extracellular domains of BCMA.

In some embodiments, the antibody molecule is a full-length antibody. In other embodiments, the antibody molecule is an antibody fragment. For example, the antibody molecule disclosed herein may comprise or may be an Fab, an scFab, an Fab', an F(ab')$_2$, an Fab'-SH, an Fv, a single-chain scFv antibody, a diabody, a triabody, a tetrabody, a minibody, or a single-domain antibody (sdAb). In one preferred embodiment, the antibody molecule disclosed herein is a single-chain scFv antibody. In one preferred embodiment, the antibody molecule disclosed herein comprises an scFv and an Fc region linked thereto. In one preferred embodiment, the antibody molecule disclosed herein is fully humanized.

Variable Regions of Antibodies

"Variable region" or "variable domain" is a domain in the heavy or light chain of an antibody that is involved in binding of the antibody to antigen thereof. A heavy chain variable region (VH) and a light chain variable region (VL) can be further subdivided into hypervariable regions (HVRs, also known as complementarity determining regions (CDRs)) with more conservative regions (i.e., Framework Regions (FRs)) interposed therebetween. Each VH or VL is composed of three CDRs and four FRs, arranged from amino-terminus to carboxy-terminus in the following order: FR1, CDR1, FR2, CDR2, FR3, CDR3 and FR4. In some cases, a single VH or VL domain is sufficient to provide antigen-binding specificity. Furthermore, antibodies that bind to a particular antigen can be isolated by screening libraries of complementarity VL or VH domains by virtue of VH or VL domains from antibodies that bind the antigen (see, e.g., Portolano, S. et al., J. Immunol. 150 (1993) 880-887; Clackson, T. et al., Nature 352 (1991) 624-628). As used herein, "VH" or "VH domain" includes the heavy chain variable regions (VH) of a full-length antibody, an Fv, an scFv, a dsFv, an Fab, an scFab or other antibody fragments disclosed herein. As used herein, "VL" or "VL domain" includes the light chain variable regions (VH) of a full-length antibody, an Fv, an scFv, a dsFv, an Fab, an scFab or other antibody fragments disclosed herein.

In one embodiment, the anti-BCMA antibody molecule disclosed herein comprises: (i) an antigen-binding region identical to the antigen-binding region (e.g., a heavy chain variable region and light chain variable region pair) of any of the antibodies listed in Table 1; or (ii) an antigen-binding region having, for example, at least 80%, 85%, 90%, 92%, 95%, 97%, 98%, 99% or higher identity in amino acid sequence to the antigen-binding region of (i).

In yet another embodiment, the anti-BCMA antibody molecule disclosed herein comprises: (i) a heavy chain variable region identical to the heavy chain variable region of any one of the antibodies listed in Table 1; or (ii) a heavy chain variable region having, e.g., at least 80%, 85%, 90%, 92%, 95%, 97%, 98%, 99% or higher identity in amino acid sequence to the heavy chain variable region of (i); or (iii) a variant of heavy chain variable region of (i), wherein the variant comprises at least one but no more than 30, 20 or 10 amino acid alterations (preferably amino acid substitutions, preferably conservative substitutions), and preferably the variant comprises a total of no more than 10, preferably 5-0, amino acid alterations (preferably amino acid substitutions) in three heavy chain complementarity determining regions (CDRs).

In yet another embodiment, the anti-BCMA antibody molecule disclosed herein comprises: (i) a light chain variable region identical to the light chain variable region of any one of the antibodies listed in Table 1; or (ii) a light chain variable region having, e.g., at least 80%, 85%, 90%, 92%, 95%, 97%, 98%, 99% or higher identity in amino acid sequence to the light chain variable region of (i); or (iii) a variant of the light chain variable region of (i), wherein the variant comprises at least one but no more than 30, 20 or 10 amino acid alterations (preferably amino acid substitutions, preferably conservative substitutions), and preferably the variant comprises a total of no more than 10, preferably 5-0, amino acid alterations (preferably amino acid substitutions) in three light chain complementarity determining regions (CDRs).

In yet another embodiment, the anti-BCMA antibody molecule disclosed herein comprises a heavy chain variable region and a light chain variable region, wherein the heavy chain variable region is selected from:

(i) a heavy chain variable region identical to the heavy chain variable region of any one of the antibodies listed in Table 1; (ii) a heavy chain variable region having, e.g., at least 80%, 85%, 90%, 92%, 95%, 97%, 98%, 99% or higher identity in amino acid sequence to the heavy chain variable region of (i); and (iii) a variant of heavy chain variable region of (i), wherein the variant comprises at least one but no more than 30, 20 or 10 amino acid alterations (preferably amino acid substitutions, preferably conservative substitutions), and preferably the variant comprises a total of no more than 10, preferably 5-0, amino acid alterations (preferably amino acid substitutions) in three heavy chain complementarity determining regions (CDRs);

and the light chain variable region is selected from:

(i) a light chain variable region identical to the light chain variable region of any one of the antibodies listed in Table 1; (ii) a light chain variable region having, e.g., at least 80%, 85%, 90%, 92%, 95%, 97%, 98%, 99% or higher identity in amino acid sequence to the light chain variable region of (i); and (iii) a variant of the light chain variable region of (i), wherein the variant comprises at least one but no more than 30, 20 or 10 amino acid alterations (preferably amino acid substitutions, preferably conservative substitutions), and preferably the variant comprises a total of no more than 10, preferably 5-0, amino acid alterations (preferably amino acid substitutions) in three light chain complementarity determining regions (CDRs).

In some embodiments, provided is an anti-BCMA antibody, or a variant thereof, comprising amino acid sequences of a heavy and light chain variable region pair of any of the antibodies listed in Table 1. In one preferred embodiment, the antibody comprises an amino acid sequence pair selected from SEQ ID NOs: 4/31, 5/41, 5/42, 10/46, 16/50, 17/58, 23/64, 27/59, 27/71, and 27/72. In one preferred embodiment, the variant has at least 80%, 85%, 90%, 92%, 95%, 97%, 98%, 99% or higher identity in VH and/or VL amino acid sequences, or comprises at least one but no more than 30, 20 or 10 amino acid alterations (preferably amino acid substitutions, preferably conservative substitutions) in the VH and/or VL amino acid sequences.

In some embodiments, provided is an anti-BCMA antibody comprising a heavy chain variable region (VH) and a light chain variable region (VL), wherein the VH comprises an amino acid sequence selected from SEQ ID NOs: 4, 5, and 6, and the VL comprises an amino acid sequence selected from SEQ ID NOs: 31, 41, 42, and 43. In some embodiments, in the amino acid sequence of SEQ ID NO: 6, X represents any amino acid, preferably an amino acid residue at the corresponding position of SEQ ID NO: 4 or 5 or a conservatively substituted residue thereof. In some embodiments, in the amino acid sequence of SEQ ID NO: 43, X represents any amino acid, preferably an amino acid residue at the corresponding position of SEQ ID NO: 41 or 42 or a conservatively substituted residue thereof.

In some embodiments, provided is an anti-BCMA antibody comprising a heavy chain variable region (VH) and a light chain variable region (VL), wherein the VH comprises an amino acid sequence of SEQ ID NO: 4, and the VL comprises an amino acid sequence of SEQ ID NO: 31. The invention further provides a variant of the antibody, e.g., a variant having at least 95-99% identity or comprising no more than 10 amino acid alterations in VH and/or VL.

In some embodiments, the anti-BCMA antibody disclosed herein comprise a heavy chain variable region (VH) and a light chain variable region (VL), wherein the VH comprises an amino acid sequence of SEQ ID NO: 5, and the VL comprises an amino acid sequence selected from SEQ ID NOs: 41 and 42. The invention further provides a variant of the antibody, e.g., a variant having at least 95-99% identity or comprising no more than 10 amino acid alterations in VH and/or VL.

In some embodiments, provided is an anti-BCMA antibody comprising a heavy chain variable region (VH) and a light chain variable region (VL), wherein the VH comprises an amino acid sequence of SEQ ID NO: 10, and the VL comprises an amino acid sequence of SEQ ID NO: 46. The invention further provides a variant of the antibody, e.g., a variant having at least 95-99% identity or comprising no more than 10 amino acid alterations in VH and/or VL.

In some embodiments, the anti-BCMA antibody disclosed herein comprise a heavy chain variable region (VH) and a light chain variable region (VL), wherein the VH comprises an amino acid sequence selected from SEQ ID NOs: 16, 17, and 19, and the VL comprises an amino acid sequence selected from SEQ ID NOs: 50 and 58. In some embodiments, in the amino acid sequence of SEQ ID NO: 19, X represents any amino acid, preferably an amino acid residue at the corresponding position of SEQ ID NO: 16 or 17 or a conservatively substituted residue thereof.

In some embodiments, provided is an anti-BCMA antibody comprising a heavy chain variable region (VH) and a light chain variable region (VL), wherein the VH comprises an amino acid sequence of SEQ ID NO: 16, and the VL comprises an amino acid sequence of SEQ ID NO: 50. The invention further provides a variant of the antibody, e.g., a variant having at least 95-99% identity or comprising no more than 10 amino acid alterations in VH and/or VL.

In some embodiments, provided is an anti-BCMA antibody comprising a heavy chain variable region (VH) and a light chain variable region (VL), wherein the VH comprises an amino acid sequence of SEQ ID NO: 17, and the VL comprises an amino acid sequence of SEQ ID NO: 58. The invention further provides a variant of the antibody, e.g., a variant having at least 95-99% identity or comprising no more than 10 amino acid alterations in VH and/or VL.

In some embodiments, provided is an anti-BCMA antibody comprising a heavy chain variable region (VH) and a light chain variable region (VL), wherein the VH comprises an amino acid sequence of SEQ ID NO: 23, and the VL comprises an amino acid sequence of SEQ ID NO: 64. The invention further provides a variant of the antibody, e.g., a variant having at least 95-99% identity or comprising no more than 10 amino acid alterations in VH and/or VL.

In some embodiments, provided is an anti-BCMA antibody comprising a heavy chain variable region (VH) and a light chain variable region (VL), wherein the VH comprises an amino acid sequence of SEQ ID NO: 27, and the VL comprises an amino acid sequence selected from SEQ ID NOs: 59, 71, 72, and 73. In some embodiments, in the amino acid sequence of SEQ ID NO: 73, X represents any amino acid, preferably an amino acid residue at the corresponding position of SEQ ID NO: 71 or 72 or a conservatively substituted residue thereof.

In some embodiments, provided is an anti-BCMA antibody comprising a heavy chain variable region (VH) and a light chain variable region (VL), wherein the VH comprises an amino acid sequence of SEQ ID NO: 27, and the VL comprises an amino acid sequence selected from SEQ ID NO: 59. The invention further provides a variant of the antibody, e.g., a variant having at least 95-99% identity or comprising no more than 10 amino acid alterations in VH and/or VL.

In some embodiments, provided is an anti-BCMA antibody comprising a heavy chain variable region (VH) and a light chain variable region (VL), wherein the VH comprises an amino acid sequence of SEQ ID NO: 27, and the VL comprises an amino acid sequence selected from SEQ ID NOs: 71 and 72. The invention further provides a variant of the antibody, e.g., a variant having at least 95-99% identity or comprising no more than 10 amino acid alterations in VH and/or VL.

In any of the above embodiments, preferably, the heavy chain variable region of the antibody disclosed herein comprises no more than 10, preferably no more than 5 (e.g., 3, 2, 1 or 0) amino acid alterations (preferably amino acid substitutions, preferably conservative substitutions) in one or more CDR regions (preferably all three CDRs) compared to the amino acid sequence of the reference heavy chain variable region.

In any of the above embodiments, preferably, the light chain variable region of the antibody disclosed herein comprises no more than 10, preferably no more than 5 (e.g., 3, 2, 1 or 0) amino acid alterations (preferably amino acid substitutions, preferably conservative substitutions) in one or more CDR regions (preferably all three CDRs) compared to the amino acid sequence of the reference light chain variable region.

CDR Regions of Antibodies

"Complementarity determining region", "CDR region" or "CDR" (used interchangeably herein with a "hypervariable region" (HVR)) is an amino acid region in the variable region of an antibody that is primarily responsible for binding to an epitope of an antigen. The CDRs of the heavy and light chains are generally referred to as CDR1, CDR2, and CDR3, and are numbered sequentially from the N-terminus. The CDRs located in the heavy chain variable domain of the antibody are referred to as HCDR1, HCDR2 and HCDR3, whereas the CDRs located in the light chain variable domain of the antibody are referred to as LCDR1, LCDR2 and LCDR3.

Various schemes for determining the CDR sequence of a given VH or VL amino acid sequence are known in the art. For example, Kabat complementarity determining regions (CDRs) are determined based on sequence variability and are the most commonly used (Kabat et al., Sequences of Proteins of Immunological Interest, 5th Ed. Public Health Service, National Institutes of Health, Bethesda, Md. (1991)). Chothia scheme is based on the positions of structural loops (Chothia and Lesk, J. mol. biol. 196:901-917 (1987)). AbM HVRs are a compromise between Kabat HVRs and Chothia structural loops and are used by Oxford Molecular's AbM antibody modeling software. The "Contact" HVRs are based on analysis of available complex crystal structures. HVR/CDR residues of different CDR determination schemes are described below.

| CDR | Kabat scheme | AbM scheme | Chothia scheme | Contact scheme |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |
| (Kabat numbering system) | | | | |
| HCDR1 | H31-H35 | H26-H35 | H26-H32 | H30-H35 |
| (Chothia Numbering System) | | | | |
| HCDR2 | H50-H65 | H50-H58 | H53-H55 | H47-H58 |
| HCDR3 | H95-H102 | H95-H102 | H96-H101 | H93-H101 |
| (Kabat numbering system) | | | | |

HVRs can also be HVR sequences located at following Kabat residue positions according to the Kabat numbering system:
positions 24-36 or 24-34 (LCDR1), positions 46-56 or 50-56 (LCDR2), and positions 89-97 or 89-96 (LCDR3) in VL; and positions 26-35 or 27-35B (HCDR1), positions 50-65 or 49-65 (HCDR2), and positions 93-102, 94-102, or 95-102 (HCDR3) in VH.

In one embodiment, the HVRs of the antibody disclosed herein are HVR sequences located at the following Kabat residue positions according to the Kabat numbering system:
positions 24-34 (LCDR1), 50-56 (LCDR2), and 89-97 (LCDR3) in the VL, and positions 27-35B (HCDR1), 50-65 (HCDR2), and 93-102 (HCDR3) in the VH.

HVRs can also be determined based on the same Kabat numbering positions of a reference CDR sequence (e.g., any one of the exemplary CDRs disclosed herein).

Unless otherwise stated, the term "CDR", "CDR sequence", "HVR", or "HVR sequence" used herein includes HVR or CDR sequences determined in any of the ways described above.

Unless otherwise stated, residue positions of an antibody variable region (including heavy chain variable region residues and light chain variable region residues) are numbered according to the Kabat numbering system (Kabat et al., Sequences of Proteins of Immunological Interest, 5th Ed. Public Health Service, National Institutes of Health, Bethesda, Md. (1991)).

In one preferred embodiment, the HCDR1 of the antibody disclosed herein is a CDR sequence determined according to the AbM scheme, whereas remaining CDRs are CDR sequences determined according to the Kabat protocol. In another preferred embodiment, the CDR sequence disclosed herein is shown in Table 2.

Antibodies with different specificities (i.e., different binding sites for different antigens) have different CDRs. However, although CDRs differ from antibody to antibody, only a limited number of amino acid positions within the CDRs are directly involved in antigen binding. The smallest overlapping region can be determined using at least two of the Kabat, Chothia, AbM, and Contact schemes, thereby providing a "minimal binding unit" for antigen binding. The minimal binding unit may be a sub-portion of the CDR. As will be appreciated by those skilled in the art, residues in remaining portions of the CDR sequences can be determined by the structure and protein folding of the antibody. Thus, variants of any CDR presented herein are also considered. For example, in a variant of one CDR, the amino acid residue of the minimal binding unit may remain unchanged, while the remaining CDR residues defined by the Kabat or Chothia may be conservatively substituted.

In some embodiments, the antibody disclosed herein comprises at least one, two, three, four, five, or six CDRs identical to corresponding CDRs of any of the antibodies listed in Table 1, or variants thereof. In some embodiments, the antibody disclosed herein comprises at least one, two, or three HCDRs identical to the corresponding heavy chain CDRs of any one of the antibodies listed in Table 1, or variants thereof. In some embodiments, the antibody disclosed herein comprises at least one, two, or three LCDRs identical to the corresponding light chain CDRs of any one of the antibodies listed in Table 1, or variants thereof. Herein, a CDR variant is a CDR that has been modified by at least one, e.g., 1 or 2 or 3 amino acid substitutions, deletions, and/or insertions, wherein an antigen-binding molecule comprising the CDR variant substantially retains the biological properties of the antigen-binding molecule comprising the unmodified CDR, e.g., retains at least 60%, 70%, 80%, 90%, or 100% of the biological activity (e.g., antigen-binding capacity). It is understood that each CDR may be modified independently or in combination. Preferably, the amino acid modification is an amino acid substitution, in particular a conservative amino acid substitution, such as a preferred conservative amino acid substitution listed in Table A.

In some embodiments, the antibody disclosed herein comprises a heavy chain variable region having a heavy chain complementarity determining regions 3 (HCDR3), and the HCDR3:

(i) is identical to an HCDR3 of a heavy chain variable region of any one of the antibodies listed in Table 1; or (ii) comprises at least 1 and no more than 5 (preferably 1-3, and more preferably 1-2) amino acid alterations (preferably substitutions, and more preferably conservative substitutions) compared to the HCDR3 of (i).

In some embodiments, the antibody or the antigen-binding fragment thereof disclosed herein comprises a heavy chain variable region and a light chain variable region, and the heavy chain complementarity determining regions 3 (HCDR3) and light chain complementarity determining regions 3 (LCDR3) of the antibody:

(i) are identical to HCDR3 and LCDR3 of heavy and light chain variable region sequences of any one of the antibodies listed in Table 1; or (ii) comprise at least 1 and no more than 5 (preferably 1-3, and more preferably 1-2) amino acid alterations (preferably substitutions, and more preferably conservative substitutions) compared to the HCDR3 and LCDR3 of (i).

In some embodiments, the antibody or the antigen-binding fragment thereof disclosed herein comprises a heavy chain variable region having HCDR1, HCDR2, and HCDR3, and the HCDR1, HCDR2, and HCDR3:

(i) are respectively identical to HCDR1, HCDR2, and HCDR3 of a heavy chain variable region of any one of the antibodies listed in Table 1; or (ii) comprise 1-10, preferably no more than 5 (preferably 1, 2 or 3) amino acid alterations (preferably substitutions, and more preferably conservative substitutions) compared to the HCDR1, HCDR2 and HCDR3 of (i), and preferably no more than 3 amino acid alterations (e.g. 2, 1 or 0) in the HCDR3 region.

In some embodiments, the antibody or the antigen-binding fragment thereof disclosed herein comprises a heavy chain variable region having heavy chain complementarity determining regions HCDR1, HCDR2 and HCDR3 and a light chain variable region having light chain complementarity determining regions LCDR1, LCDR2 and LCDR3, wherein the HCDR1, HCDR2, HCDR3, and LCDR3:

(i) are respectively identical to HCDR1, HCDR2, HCDR3 and LCDR3 of heavy and light chain variable regions of any one of the antibodies listed in Table 1; or (ii) comprise 1-10 (preferably 1-5, and more preferably 1, 2 or 3) amino acid alterations (preferably substitutions, and more preferably conservative substitutions) compared to the HCDR1, HCDR2, HCDR3 and LCDR3 of (i).

In some embodiments, the antibody or the antigen-binding fragment thereof disclosed herein comprises a light chain variable region having light chain complementarity determining regions LCDR1, LCDR2, and LCDR3, wherein the LCDR1, LCDR2 and LCDR3:

(i) are respectively identical to LCDR1, LCDR2, and LCDR3 of a light chain variable region of any one of the antibodies listed in Table 1; or (ii) comprise 1-10 (preferably 1-5, and more preferably 1, 2 or 3) amino acid alterations (preferably substitutions, and more preferably conservative substitutions) compared to the LCDR1, LCDR2, and LCDR3 of (i).

In some embodiments, the antibody or the antigen-binding fragment thereof disclosed herein comprises a heavy chain variable region having heavy chain complementarity determining regions HCDR1, HCDR2 and HCDR3 and a light chain variable region having light chain complementarity determining regions LCDR1, LCDR2 and LCDR3, wherein the LCDR1, LCDR2, LCDR3, and HCDR3:

(i) are respectively identical to LCDR1, LCDR2, LCDR3 and HCDR3 of heavy and light chain variable regions of any one of the antibodies listed in Table 1; or (ii) comprise 1-10 (preferably 1-5, and more preferably 1, 2 or 3) amino acid alterations (preferably substitutions, and more preferably conservative substitutions) compared to the LCDR1, LCDR2, LCDR3 and HCDR3 of (i).

In some embodiments, the antibody or the antigen-binding fragment thereof disclosed herein comprises a heavy chain variable region having heavy chain complementarity determining regions HCDR1, HCDR2 and HCDR3 and a light chain variable region having light chain complementarity determining regions LCDR1, LCDR2 and LCDR3, wherein the antibody:

(i) comprises the sequences of all the six CDR regions of heavy and light chain variable regions of any one of the antibodies listed in Table 1, or (ii) comprises no more than 10, preferably no more than 5 (e.g., 3, 2, 1, or 0) amino acid alterations (preferably amino acid substitutions, preferably conservative substitutions) in all the six CDR regions, compared to any of the antibodies listed in Table 1.

In one embodiment, the antibody or the antigen-binding fragment thereof disclosed herein comprises:

(i) HCDR1, HCDR2 and HCDR3 sequences of a heavy chain variable region set forth in SEQ ID NO: 4 or 5, and LCDR1, LCDR2 and LCDR3 sequences of a light chain variable region set forth in SEQ ID NO: 31, 41 or 42, (ii) HCDR1, HCDR2 and HCDR3 sequences of a heavy chain variable region set forth in SEQ ID NO: 10, and LCDR1, LCDR2 and LCDR3 sequences of a light chain variable region set forth in SEQ ID NO: 46, (iii) HCDR1, HCDR2 and HCDR3 sequences of a heavy chain variable region set forth in SEQ ID NO: 16 or 17, and LCDR1, LCDR2 and LCDR3 sequences of a light chain variable region set forth in SEQ ID NO: 50 or 58, (iv) HCDR1, HCDR2 and HCDR3 sequences of a heavy chain variable region set forth in SEQ ID NO: 23, and LCDR1, LCDR2 and LCDR3 sequences of a light chain variable region set forth in SEQ ID NO: 64, or (v) HCDR1, HCDR2 and HCDR3 sequences of a heavy chain variable region set forth in SEQ ID NO: 27, and LCDR1, LCDR2 and LCDR3 sequences of a light chain variable region set forth in SEQ ID NO: 59, 71 or 72.

In one preferred embodiment, the antibody or the antigen-binding fragment disclosed herein comprises HCDR1, HCDR2, HCDR3, LCDR1, LCDR2, and LCDR3 sequences of a heavy chain variable region (VH) and a light chain variable region (VL) selected from:

(i) a VH of SEQ ID NO: 4 and a VL of SEQ ID NO: 31;

(i) a VH of SEQ ID NO: 5 and a VL of SEQ ID NO: 41;

(iii) a VH of SEQ ID NO: 5 and a VL of SEQ ID NO: 42;

(iv) a VH of SEQ ID NO: 10 and a VL of SEQ ID NO: 46;

(v) a VH of SEQ ID NO: 16 and a VL of SEQ ID NO: 50;

(vi) a VH of SEQ ID NO: 17 and a VL of SEQ ID NO: 58;

(vii) a VH of SEQ ID NO:23 and a VL of SEQ ID NO: 64;

(viii) a VH of SEQ ID NO: 27 and a VL of SEQ ID NO: 59;

(ix) a VH of SEQ ID NO: 27 and a VL of SEQ ID NO: 71; and (x) a VH of SEQ ID NO: 27 and a VL of SEQ ID NO: 72.

In some embodiments, the invention provides an HCDR3 selected from SEQ ID NOs: 3, 9, 13, 14, 15, 22, and 26, and an antibody or an antigen-binding fragment comprising the HCDR3.

In some embodiments, the invention provides a combination of HCDR3 and LCDR3 sequences, and an antibodies or antigen-binding fragments comprising the combination, wherein the combination is selected from: (i) an HCDR3 of SEQ ID NO: 3, and an LCDR3 selected from SEQ ID NOs: 30, 38, 39 and 40; (ii) an HCDR3 of SEQ ID NO: 9, and an LCDR3 of SEQ ID NO: 45; (iii) an HCDR3 selected from SEQ ID NOs: 13, 14 and 15, and an LCDR3 selected from SEQ ID NOs: 49 and 55; (iv) an HCDR3 of SEQ ID NO: 22, and an LCDR3 of SEQ ID NO: 63; and (v) an HCDR3 of SEQ ID NO: 26, and an LCDR3 selected from SEQ ID NOs: 56, 68, 69, and 70. The invention further provides a variant of the combination of CDRs, e.g., a variant that comprises at least one and no more than 20, 10 or 5 amino acid alterations (preferably amino acid substitutions, and more preferably conservative substitutions) in total in the CDRs. The invention further provides an anti-BCMA antibody or an antigen-binding fragment comprising the variant.

In other embodiments, the invention provides a combination of CDR sequences, and an antibodies or antigen-binding fragments comprising the combination, wherein the combination is selected from: (i) an HCDR1 of SEQ ID NO: 1, an HCDR2 of SEQ ID NO: 2, and an HCDR3 of SEQ ID NO: 3; (ii) an HCDR1 of SEQ ID NO: 7, an HCDR2 of SEQ ID NO: 8, and an HCDR3 of SEQ ID NO: 9; (iii) an HCDR1 of SEQ ID NO: 11, an HCDR2 of SEQ ID NO: 12, and an HCDR3 of SEQ ID NO: 13, 14 or 15; (iv) an HCDR1 of SEQ ID NO: 20, an HCDR2 of SEQ ID NO: 21, and an HCDR3 of SEQ ID NO: 22; and (v) an HCDR1 of SEQ ID NO: 24, an HCDR2 of SEQ ID NO: 25, and an HCDR3 of SEQ ID NO: 26. In some embodiments, the antibody or the antigen-binding fragment thereof disclosed herein comprises an HCDR1 of SEQ ID NO: 11, an HCDR2 of SEQ ID NO: 12, and an HCDR3 of SEQ ID NO: 13 or 14.

In other embodiments, the invention provides a heavy chain CDR combination (in the order of HCDR1, HCDR2 and HCDR3) of amino acid sequences selected from SEQ ID NOs: 1/2/3, 7/8/9, 11/12/13, 11/12/14, 20/21/22, and 24/25/26. The invention further provides a variant of the heavy chain CDR combination, and in one preferred embodiment, the variant comprises at least one and no more than 20, 10 or 5 amino acid alterations (preferably amino acid substitutions, and more preferably conservative substitutions) in total in the three CDRs. The invention further provides an anti-BCMA antibody comprising the heavy chain CDR combination or the variant.

In some embodiments, the invention provides a CDR combination, and an antibody or an antigen-binding fragment comprising the combinations, wherein the CDR combination is selected from: (i) an LCDR1 of SEQ ID NO: 28, an LCDR2 of SEQ ID NO: 29, and an LCDR3 of SEQ ID NO: 30; (ii) an LCDR1 of SEQ ID NO: 32, 33 or 34, an LCDR2 of SEQ ID NO: 35, 36 or 37, and an LCDR3 of SEQ ID NO: 38, 39 or 40; (iii) an LCDR1 of SEQ ID NO: 32, an LCDR2 of SEQ ID NO: 44, and an LCDR3 of SEQ ID NO: 45; (iv) an LCDR1 of SEQ ID NO: 47, an LCDR2 of SEQ ID NO: 48, and an LCDR3 of SEQ ID NO: 49; (v) an LCDR1 of SEQ ID NO: 51, an LCDR2 of SEQ ID NO: 54, and an LCDR3 of SEQ ID NO: 55; (vi) an LCDR1 of SEQ ID NO: 61, an LCDR2 of SEQ ID NO: 62, and an LCDR3 of SEQ ID NO: 63; (vii) an LCDR1 of SEQ ID NO: 52, an LCDR2 of SEQ ID NO: 62, and an LCDR3 of SEQ ID NO: 56; and (viii) an LCDR1 of SEQ ID NO: 65, 66 or 67, an LCDR2 of SEQ ID NO: 62, and an LCDR3 of SEQ ID NO: 68, 69 or 70.

In yet another embodiment, the invention provides a light chain CDR combination (in the order of LCDR1, LCDR2, and LCDR3) of amino acid sequences selected from SEQ ID NOs: 28/29/30, 32/35/38, 33/36/39, 32/44/45, 47/48/49, 51/54/55, 61/62/63, 52/62/56, 65/62/68, and 66/62/69. The invention further provides a variant of the light chain CDR combination, and in one preferred embodiment, the variant comprises at least one and no more than 20, 10 or 5 amino acid alterations (preferably amino acid substitutions, and more preferably conservative substitutions) in total in the three CDRs. The invention further provides an anti-BCMA antibody comprising the light chain CDR combination or the variant, or an antibody-binding fragment thereof.

In some embodiments, the invention provides a CDR combination, and an antibody or an antigen-binding fragment comprising the combinations, wherein the CDR combination is selected from: (i) HCDR1 of SEQ ID NO: 1, HCDR2 of SEQ ID NO: 2, HCDR3 of SEQ ID NO: 3, LCDR1 of SEQ ID NO: 28, LCDR2 of SEQ ID NO: 29, and LCDR3 of SEQ ID NO: 30; (ii) HCDR1 of SEQ ID NO: 1, HCDR2 of SEQ ID NO: 2, HCDR3 of SEQ ID NO: 3, LCDR1 of SEQ ID NO: 32, 33 or 34, LCDR2 of SEQ ID NO: 35, 36 or 37, and LCDR3 of SEQ ID NO: 38, 39 or 40; (iii) HCDR1 of SEQ ID NO: 7, HCDR2 of SEQ ID NO: 8, HCDR3 of SEQ ID NO: 9, LCDR1 of SEQ ID NO: 32, LCDR2 of SEQ ID NO: 44, and LCDR3 of SEQ ID NO: 45; (iv) HCDR1 of SEQ ID NO: 11, HCDR2 of SEQ ID NO: 12, HCDR3 of SEQ ID NO: 13, 14 or 15, LCDR1 of SEQ ID NO: 47, LCDR2 of SEQ ID NO: 48, and LCDR3 of SEQ ID NO: 49; (v) HCDR1 of SEQ ID NO: 11, HCDR2 of SEQ ID NO: 12, HCDR3 of SEQ ID NO: 13, 14 or 15, LCDR1 of SEQ ID NO: 51, LCDR2 of SEQ ID NO: 54, and LCDR3 of SEQ ID NO: 55; (vi) HCDR1 of SEQ ID NO: 20, HCDR2 of SEQ ID NO: 21, HCDR3 of SEQ ID NO: 22, LCDR1 of SEQ ID NO: 61, LCDR2 of SEQ ID NO: 62, and LCDR3 of SEQ ID NO: 63; (vii) HCDR1 of SEQ ID NO: 24, HCDR2 of SEQ ID NO: 25, HCDR3 of SEQ ID NO: 26, LCDR1 of SEQ ID NO: 52, LCDR2 of SEQ ID NO: 62, and LCDR3 of SEQ ID NO: 56; and (viii) HCDR1 of SEQ ID NO: 24, HCDR2 of SEQ ID NO: 25, HCDR3 of SEQ ID NO: 26, LCDR1 of SEQ ID NO: 65, 66 or 67, LCDR2 of SEQ ID NO: 62, and LCDR3 of SEQ ID NO: 68, 69 or 70.

In yet another embodiment, the invention provides a heavy and light chain CDR combination (in the order of HCDR1, HCDR2, HCDR3, LCDR1, LCDR2 and LCDR3) of amino acid sequences selected from SEQ ID NOs: 1/2/3/28/29/30, 1/2/3/32/35/38, 1/2/3/33/36/39, 7/8/9/32/44/45, 11/12/13/47/48/49, 11/12/14/51/54/55, 20/21/22/61/62/63, 24/25/26/52/62/56, 24/25/26/65/62/68, and 24/25/26/66/62/69. The invention further provides a variant of the CDR combination, and in one preferred embodiment, the variant comprises at least one and no more than 20, 10 or 5 amino acid alterations (preferably amino acid substitutions, and more preferably conservative substitutions) in total in the six CDRs. The invention further provides an anti-BCMA antibody comprising the heavy and light chain CDR combination or the variant, or an antibody-binding fragment thereof.

In some embodiments, the antibody or the antigen-binding fragment thereof disclosed herein comprises: an HCDR1 of SEQ ID NO: 1, an HCDR2 of SEQ ID NO: 2, an HCDR3 of SEQ ID NO: 3, an LCDR1 of SEQ ID NO: 28, an LCDR2 of SEQ ID NO: 29, and an LCDR3 of SEQ ID NO: 30.

In some embodiments, the antibody or the antigen-binding fragment thereof disclosed herein comprises: an HCDR1 of SEQ ID NO: 1, an HCDR2 of SEQ ID NO: 2, an HCDR3 of SEQ ID NO: 3, an LCDR1 of SEQ ID NO: 32, an LCDR2 of SEQ ID NO: 35, and an LCDR3 of SEQ ID NO: 38.

In some embodiments, the antibody or the antigen-binding fragment thereof disclosed herein comprises: an HCDR1 of SEQ ID NO: 1, an HCDR2 of SEQ ID NO: 2, an HCDR3 of SEQ ID NO: 3, an LCDR1 of SEQ ID NO: 33, an LCDR2 of SEQ ID NO: 36, and an LCDR3 of SEQ ID NO: 39.

In some embodiments, the antibody or the antigen-binding fragment thereof disclosed herein comprises: an HCDR1 of SEQ ID NO: 7, an HCDR2 of SEQ ID NO: 8, an HCDR3 of SEQ ID NO: 9, an LCDR1 of SEQ ID NO: 32, an LCDR2 of SEQ ID NO: 44, and an LCDR3 of SEQ ID NO: 45.

In some embodiments, the antibody or the antigen-binding fragment thereof disclosed herein comprises: an HCDR1 of SEQ ID NO: 11, an HCDR2 of SEQ ID NO: 12, an HCDR3 of SEQ ID NO: 13, an LCDR1 of SEQ ID NO: 47, an LCDR2 of SEQ ID NO: 48, and an LCDR3 of SEQ ID NO: 49.

In some embodiments, the antibody or the antigen-binding fragment thereof disclosed herein comprises: an HCDR1 of SEQ ID NO: 11, an HCDR2 of SEQ ID NO: 12, an HCDR3 of SEQ ID NO: 14, an LCDR1 of SEQ ID NO: 51, an LCDR2 of SEQ ID NO: 54, and an LCDR3 of SEQ ID NO: 55.

In some embodiments, the antibody or the antigen-binding fragment thereof disclosed herein comprises: an HCDR1 of SEQ ID NO: 20, an HCDR2 of SEQ ID NO: 21, an HCDR3 of SEQ ID NO: 22, an LCDR1 of SEQ ID NO: 61, an LCDR2 of SEQ ID NO: 62, and an LCDR3 of SEQ ID NO: 63.

In some embodiments, the antibody or the antigen-binding fragment thereof disclosed herein comprises: an HCDR1 of SEQ ID NO: 24, an HCDR2 of SEQ ID NO: 25, an HCDR3 of SEQ ID NO: 26, an LCDR1 of SEQ ID NO: 52, an LCDR2 of SEQ ID NO: 62, and an LCDR3 of SEQ ID NO: 56.

In some embodiments, the antibody or the antigen-binding fragment thereof disclosed herein comprises: an HCDR1 of SEQ ID NO: 24, an HCDR2 of SEQ ID NO: 25, an HCDR3 of SEQ ID NO: 26, an LCDR1 of SEQ ID NO: 65, an LCDR2 of SEQ ID NO: 62, and an LCDR3 of SEQ ID NO: 68.

In some embodiments, the antibody or the antigen-binding fragment thereof disclosed herein comprises: an HCDR1 of SEQ ID NO: 24, an HCDR2 of SEQ ID NO: 25, an HCDR3 of SEQ ID NO: 26, an LCDR1 of SEQ ID NO: 66, an LCDR2 of SEQ ID NO: 62, and an LCDR3 of SEQ ID NO: 69.

In some embodiments, X in SEQ ID NO: 15 represents any amino acid residue, preferably an amino acid residue at the corresponding position of SEQ ID NO: 13 or 14 or a conservatively substituted residue thereof, preferably S or R or a conservatively substituted residue thereof. In some embodiments, X in SEQ ID NO: 34 represents any amino acid residue, preferably an amino acid residue at the corresponding position of SEQ ID NO: 32 or 33 or a conservatively substituted residue thereof. In some embodiments, X in SEQ ID NO: 37 represents any amino acid residue, preferably an amino acid residue at the corresponding position of SEQ ID NO: 35 or 36 or a conservatively substituted residue thereof. In some embodiments, X in SEQ ID NO: 40 represents any amino acid residue, preferably an amino acid residue at the corresponding position of SEQ ID NO: 38 or 39 or a conservatively substituted residue thereof. In some embodiments, X in SEQ ID NO: 67 represents any amino acid residue, preferably an amino acid residue at the corresponding position of SEQ ID NO: 65 or 66 or a conservatively substituted residue thereof. In some embodiments, X in SEQ ID NO: 70 represents any amino acid residue, preferably an amino acid residue at the corresponding position of SEQ ID NO: 68 or 69 or a conservatively substituted residue thereof.

In the above embodiments of the antibody disclosed herein, "conservative substitution" refers to an amino acid alteration that results in the replacement of an amino acid with a chemically similar amino acid. Conservative substitution tables providing functionally similar amino acids are well known in the art. In any of the embodiments herein, in one preferred aspect, the conservatively substituted residue is from the conservative substitution Table A below, preferably the preferred substituted residues shown in Table A.

TABLE A

| Original residues | Exemplary substitution | Preferred conservative amino acid substitution |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norleucine | Leu |

Exemplary Antibody Sequences

The invention provides isolated and characterized fully humanized antibodies that specifically bind to BCMA (e.g., human BCMA) as in the examples. The variable region sequences of the exemplary antibodies disclosed herein are listed in Table 1 below. The exemplary CDR sequences of the antibodies are given in Table 2 below (see also FIG. 4).

TABLE 1

Amino acid and nucleotide sequences of heavy and light chain variable regions of exemplary fully humanized antibody molecules

| Antibody | VH | VH DNA | VL | VL DNA |
|---|---|---|---|---|
| ADI-34848 | SEQ ID NO:4 | SEQ ID NO:75 | SEQ ID NO:31 | SEQ ID NO:83 |
| ADI-34849 | SEQ ID NO:5 | SEQ ID NO:76 | SEQ ID NO:41 | SEQ ID NO:84 |
| ADI-34850 | SEQ ID NO:5 | SEQ ID NO:76 | SEQ ID NO:42 | SEQ ID NO:85 |
| ADI-34854 | SEQ ID NO:10 | SEQ ID NO:77 | SEQ ID NO:46 | SEQ ID NO:86 |

TABLE 1-continued

Amino acid and nucleotide sequences of heavy and light chain variable regions of exemplary fully humanized antibody molecules

| Antibody | VH | VH DNA | VL | VL DNA |
|---|---|---|---|---|
| ADI-34846 | SEQ ID NO:16 | SEQ ID NO:78 | SEQ ID NO:50 | SEQ ID NO:87 |
| ADI-34857 | SEQ ID NO:17 | SEQ ID NO:79 | SEQ ID NO:58 | SEQ ID NO:88 |
| ADI-34832 | SEQ ID NO:23 | SEQ ID NO:81 | SEQ ID NO:64 | SEQ ID NO:90 |
| ADI-34859 | SEQ ID NO:27 | SEQ ID NO:80 | SEQ ID NO:59 | SEQ ID NO:89 |
| ADI-34860 | SEQ ID NO:27 | SEQ ID NO:82 | SEQ ID NO:71 | SEQ ID NO:91 |
| ADI-34861 | SEQ ID NO:27 | SEQ ID NO:82 | SEQ ID NO:72 | SEQ ID NO:92 |

TABLE 2

Amino acid sequences of exemplary heavy and light chain CDRs

| Antibody | HCDR1 | HCDR2 | HCDR3 | LCDR1 | LCDR2 | LCDR3 |
|---|---|---|---|---|---|---|
| ADI-34848 | SEQ ID NO: 1 | SEQ ID NO: 2 | SEQ ID NO: 3 | SEQ ID NO: 28 | SEQ ID NO: 29 | SEQ ID NO: 30 |
| ADI-34849 | SEQ ID NO: 1 | SEQ ID NO: 2 | SEQ ID NO: 3 | SEQ ID NO: 32 | SEQ ID NO: 35 | SEQ ID NO: 38 |
| ADI-34850 | SEQ ID NO: 1 | SEQ ID NO: 2 | SEQ ID NO: 3 | SEQ ID NO: 33 | SEQ ID NO: 36 | SEQ ID NO: 39 |
| ADI-34854 | SEQ ID NO: 7 | SEQ ID NO: 8 | SEQ ID NO: 9 | SEQ ID NO: 32 | SEQ ID NO: 44 | SEQ ID NO: 45 |
| ADI-34846 | SEQ ID NO: 11 | SEQ ID NO: 12 | SEQ ID NO: 13 | SEQ ID NO: 47 | SEQ ID NO: 48 | SEQ ID NO: 49 |
| ADI-34857 | SEQ ID NO: 11 | SEQ ID NO: 12 | SEQ ID NO: 14 | SEQ ID NO: 51 | SEQ ID NO: 54 | SEQ ID NO: 55 |
| ADI-34832 | SEQ ID NO: 20 | SEQ ID NO: 21 | SEQ ID NO: 22 | SEQ ID NO: 61 | SEQ ID NO: 62 | SEQ ID NO: 63 |
| ADI-34859 | SEQ ID NO: 24 | SEQ ID NO: 25 | SEQ ID NO: 26 | SEQ ID NO: 52 | SEQ ID NO: 62 | SEQ ID NO: 56 |
| ADI-34860 | SEQ ID NO: 24 | SEQ ID NO: 25 | SEQ ID NO: 26 | SEQ ID NO: 65 | SEQ ID NO: 62 | SEQ ID NO: 68 |
| ADI-34861 | SEQ ID NO: 24 | SEQ ID NO: 25 | SEQ ID NO: 26 | SEQ ID NO: 66 | SEQ ID NO: 62 | SEQ ID NO: 69 |

The invention further provides variants of the above antibodies. In one embodiment, the amino acid sequence of the antibody or nucleic acid encoding the amino acid sequence has been altered, but still has at least 60%, 65%, 70%, 75%, 80%, 85%, 90% or 95% or higher identity to a sequence described in Table 1. In some embodiments, the antibody comprises a altered variable region amino acid sequence which has no more than 1, 2, 3, 4, 5, or 10 amino acid alterations but still retains substantially identical antigen-binding activity compared to the corresponding variable region sequence set forth in Table 1.

Furthermore, since each of the above antibodies can bind to BCMA, VH and VL (amino acid sequences and nucleotide sequences encoding the amino acid sequences) can be "combined and paired" to generate other antibodies that bind to BCMA of the invention. The binding of such "combined and paired" antibodies to BCMA can be tested by binding assays known in the art (e.g., ELISA, and other assays described in the examples). When these chains are combined and paired, it is preferred that the VH sequence from a particular VH/VL pair is replaced with a structurally similar VH sequence. Likewise, the VL sequence from a particular VH/VL pair is preferably replaced with a structurally similar VL sequence.

In another aspect, the invention further provides variants of the above antibodies. In one embodiment, the amino acid sequences of one or more or all of the 6 CDR regions of the antibody or nucleic acids encoding the amino acid sequences have been altered. In some embodiments, when compared to the corresponding CDR region in Table 1, the altered CDR region has no more than 1, 2, 3, 4, or 5 amino acid alterations in amino acid sequence, but still retains substantially identical antigen binding activity.

Furthermore, given that each of the antibodies in Table 1 can bind to BCMA and the antigen binding specificity is dependent primarily on the CDR1, CDR2, and CDR3 regions, HCDR1, HCDR2 and HCDR3 sequences and LCDR1, LCDR2 and LCDR3 sequences can be "combined and paired" (i.e., CDRs from different antibodies can be combined and paired, such that each antibody preferably contains an HCDR1, an HCDR2, an HCDR3, an LCDR1, an LCDR2, and an LCDR3) to produce other molecules of the invention that bind to BCMA. The binding of such "combined and paired" antibodies to BCMA can be tested by binding assays known in the art (e.g., ELISA, SET, and Biacore) and other assays described in the examples. When HCDR sequences are combined and paired, CDR1, CDR2, and/or CDR3 sequences from a particular VH sequence are preferably replaced with structurally similar CDR sequences. Likewise, when LCDR sequences are combined and paired, CDR1, CDR2, and/or CDR3 sequences from a particular VL sequence are preferably replaced with structurally similar CDR sequences. It will be appreciated by those skilled in the art that other antibodies may also be generated by replacing one or more of the HCDR and/or LCDR sequences with structurally similar CDR sequences from the antibodies disclosed herein. In addition to the foregoing, in one embodiment, an antigen-binding fragment of the antibody described herein may comprise HCDR1, HCDR2 and HCDR3 sequences or LCDR1, LCDR2 and LCDR3 sequences, wherein the fragment binds to BCMA in a single-domain form.

II. Single-Chain scFv Antibodies

In one preferred aspect, the antibody disclosed herein is a single-chain scFv antibody.

As used herein, the "single-chain scFv antibody", "scFv" or "single-chain scFv" refers to a single polypeptide chain comprising a heavy chain variable region (VH) and a light chain variable region (VL) of an immunoglobulin or an antibody, wherein the VH and VL regions pair to provide an antigen binding site.

In a preferred embodiment, the VH and VL regions of the single-chain scFv antibody disclosed herein are covalently linked together by a linker peptide, such as a flexible linker peptide. The term "flexible linker peptide" is a peptide linker consisting of amino acids. Various variable domains, such as VH and VL regions, in antibodies may be linked by such peptide linkers. Peptide linkers are typically rich in glycine which contributes to flexibility and serine/threonine which contributes to solubility. For example, glycine and/or serine residues may be used alone or in combination. Non-limiting examples of the flexible linker peptides or peptide linkers are disclosed in Shen et al., Anal. Chem. 80 (6):1910-1917 (2008), WO 2012/138475 and WO 2014/087010, which are incorporated by reference in their entirety. As is known in the art, in construction of an scFv, preferably, the linker facilitates VH and VL pairing without interfering with the formation of a functionally effective antigen-binding site by the VH and VL pair.

In some embodiments, the single-chain scFv antibody disclosed herein comprises a flexible linker peptide or peptide linker consisting of amino acid residues linked by peptide bonds. In certain embodiments, the amino acids are selected from twenty natural amino acids. In certain other embodiments, one or more amino acids are selected from glycine, serine, threonine, alanine, proline, asparagine, glutamine, and lysine. In one preferred embodiment, one or more amino acids are selected from Gly, Ser, Thr, Lys, Pro, and Glu.

In some embodiments, the linker has a length of about 1-30 amino acids, about 10 to about 25 amino acids, about 15 to about 20 amino acids, about 10 to about 20 amino acids, or a length of any intervening amino acids. In a preferred embodiment, the linker has a length of 15-25 amino acid residues, and in a more preferred embodiment, the linker has a length of 15-18 amino acid residues. In some embodiments, the linker has a length of 10, 11, 12, 13, 14, 15, 16, 17, 18, 19, 20, 21, 22, 23, 24, 25 or more amino acids.

Examples of peptide linkers available herein include: a glycine polymer $(G)_n$; a glycine-serine co-polymer $(G_{1-5}S_{1-5})_n$, wherein n is an integer of at least 1, 2, 3, 4 or 5; a glycine-alanine co-polymer; an alanine-serine co-polymer; and other flexible linkers known in the art. Those skilled in the art will appreciate that in some embodiments, a linker between VH and VL may consist entirely of a flexible linker peptide, or a flexible linker peptide portion and one or more portions that form a smaller flexible structure.

In one preferred embodiment, the peptide linker is GST-SGSGKPGSGEGSTKG (SEQ ID NO: 93). In one embodiment, a nucleotide sequence encoding the amino acid sequence of SEQ ID NO: 93 is set forth in SEQ ID NO: 94. In one embodiment, another nucleotide sequence encoding the amino acid sequence of SEQ ID NO: 93 is set forth in SEQ ID NO: 97.

In one embodiment, the peptide linker is a Gly/Ser linker peptide. In one embodiment, the peptide linker is a $(G_xS)_n$ linker, wherein G=glycine, S=serine, (x=3, n=8, 9 or 10) or (x=4 and n=6, 7 or 8), and in one embodiment, x=4, n=6 or 7. In some embodiments, the linker may comprise the amino acid sequence $(G_4S)_n$, wherein n is an integer equal to or greater than 1, e.g., n is an integer from 1 to 7. In one preferred embodiment, x=4 and n=7. In one embodiment, the linker is $(G_4S)_3$. In one embodiment, the linker is $(G_4S)_4$. In one embodiment, the linker is $(G_4S)_6G_2$.

Other exemplary linkers include, but are not limited to, the following amino acid sequences: GGG; DGGGS; TGEKP (see, e.g., Liu et. al., PNAS5525-5530 (1997)); GGRR (Pomerantz et. al., 1995, ibid.); (GGGGS)n, wherein n is 1, 2, 3, 4 or 5 (Kim et. al., PNAS 93, 1156-1160 (1996); EGKSSGSGSESKVD (Chaudhary et. al., 1990, Proc. Natl. Acad. Sci. U.S.A., 87:1066-1070); KESGSVSSE-QLAQFRSLD (Bird et. al., 1988, Science, 242: 423-426); GGRRGGGS; LRQRDGERP; LRQKDGGGSERP; and LRQKD(GGGS)2ERP. Optionally, the flexible linker can be rationally designed by a computer program (Desjaais & Berg, PNAS 90:2256-2260 (1993), PNAS91:11099-11103 (1994)) capable of modeling a DNA-binding site and the peptide itself, or by phage or yeast display.

The VH and VL of the single-chain scFv antibody disclosed herein may be in either direction. In some embodiments, the scFv comprises, from N terminus to C terminus, VH-linker-VL, or VL-linker-VH. In one preferred embodiment, the single-chain scFv antibody disclosed herein comprises, from N terminus to C terminus, VL-linker-VH. In one preferred embodiment, the VL is covalently linked, at its C terminus, to the N terminus of the VH via the linker.

In some embodiments, in addition to the linker, other polypeptide fragments with specific functions may also be inserted between the VL and VH domains, for example, polypeptide fragments with functions of modulating immune responses, or polypeptide fragments with functions of causing lysis or cell killing.

In some embodiments, the single-chain antibodies may be stabilized by introducing disulfide bonds in the scFv. For example, a framework region capable of connecting the VH and VL of the scFv antibody may be linked by introducing intra- or inter-chain disulfide bonds. In one embodiment, an amino acid residue of each of the VH and VL of the antibody (e.g., position 44 of the VH and position 100 of the VL, or position 105 of the VH and position 43 of the VL, according to the Kabat numbering system) is altered into cysteine.

The single-chain scFv antibody disclosed herein may be expressed from a nucleic acid comprising VH- and VL-encoding sequences as described by Huston et. al. (Proc. Nat. Acad. Sci. USA, 85: 5879-5883, 1988). See also U.S. Pat. Nos. 5,091,513, 5,132,405 and 4,956,778, and U.S. patent publication NOs: 20050196754 and 20050196754. In some embodiments, the single-chain scFv antibody disclosed herein is expressed by a eukaryotic cell, e.g., a yeast cell, a mammalian cell such as an H293 cell or a CHO cell. In certain embodiments, the antibody disclosed herein is an anti-BCMA scFv antibody or an antigen-binding fragment thereof, which comprises an antigen-binding site having an amino acid sequence set forth in SEQ ID NO: 99 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 99. In one embodiment, the anti-BCMA scFv antibody is encoded by a nucleotide of SEQ ID NO: 100.

In certain embodiments, the anti-BCMA scFv antibody comprises a heavy chain variable region comprising an amino acid sequence of SEQ ID NO: 4 or an amino acid sequence having at least 90%, 92%, 95%, 97%, 98%, 99% or higher identity thereto, and a light chain variable region comprising an amino acid sequence of SEQ ID NO: 31 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 4. In certain embodiments, the anti-BCMA scFv comprises a VL having an amino acid sequence of SEQ ID NO: 31. In certain embodiments, the anti-BCMA scFv comprises a VH having an amino acid sequence set forth in SEQ ID NO: 4 and a VL having an amino acid sequence set forth in SEQ ID NO: 31. In certain embodiments, the anti-BCMA scFv comprises 3 HCDR sequences having an amino acid sequence set forth in SEQ ID NO: 4 and/or 3 LCDR sequences having an amino acid sequence set forth in SEQ ID NO: 31. In some embodiments, the anti-BCMA scFv comprises an HCDR3 of SEQ ID NO: 3 and an LCDR3 of SEQ ID NO: 30. In certain embodiments, the anti-BCMA scFv comprises: an HCDR1 of SEQ ID NO: 1, an HCDR2 of SEQ ID NO: 2, and an HCDR3 of SEQ ID NO: 3. In certain embodiments, the anti-BCMA scFv comprises: an LCDR1 of SEQ ID NO: 28, an LCDR2 of SEQ ID NO: 29, and an LCDR3 of SEQ ID NO: 30. In certain embodiments, the anti-BCMA scFv comprises: an HCDR1 of SEQ ID NO: 1, an HCDR2 of SEQ ID NO: 2, an HCDR3 of SEQ ID NO: 3, an LCDR1 of SEQ ID NO: 28, an LCDR2 of SEQ ID NO: 29, and an LCDR3 of SEQ ID NO: 30.

In certain embodiments, the antibody disclosed herein is an anti-BCMA scFv antibody or an antigen-binding fragment thereof, which comprises an antigen-binding site having an amino acid sequence set forth in SEQ ID NO: 102 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 102. In one embodiment, the anti-BCMA scFv antibody is encoded by a nucleotide of SEQ ID NO: 103.

In certain embodiments, the anti-BCMA scFv antibody comprises a heavy chain variable region comprising an amino acid sequence of SEQ ID NO: 5 or an amino acid sequence having at least 90%, 92%, 95%, 97%, 98%, 99% or higher identity thereto, and a light chain variable region comprising an amino acid sequence of SEQ ID NO: 41 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 5. In certain embodiments, the anti-BCMA scFv comprises a VL having an amino acid sequence of SEQ ID NO: 41. In certain embodiments, the anti-BCMA scFv comprises a VH having an amino acid sequence set forth in SEQ ID NO: 5 and a VL having an amino acid sequence set forth in SEQ ID NO: 41. In certain embodiments, the anti-BCMA scFv comprises 3 HCDR sequences having an amino acid sequence set forth in SEQ ID NO: 5 and/or 3 LCDR sequences having an amino acid sequence set forth in SEQ ID NO: 41. In some embodiments, the anti-BCMA scFv comprises an HCDR3 of SEQ ID NO: 3 and an LCDR3 of SEQ ID NO: 38. In certain embodiments, the anti-BCMA scFv comprises: an HCDR1 of SEQ ID NO: 1, an HCDR2 of SEQ ID NO: 2, and an HCDR3 of SEQ ID NO: 3. In certain embodiments, the anti-BCMA scFv comprises: an LCDR1 of SEQ ID NO: 32, an LCDR2 of SEQ ID NO: 35, and an LCDR3 of SEQ ID NO: 38. In certain embodiments, the anti-BCMA scFv comprises: an HCDR1 of SEQ ID NO: 1, an HCDR2 of SEQ ID NO: 2, an HCDR3 of SEQ ID NO: 3, an LCDR1 of SEQ ID NO: 32, an LCDR2 of SEQ ID NO: 35, and an LCDR3 of SEQ ID NO: 38.

In certain embodiments, the antibody disclosed herein is an anti-BCMA scFv antibody or an antigen-binding fragment thereof, which comprises an antigen-binding site having an amino acid sequence set forth in SEQ ID NO: 105 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 105. In one embodiment, the anti-BCMA scFv antibody is encoded by a nucleotide of SEQ ID NO: 106.

In certain embodiments, the anti-BCMA scFv antibody comprises a heavy chain variable region comprising an amino acid sequence of SEQ ID NO: 5 or an amino acid sequence having at least 90%, 92%, 95%, 97%, 98%, 99% or higher identity thereto, and a light chain variable region comprising an amino acid sequence of SEQ ID NO: 42 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 5. In certain embodiments, the anti-BCMA scFv comprises a VL having an amino acid sequence of SEQ ID NO: 42. In certain embodiments, the anti-BCMA scFv comprises a VH having an amino acid sequence set forth in SEQ ID NO: 5 and a VL having an amino acid sequence set forth in SEQ ID NO: 42. In certain embodiments, the anti-BCMA scFv comprises 3 HCDR sequences having an amino acid sequence set forth in SEQ ID NO: 5 and/or 3 LCDR sequences having an amino acid sequence set forth in SEQ ID NO: 42. In some embodiments, the anti-BCMA scFv comprises an HCDR3 of SEQ ID NO: 3 and an LCDR3 of SEQ ID NO: 39. In certain embodiments, the anti-BCMA scFv comprises: an HCDR1 of SEQ ID NO: 1, an HCDR2 of SEQ ID NO: 2, and an HCDR3 of SEQ ID NO: 3. In certain embodiments, the anti-BCMA scFv comprises: an LCDR1 of SEQ ID NO: 33, an LCDR2 of SEQ ID NO: 36, and an LCDR3 of SEQ ID NO: 39. In certain embodiments, the anti-BCMA scFv comprises: an HCDR1 of SEQ ID NO: 1, an HCDR2 of SEQ ID NO: 2, an HCDR3 of SEQ ID NO: 3, an LCDR1 of SEQ ID NO: 33, an LCDR2 of SEQ ID NO: 36, and an LCDR3 of SEQ ID NO: 39.

In certain embodiments, the antibody disclosed herein is an anti-BCMA scFv antibody or an antigen-binding fragment thereof, which comprises an antigen-binding site having an amino acid sequence set forth in SEQ ID NO: 108 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 108. In one embodiment, the anti-BCMA scFv antibody is encoded by a nucleotide of SEQ ID NO: 109.

In certain embodiments, the anti-BCMA scFv antibody comprises a heavy chain variable region comprising an amino acid sequence of SEQ ID NO: 10 or an amino acid sequence having at least 90%, 92%, 95%, 97%, 98%, 99% or higher identity thereto, and a light chain variable region comprising an amino acid sequence of SEQ ID NO: 46 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 10. In certain embodiments, the anti-BCMA scFv comprises a VL having an amino acid sequence of SEQ ID NO: 46. In certain embodiments, the anti-BCMA scFv comprises a VH having an amino acid sequence set forth in SEQ ID NO: 10 and a VL having an amino acid sequence set forth in SEQ ID NO: 46. In certain embodiments, the anti-BCMA scFv comprises 3 HCDR sequences having an amino acid sequence set forth in SEQ ID NO: 10 and/or 3 LCDR sequences having an amino acid sequence set forth in SEQ ID NO: 46. In some embodiments, the anti-BCMA scFv comprises an HCDR3 of SEQ ID NO: 9 and an LCDR3 of SEQ ID NO: 45. In certain embodiments, the anti-BCMA scFv comprises: an HCDR1 of SEQ ID NO: 7, an HCDR2 of SEQ ID NO: 8, and an HCDR3 of SEQ ID NO: 9. In certain embodiments, the anti-BCMA scFv comprises: an LCDR1 of SEQ ID NO: 32, an LCDR2 of SEQ ID NO: 44, and an LCDR3 of SEQ ID NO: 45. In certain embodiments, the anti-BCMA scFv comprises: an HCDR1 of SEQ ID NO: 7, an HCDR2 of SEQ ID NO: 8, an HCDR3 of SEQ ID NO: 9, an LCDR1 of SEQ ID NO: 32, an LCDR2 of SEQ ID NO: 44, and an LCDR3 of SEQ ID NO: 45.

In certain embodiments, the antibody disclosed herein is an anti-BCMA scFv antibody or an antigen-binding fragment thereof, which comprises an antigen-binding site having an amino acid sequence set forth in SEQ ID NO: 111 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 111. In one embodiment, the anti-BCMA scFv antibody is encoded by a nucleotide of SEQ ID NO: 112.

In certain embodiments, the anti-BCMA scFv antibody comprises a heavy chain variable region comprising an amino acid sequence of SEQ ID NO: 16 or an amino acid sequence having at least 90%, 92%, 95%, 97%, 98%, 99% or higher identity thereto, and a light chain variable region comprising an amino acid sequence of SEQ ID NO: 50 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 16. In certain embodiments, the anti-BCMA scFv comprises a VL having an amino acid sequence of SEQ ID NO: 50. In certain embodiments, the anti-BCMA scFv comprises a VH having an amino acid sequence set forth in SEQ ID NO: 16 and a VL having an amino acid sequence set forth in SEQ ID NO: 50. In certain embodiments, the anti-BCMA scFv comprises 3 HCDR sequences having an amino acid sequence set forth in SEQ ID NO: 16 and/or 3 LCDR sequences having an amino acid sequence set forth in SEQ ID NO: 50. In some embodiments, the anti-BCMA scFv comprises an HCDR3 of SEQ ID NO: 13 and an LCDR3 of SEQ ID NO: 49. In certain embodiments, the anti-BCMA scFv comprises: an HCDR1 of SEQ ID NO: 11, an HCDR2 of SEQ ID NO: 12, and an HCDR3 of SEQ ID NO: 13. In certain embodiments, the anti-BCMA scFv comprises: an LCDR1 of SEQ ID NO: 47, an LCDR2 of SEQ ID NO: 48, and an LCDR3 of SEQ ID NO: 49. In certain embodiments, the anti-BCMA scFv comprises: an HCDR1 of SEQ ID NO: 11, an HCDR2 of SEQ ID NO: 12, an HCDR3 of SEQ ID NO: 13, an LCDR1 of SEQ ID NO: 47, an LCDR2 of SEQ ID NO: 48, and an LCDR3 of SEQ ID NO: 49.

In certain embodiments, the antibody disclosed herein is an anti-BCMA scFv antibody or an antigen-binding fragment thereof, which comprises an antigen-binding site having an amino acid sequence set forth in SEQ ID NO: 114 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 114. In one embodiment, the anti-BCMA scFv antibody is encoded by a nucleotide of SEQ ID NO: 115.

In certain embodiments, the anti-BCMA scFv antibody comprises a heavy chain variable region comprising an amino acid sequence of SEQ ID NO: 17 or an amino acid sequence having at least 90%, 92%, 95%, 97%, 98%, 99% or higher identity thereto, and a light chain variable region comprising an amino acid sequence of SEQ ID NO: 58 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 17. In certain embodiments, the anti-BCMA scFv comprises a VL having an amino acid sequence of SEQ ID NO: 58. In certain embodiments, the anti-BCMA scFv comprises a VH having an amino acid sequence set forth in SEQ ID NO: 17 and a VL having an amino acid sequence set forth in SEQ ID NO: 58. In certain embodiments, the anti-BCMA scFv comprises 3 HCDR sequences having an amino acid sequence set forth in SEQ ID NO: 17 and/or 3 LCDR sequences having an amino acid sequence set forth in SEQ ID NO: 58. In some embodiments, the anti-BCMA scFv comprises an HCDR3 of SEQ ID NO: 14 and an LCDR3 of SEQ ID NO: 55. In certain embodiments, the anti-BCMA scFv comprises: an HCDR1 of SEQ ID NO: 11, an HCDR2 of SEQ ID NO: 12, and an HCDR3 of SEQ ID NO: 14. In certain embodiments, the anti-BCMA scFv comprises: an LCDR1 of SEQ ID NO: 51, an LCDR2 of SEQ ID NO: 54, and an LCDR3 of SEQ ID NO: 55. In certain embodiments, the anti-BCMA scFv comprises: an HCDR1 of SEQ ID NO: 11, an HCDR2 of SEQ ID NO: 12, an HCDR3 of SEQ ID NO: 14, an LCDR1 of SEQ ID NO: 51, an LCDR2 of SEQ ID NO: 54, and an LCDR3 of SEQ ID NO: 55.

In certain embodiments, the antibody disclosed herein is an anti-BCMA scFv antibody or an antigen-binding fragment thereof, which comprises an antigen-binding site having an amino acid sequence set forth in SEQ ID NO: 120 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 120. In one embodiment, the anti-BCMA scFv antibody is encoded by a nucleotide of SEQ ID NO: 121.

In certain embodiments, the anti-BCMA scFv antibody comprises a heavy chain variable region comprising an amino acid sequence of SEQ ID NO: 23 or an amino acid sequence having at least 90%, 92%, 95%, 97%, 98%, 99% or higher identity thereto, and a light chain variable region comprising an amino acid sequence of SEQ ID NO: 64 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 23. In certain embodiments, the anti-BCMA scFv comprises a VL having an amino acid sequence of SEQ ID NO: 64. In certain embodiments, the anti-BCMA scFv comprises a VH having an amino acid sequence set forth in SEQ ID NO: 23 and a VL having an amino acid sequence set forth in SEQ ID NO: 64. In certain embodiments, the anti-BCMA scFv comprises 3 HCDR sequences having an amino acid sequence set forth in SEQ ID NO: 23 and/or 3 LCDR sequences having an amino acid sequence set forth in SEQ ID NO: 64. In some embodiments, the anti-BCMA scFv comprises an HCDR3 of SEQ ID NO: 22 and an LCDR3 of SEQ ID NO: 63. In certain embodiments, the anti-BCMA scFv comprises: an HCDR1 of SEQ ID NO: 20, an HCDR2 of SEQ ID NO: 21, and an HCDR3 of SEQ ID NO: 22. In certain embodiments, the anti-BCMA scFv comprises: an LCDR1 of SEQ ID NO: 61, an LCDR2 of SEQ ID NO: 62, and an LCDR3 of SEQ ID NO: 63. In certain embodiments, the anti-BCMA scFv comprises: an HCDR1 of SEQ ID NO: 20, an HCDR2 of SEQ ID NO: 21, an HCDR3 of SEQ ID NO: 22, an LCDR1 of SEQ ID NO: 61, an LCDR2 of SEQ ID NO: 62, and an LCDR3 of SEQ ID NO: 63.

In certain embodiments, the antibody disclosed herein is an anti-BCMA scFv antibody or an antigen-binding fragment thereof, which comprises an antigen-binding site having an amino acid sequence set forth in SEQ ID NO: 117 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 117. In one embodiment, the anti-BCMA scFv antibody is encoded by a nucleotide of SEQ ID NO: 118.

In certain embodiments, the anti-BCMA scFv antibody comprises a heavy chain variable region comprising an amino acid sequence of SEQ ID NO: 27 or an amino acid sequence having at least 90%, 92%, 95%, 97%, 98%, 99% or higher identity thereto, and a light chain variable region comprising an amino acid sequence of SEQ ID NO: 59 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 27. In certain embodiments, the anti-BCMA scFv comprises a VL having an amino acid sequence of SEQ ID NO: 59. In certain embodiments, the anti-BCMA scFv comprises a VH having an amino acid sequence set forth in SEQ ID NO: 27 and a VL having an amino acid sequence set forth in SEQ ID NO: 59. In certain embodiments, the anti-BCMA scFv comprises 3 HCDR sequences having an amino acid sequence set forth in SEQ ID NO: 27 and/or 3 LCDR sequences having an amino acid sequence set forth in SEQ ID NO: 59. In some embodiments, the anti-BCMA scFv comprises an HCDR3 of SEQ ID NO: 26 and an LCDR3 of SEQ ID NO: 56. In certain embodiments, the anti-BCMA scFv comprises: an HCDR1 of SEQ ID NO: 24, an HCDR2 of SEQ ID NO: 25, and an HCDR3 of SEQ ID NO: 26. In certain embodiments, the anti-BCMA scFv comprises: an LCDR1 of SEQ ID NO: 52, an LCDR2 of SEQ ID NO: 62, and an LCDR3 of SEQ ID NO: 56. In certain embodiments, the anti-BCMA scFv comprises: an HCDR1 of SEQ ID NO: 24, an HCDR2 of SEQ ID NO: 25, an HCDR3 of SEQ ID NO: 26, an LCDR1 of SEQ ID NO: 52, an LCDR2 of SEQ ID NO: 62, and an LCDR3 of SEQ ID NO: 56.

In certain embodiments, the antibody disclosed herein is an anti-BCMA scFv antibody or an antigen-binding fragment thereof, which comprises an antigen-binding site having an amino acid sequence set forth in SEQ ID NO: 123 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 123. In one embodiment, the anti-BCMA scFv antibody is encoded by a nucleotide of SEQ ID NO: 124.

In certain embodiments, the anti-BCMA scFv antibody comprises a heavy chain variable region comprising an amino acid sequence of SEQ ID NO: 27 or an amino acid sequence having at least 90%, 92%, 95%, 97%, 98%, 99% or higher identity thereto, and a light chain variable region comprising an amino acid sequence of SEQ ID NO: 71 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 27. In certain embodiments, the anti-BCMA scFv comprises a VL having an amino acid sequence of SEQ ID NO: 71. In certain embodiments, the anti-BCMA scFv comprises a VH having an amino acid sequence set forth in SEQ ID NO: 27 and a VL having an amino acid sequence set forth in SEQ ID NO: 71. In certain embodiments, the anti-BCMA scFv comprises 3 HCDR sequences having an amino acid sequence set forth in SEQ ID NO: 27 and/or 3 LCDR sequences having an amino acid sequence set forth in SEQ ID NO: 71. In some embodiments, the anti-BCMA scFv comprises an HCDR3 of SEQ ID NO: 26 and an LCDR3 of SEQ ID NO: 68. In certain embodiments, the anti-BCMA scFv comprises: an HCDR1 of SEQ ID NO: 24, an HCDR2 of SEQ ID NO: 25, and an HCDR3 of SEQ ID NO: 26. In certain embodiments, the anti-BCMA scFv comprises: an LCDR1 of SEQ ID NO: 65, an LCDR2 of SEQ ID NO: 62, and an LCDR3 of SEQ ID NO: 68. In certain embodiments, the anti-BCMA scFv comprises: an HCDR1 of SEQ ID NO: 24, an HCDR2 of SEQ ID NO: 25, an HCDR3 of SEQ ID NO: 26, an LCDR1 of SEQ ID NO: 65, an LCDR2 of SEQ ID NO: 62, and an LCDR3 of SEQ ID NO: 68.

In certain embodiments, the antibody disclosed herein is an anti-BCMA scFv antibody or an antigen-binding fragment thereof, which comprises an antigen-binding site having an amino acid sequence set forth in SEQ ID NO: 126 or a variant thereof, and specifically binds to a BCMA polypeptide (e.g., a BCMA polypeptide having an amino acid sequence of SEQ ID NO: 74, or a fragment thereof). In some embodiments, the amino acid sequence of the variant has at least 90%, 92%, 95%, 97%, 98%, 99% or higher identity to an amino acid sequence of SEQ ID NO: 126. In one embodiment, the anti-BCMA scFv antibody is encoded by a nucleotide of SEQ ID NO: 127.

In certain embodiments, the anti-BCMA scFv antibody comprises a heavy chain variable region comprising an amino acid sequence of SEQ ID NO: 27 or an amino acid sequence having at least 90%, 92%, 95%, 97%, 98%, 99% or higher identity thereto, and a light chain variable region comprising an amino acid sequence of SEQ ID NO: 72 or an amino acid sequence having at least 90%, 92%, 95%, 97%, 98%, 99% or higher identity thereto, and optionally a linker, such as a linker peptide, between the heavy chain variable region and the light chain variable region. In certain embodiments, the linker comprises an amino acid sequence of SEQ ID NO: 93.

In certain embodiments, the anti-BCMA scFv comprises a VH having an amino acid sequence of SEQ ID NO: 27. In certain embodiments, the anti-BCMA scFv comprises a VL having an amino acid sequence of SEQ ID NO: 72. In certain embodiments, the anti-BCMA scFv comprises a VH having an amino acid sequence set forth in SEQ ID NO: 27 and a VL having an amino acid sequence set forth in SEQ ID NO: 72. In certain embodiments, the anti-BCMA scFv comprises 3 HCDR sequences having an amino acid sequence set forth in SEQ ID NO: 27 and/or 3 LCDR sequences having an amino acid sequence set forth in SEQ ID NO: 72. In some embodiments, the anti-BCMA scFv comprises an HCDR3 of SEQ ID NO: 26 and an LCDR3 of SEQ ID NO: 69. In certain embodiments, the anti-BCMA scFv comprises: an HCDR1 of SEQ ID NO: 24, an HCDR2 of SEQ ID NO: 25, and an HCDR3 of SEQ ID NO: 26. In certain embodiments, the anti-BCMA scFv comprises: an LCDR1 of SEQ ID NO: 66, an LCDR2 of SEQ ID NO: 62, and an LCDR3 of SEQ ID NO: 69. In certain embodiments, the anti-BCMA scFv comprises: an HCDR1 of SEQ ID NO: 24, an HCDR2 of SEQ ID NO: 25, an HCDR3 of SEQ ID NO: 26, an LCDR1 of SEQ ID NO: 66, an LCDR2 of SEQ ID NO: 62, and an LCDR3 of SEQ ID NO: 69.

III. scFv-Fc Antibodies

Antibodies with Fc regions have several advantages, including but not limited to: effector functions mediated by Fc region, such as immunological activities CDC and ADCC; formation of bivalent antibodies via the dimerization functions of Fc region, thereby providing high antigen-binding affinity, and/or changing plasma half-life and renal clearance; internalizing bivalent antibodies at a different rate from those of monovalent Fab and scFv antibodies, thus changing immune functions or carrier functions. For example, alpha emitters do not require internalization to kill target cells, but many drugs and toxins would benefit from internalization using immune complexes.

Thus, in a preferred embodiment, provided is an scFv-Fc antibody formed by fusion of the single-chain scFv antibody disclosed herein with an antibody Fc region. In some embodiments, the scFv-Fc antibody comprises the single-chain scFv antibody disclosed herein and a wild-type or modified Fc region. In a preferred embodiment, the scFv-Fc antibody comprises, from N terminus to C terminus, Fc-VH-linker-VL or Fc-VL-linker-VH, or preferably, VH-linker-VL-Fc or VL-linker-VH-Fc. In a preferred embodiment, the Fc region is connected to a variable region (VH or VL) via a hinge region. In some embodiments, the Fc region is an Fc region from a human immunoglobulin, preferably a human IgG1 or IgG4 Fc region. In a preferred embodiment, the Fc region has an amino acid sequence set forth in SEQ ID NO: 132, or an amino acid sequence comprising at least one, two or three but no more than 20, 10 or 5 amino acid alterations compared to the amino acid sequence of SEQ ID NO: 132, or a sequence having at least 95-99% identity to the amino acid sequence of SEQ ID NO: 132. In some embodiments, the single-chain scFv antibody disclosed herein is connected to the Fc region by a hinge region. In one embodiment, the hinge region is a C8 hinge region comprising, e.g., an amino acid sequence set forth in SEQ ID NO: 95, or an amino acid sequence comprising at least one, two or three but no more than 5 amino acid alterations compared to the amino acid sequence of SEQ ID NO: 95.

In some preferred embodiments, provided are such antibodies that specifically bind to a BCMA polypeptide (e.g., a BCMA polypeptide having an amino acid sequence set forth in SEQ ID NO: 74 or a fragment thereof) and comprise an amino acid sequence selected from SEQ ID NOs: 101, 104, 107, 110, 113, 116, 119, 122, 125 and 128, or an amino acid sequence comprising at least one, two, or three but no more than 20, 10, or 5 amino acid alterations compared thereto, or an amino acid sequence having at least 80%, 85%, 90%, 92%, 95%, 97%, 98%, 99% or higher identity thereto.

The amino acid sequences of some exemplary ScFv-Fc antibodies disclosed herein, and the amino acid and nucleotide sequences of single-chain scFvs antibodies for constructing the same are listed in Table 3 below. Table 3 also shows the amino acid and nucleotide sequences of a reference scFv-Fc recombinant single-chain antibody constructed on the basis of the description of US20170226216A1. The amino acid and nucleotide sequences of linkers and hinges used in the scFv-Fc antibodies are shown in FIG. 8.

TABLE 3

| Antibody | Amino acid sequence of scEv | DNA sequence of scEv | Amino acid sequence of scFv-hFc |
|---|---|---|---|
| ADI-34848 scFv-hFc | SEQ ID NO:99 | SEQ ID NO:100 | SEQ ID NO:101 |
| ADI-34849 scFv-hFc | SEQ ID NO:102 | SEQ ID NO:103 | SEQ ID NO:104 |
| ADI-34850 scFv-hFc | SEQ ID NO:105 | SEQ ID NO:106 | SEQ ID NO:107 |
| ADI-34854 scFv-hFc | SEQ ID NO:108 | SEQ ID NO:109 | SEQ ID NO:110 |
| ADI-34846 scFv-hFc | SEQ ID NO:111 | SEQ ID NO:112 | SEQ ID NO:113 |
| ADI-34857 scFv-hFc | SEQ ID NO:114 | SEQ ID NO:115 | SEQ ID NO:116 |
| ADI-34859 scFv-hFc | SEQ ID NO:117 | SEQ ID NO:118 | SEQ ID NO:119 |
| ADI-34832 scFv-hFc | SEQ ID NO:120 | SEQ ID NO:121 | SEQ ID NO:122 |
| ADI-34860 scFv-hFc | SEQ ID NO:123 | SEQ ID NO:124 | SEQ ID NO:125 |
| ADI-34861 scFv-hFc | SEQ ID NO:126 | SEQ ID NO:127 | SEQ ID NO:128 |
| Reference scFv-hFc | SEQ ID NO:129 | SEQ ID NO:130 | SEQ ID NO:131 |

In some embodiments, the scFv-Fc antibody disclosed herein has an effector function. The term "effector function" refers to a biological activity attributable to the antibody Fc-region that varies with the class of antibody. There are five major classes of antibodies: IgA, IgD, IgE, IgG, and IgM, some of which can be further divided into subclasses (isotypes), e.g., IgG1, IgG2, IgG3, IgG4, IgA1, and IgA2. The heavy chain constant domains that correspond to different classes of immunoglobulins are referred to as α, δ, ε, γ, and μ, respectively. The effector function of the antibody includes, for example, but not limited to, C1q binding and complement dependent cytotoxicity (CDC); Fc receptor binding; antibody-dependent cell-mediated cytotoxicity (ADCC); phagocytosis; down-regulation of cell surface receptors (e.g., B-cell receptors); and B-cell activation. In some embodiments, the scFv-Fc antibodies disclosed herein block and inhibit the growth of cells (particularly MM cells) expressing BCMA, and/or kill the cells by effector cell-mediated cytotoxicity (ADCC).

In certain embodiments, the Fc region may comprise an Fc-region having one or more amino acid substitutions that improve the ADCC activity, e.g., substitutions at positions 298, 333 and/or 334 (EU numbering of residues) of the Fc-region. In some embodiments, the Fc-region can also be altered to result in altered (i.e., increased or decreased) C1q binding and/or complement dependent cytotoxicity (CDC) (see, e.g., U.S. Pat. No. 6,194,551, WO 99/51642 and Idusogie, E. E. et al., J. Immunol. 164 (2000) 4178-4184).

In other embodiments, the Fc region can be altered to increase or decrease its glycosylation degree and/or alter its glycosylation pattern. Addition or deletion of glycosylation sites of the Fc region can be conveniently achieved by producing or removing one or more glycosylation sites through amino acid sequence alteration. For example, one or more amino acid substitutions may be made to eliminate one or more glycosylation sites, thereby eliminating glycosylation at the sites. Antibodies with altered classes of glycosylation can be prepared, such as low-fucosylated or non-fucosylated antibodies with reduced content of fucosyl residues or antibodies with increased bisecting GlcNac structures. Such altered glycosylation patterns have shown the ability to increase ADCC of antibodies.

Thus, in some preferred embodiments, provided are antibodies with low-fucosylated or non-fucosylated Fc regions, which can significantly increase the binding affinity of the antibody Fc domains to Fcγ receptors (e.g., Fcγ RIIIa) expressed on effector cells, enabling enhanced antibody-dependent cell-mediated cytotoxicity (ADCC) activity of the antibodies. For example, the content of fucose in the antibodies may be 1% to 80%, 1% to 65%, 5% to 65%, or 20% to 40%. The content of fucose can be determined by calculating the average content of fucose in a sugar chain at Asn297, relative to the sum of all Asn297-linked glycostructures (e.g. complex, hybrid and high mannose structures) as measured by MALDI-TOF® mass spectrometry, for example, as described in WO 2008/077546. Asn297 refers to the asparagine residue at about position 297 (EU numbering of Fc region residues) in the Fc region; however, Asn297 may also be located about ±3 amino acid positions upstream or downstream of position 297, i.e., between positions 294 and 300, due to minor sequence variations in the antibody. See, e.g., US 2003/0157108; US 2004/0093621. Examples of publications related to "non-fucosylated" or "low-fucosylated" antibody variants also include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. mol. biol. 336 (2004) 1239-1249; Yamane-ohniki, N. et al., Biotech. Bioeng. 87:614 (2004) 614-622. Such antibody variants can be produced in cell lines capable of producing non-fucosylated or low-fucosylated antibodies. Examples of such cells include protein fucosylation deficient Lec13 CHO cells (Ripka, J. et al., Arch. Biochem. Biophys. 249 (1986): 533-545; US 2003/0157108; and WO 2004/056312, especially example 11); and gene knockout cell lines such as α-1,6-fucosyltransferase gene FUT8 knockout CHO cells (see, e.g., Yamane-Ohnuki, N. et al., Biotech. Bioeng. 87:614 (2004) 614-622; Kanda, Y. et al., Biotechnol. Bioeng. 94 (2006) 680-688; and WO 2003/085107). For another example, cell lines Ms704, Ms705 and Ms709 lack fucosyltransferase gene FUT8 (α(1,6)-fucosyltransferase), so that antibodies lacking fucose can be expressed in the cell lines Ms704, Ms705 and Ms709. Furthermore, in EP 1,176, 195, cell lines with functionally disrupted FUT8 genes are described, and antibodies expressed in the cell lines are low-fucosylated. Alternatively, fucosidase may also be used to cleave off fucose residues from the antibodies; for example, fucosidase, α-L-fucosidase, removes fucosyl residues from antibodies (Tarentino et al. (1975) Biochem. 14:5516-23).

Furthermore, antibody variants with bisected oligosaccharides, e.g., antibodies in which biantennary oligosaccharides attached to the Fc regions are bisected by GlcNAc, are also considered herein. The antibody variants may have reduced fucosylation and/or an increased ADCC function. Examples of such antibody variants are described in, for example, WO 2003/011878; U.S. Pat. No. 6,602,684; and US 2005/0123546. Herein, an antibody variant having at least one galactose residue in the oligosaccharide attached to the Fc region is also considered. The antibody variants may have an increased CDC function. Such antibody variants are described, for example, in WO 1997/30087; WO 1998/58964; and WO 1999/22764.

Non-limiting examples of in vitro assays for assessing the ADCC activity of a target molecule are described in U.S. Pat. No. 5,500,362 (see, e.g., Hellstrom, I. et al., Proc. Nat'l Acad. Sci. USA 83 (1986) 7059-7063; Hellstrom, I. et al., Proc. Nat'l Acad. Sci. USA 82 (1985) 1499-1502); and U.S. Pat. No. 5,821,337 (see Bruggemann, M. et al., J. Exp. Med. 166 (1987) 1351-1361). Alternatively, non-radioactive assays (see, e.g., ACTI™ non-radioactive cytotoxicity assays (Celltechnology, Inc. Mountain View, Calif.) and CytoTox96® non-radioactive cytotoxicity assays (Promega, Madison, Wis.) for flow cytometry) may be employed. Effector cells suitable for use in these assays include peripheral blood mononuclear cells (PBMC) and natural killer (NK) cells. Alternatively. or additionally, the ADCC activity of the target molecule may be assessed in vivo, for example, in an animal model as disclosed in Clynes, R. et al., Proc. Nat'l Acad. Sci. USA 95(1998) 652-656. To assess complement activation, a CDC assay may be conducted (see, e.g., Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). C1q binding assays may also be conducted to confirm C1q binding and CDC activity of antibodies. See, e.g., C1q and C3c binding ELISA in WO 2006/029879 and WO 2005/100402.

In certain embodiments, the invention also considers an antibody variant that possesses some but not all effector functions, which makes it a desirable candidate for application in which the half-life period of the antibody in vivo is important yet certain effector functions (such as complement and ADCC) are unnecessary or deleterious. In vitro and/or in vivo assays can be conducted to confirm the reduction/depletion of CDC and/or ADCC activity. For example, Fc receptor (FcR) binding assays can be conducted to ensure that the antibody lacks FcγR binding (hence likely lacking ADCC activity), but retains FcRn binding ability. For example, the Fc region may comprise a mutation that eliminates or reduces effector functions, such as the human IgG1 Fc region with mutations P329G and/or L234A and L235A, or the human IgG4 Fc region with mutations P329G and/or S228P and L235E.

In some embodiments, the scFv-Fc antibody disclosed herein may form a bivalent antibody by dimerization of an Fc region, and may further have increased overall affinity and stability, or form poly-specificity such as bispecificity. For example, the Fc region may comprise i) a homodimeric Fc-region of a subclass human IgG1, or ii) a homodimeric Fc-region of a subclass human IgG4, or iii) a heterodimeric Fc-region, wherein a) one Fc-region polypeptide comprises mutation T366W and the other Fc-region polypeptide comprises mutations T366S, L368A and Y407V, or b) one Fc-region polypeptide comprises mutations T366W and Y349C and the other Fc-region polypeptide comprises mutations T366S, L368A, Y407V and S354C, or c) one Fc-region polypeptide comprises mutations T366W and S354C and the other Fc-region polypeptide comprises mutations T366S, L368A, Y407V and Y349C.

In some embodiments, the scFv-Fc recombinant antibodies disclosed herein may be directly fused or conjugated to other molecules, including, but not limited to, fluorescent dyes, cytotoxins, radioisotopes, etc., by virtue of the Fc regions, e.g., for antigen quantification studies, antibody immobilization for affinity measurements, targeted delivery of therapeutic agents, Fc-mediated cytotoxicity assays using immune effector cells, and many other uses.

B. Polynucleotides and Hosts

In one aspect, the invention provides a substantially purified nucleic acid molecule encoding a polypeptide comprising a segment or a domain of an antibody chain that binds to BCMA as described above. In some embodiments, the nucleic acid molecule disclosed herein encodes an antibody chain (e.g., a chain of any of the antibodies disclosed herein, including single-chain scFv antibodies and scFv-Fc antibodies, and the fragments thereof) that binds to BCMA.

Some nucleic acids disclosed herein comprise a nucleotide sequence encoding a heavy chain variable region or a variant thereof of any one of the antibodies shown in Table 1, and/or a light chain variable region or a variant thereof of the corresponding antibody shown in Table 1. In one specific embodiment, the nucleic acid molecule is a DNA VH sequence and/or a DNA VL sequence listed in Table 1. Some other nucleic acid molecules disclosed herein comprise a nucleotide sequence that is substantially identical (e.g., at least 65%, 80%, 95%, or 99% identical) to the nucleotide sequence of the nucleic acid molecule shown in Table 1. The polypeptides encoded by the polynucleotides can show BCMA antigen-binding ability when expressed in a suitable expression vector.

Also provided in the invention is a polynucleotide encoding at least one CDR region and typically all three CDR regions from a heavy chain VH sequence or a light chain VL sequence of the antibody that binds to BCMA as described above. In some further embodiments, the polynucleotide encodes the complete or substantially complete variable region sequence of the heavy chain and/or the light chain of the antibody that binds to BCMA as described above.

As will be appreciated by those skilled in the art, each antibody or polypeptide amino acid sequence may be encoded by a variety of nucleic acid sequences because of codon degeneracy.

Some nucleic acid sequences disclosed herein comprise a nucleotide sequence encoding a heavy chain VH, wherein the nucleotide sequence comprises (i) the nucleotide sequence selected from SEQ ID NOs: 75-82 or a nucleotide sequence having e.g., at least 80%, 90% or 99% identity thereto. Some other nucleic acid sequences comprise a nucleotide sequence encoding a light chain VL, wherein the nucleotide sequence comprises the nucleotide sequence selected from SEQ ID NOs: 83-92 or a nucleotide sequence having e.g., at least 80%, 90% or 99% identity thereto.

In some embodiments, the nucleic acid sequence disclosed herein encodes any of the above single-chain scFv antibodies disclosed herein. In some embodiments, the nucleic acid sequence disclosed herein encoding an scFv antibody comprises a nucleotide sequence encoding a heavy chain VH sequence and a nucleotide sequence encoding a light chain VL sequence, wherein the two nucleotide sequences are selected from the group consisting of:

(i) a sequence of SEQ ID NO: 75 or a sequence substantially identical thereto, and a sequence of SEQ ID NO: 83 or a sequence substantially identical thereto;

(ii) a sequence of SEQ ID NO: 76 or a sequence substantially identical thereto, and a sequence of SEQ ID NO: 84 or 85 or a sequence substantially identical thereto;

(iii) a sequence of SEQ ID NO: 77 or a sequence substantially identical thereto, and a sequence of SEQ ID NO: 86 or a sequence substantially identical thereto;

(iv) a sequence of SEQ ID NO: 78 or a sequence substantially identical thereto, and a sequence of SEQ ID NO: 87 or a sequence substantially identical thereto;

(v) a sequence of SEQ ID NO: 79 or a sequence substantially identical thereto, and a sequence of SEQ ID NO: 88 or a sequence substantially identical thereto;

(vi) a sequence of SEQ ID NO: 80 or a sequence substantially identical thereto, and a sequence of SEQ ID NO: 89 or a sequence substantially identical thereto;

(vii) a sequence of SEQ ID NO: 81 or a sequence substantially identical thereto, and a sequence of SEQ ID NO: 90 or a sequence substantially identical thereto;

(viii) a sequence of SEQ ID NO: 82 or a sequence substantially identical thereto, and a sequence of SEQ ID NO: 91 or 92 or a sequence substantially identical thereto.

In one preferred embodiment, the nucleic acid disclosed herein encoding an scFv antibody further comprises a nucleotide sequence encoding a linker, such as a sequence set forth in SEQ ID NO: 94 or a sequence substantially identical thereto.

In one more preferred embodiment, the nucleic acid disclosed herein encoding an scFv antibody comprises a nucleotide sequence selected from the group consisting of SEQ ID NOs: 100, 103, 106, 109, 112, 115, 118, 121, 124 and 127, or a nucleotide sequence substantially identical thereto.

In any of the above embodiments, in one preferred aspect, a "substantially identical" nucleotide sequence refers to a sequence that has at least 80%, 85%, 90%, 91%, 92%, 93%, 94%, 95%, 96%, 97%, 98%, 99% or higher identity to a reference nucleotide sequence. The identity of nucleotide sequences can be determined using various sequence alignment methods well known in the art. BLAST sequence alignment search tools are available, for example, from the website of National Center for Biotechnology Information (NCBI), Bethesda, Md. Typically, determination of percent identity is conducted using the default parameters of NCBI Blast™.

These polynucleotide sequences can be produced by de novo solid phase DNA synthesis or by PCR mutagenesis of existing sequences (e.g., the sequences shown in tables 1-3) encoding antibodies or the fragments thereof that bind to BCMA. Direct chemical synthesis of nucleic acids can be accomplished by methods known in the art, such as the phosphotriester method in Narang et al., 1979, Meth. Enzymol. 68:90; the phosphodiester method in Brown et al., Meth. Enzymol. 68:109, 1979; the diethylphosphoramidite method of Beaucage et al., Tetra. Lett., 22:1859, 1981; and the solid phase support method in U.S. Pat. No. 4,458,066. Introduction of mutations into polynucleotide sequences by PCR can be conducted as described, for example, in PCR Technology: Principles and Applications for DNA Amplification, H. A. Erlich (eds.), Freeman Press, NY, N.Y., 1992; PCR Protocols: A Guide to Methods and Applications, Innis et al. (eds.), Academic Press, San Diego, Calif., 1990; Mattila et al., Nucleic Acids Res. 19:967, 1991; and Eckert et al., PCR Methods and Applications 1:17, 1991.

C. Preparation of Antibodies

Antibodies can be prepared using recombinant methods and compositions, for example, as described in U.S. Pat. No. 4,816,567.

In one embodiment, a vector comprising an isolated nucleic acid encoding the BCMA-binding antibody described herein is provided. The nucleic acid may encode an amino acid sequence comprising a VL of an antibody and/or an amino acid sequence comprising a VH of an antibody. In a further embodiment, the vector is an expression vector. In a further embodiment, a host cell comprising the nucleic acid is provided. In one embodiment, the host cell (e.g., has been transformed by the following vectors) comprises: (1) a vector comprising a nucleic acid encoding an amino acid sequence comprising the antibody VL and an amino acid sequence comprising the antibody VH, or (2) a first vector comprising a nucleic acid encoding an amino acid sequence comprising the antibody VL and a second vector comprising a nucleic acid encoding an amino acid sequence comprising the antibody VH. In one embodiment, the host cell is eukaryotic, such as a Chinese Hamster Ovary (CHO) cell, a HEK293 cell, or a lymphoid cell (e.g., a Y0, a NS0 and an Sp20 cell). In one embodiment, a method for preparing an anti-BCMA antibody is provided, wherein the method comprises the steps of culturing the host cell comprising a nucleic acid encoding the antibody as provided above under conditions suitable for antibody expression, and optionally isolating the antibody from the host cell (or the host cell culture medium).

With respect to recombinant production of the anti-BCMA antibody, a nucleic acid encoding the antibody, e.g., the nucleic acid described above, can be isolated and inserted into one or more vectors for further cloning and/or expressing in a host cell. The nucleic acid can be readily isolated and sequenced using conventional procedures (e.g., by using an oligonucleotide probe that is capable of binding specifically to genes encoding the heavy and light chain variable regions of the antibody).

A variety of expression vectors can be used to express polynucleotides encoding antibody chains (e.g., chains of any of the antibodies disclosed herein, including scFv antibodies and full-length antibodies) that bind to BCMA. Both viral-based expression vectors and non-viral expression vectors can be used to produce antibodies in mammalian host cells. Non-viral vectors and systems include plasmids, episomal vectors, and artificial chromosomes, and typically contain expression cassettes for expression of proteins or RNAs (see, e.g., Harrington et al., Nat Genet 15:345, 1997). Available viral vectors include vectors based on retroviruses, adenoviruses, adeno-associated viruses and herpes viruses, and vectors based on SV40, papillomaviruses, HBP EB viruses and vaccinia viruses, and semliki forest viruses (SFV). See, Smith, Annu. Rev. Microbiol. 49:807, 1995; and Rosenfeld et al., Cell 68:143, 1992.

The choice of an expression vector will depend on an intended host cell in which the vector is to be expressed. Typically, an expression vector contains a promoter operably linked to a polynucleotide encoding an antibody chain or a polypeptide that binds to BCMA. In addition to the promoter, other regulatory elements may also be required or desired for efficient expression of the antibody chain or the fragment thereof that binds to BCMA. These elements typically include ATG initiation codons and adjacent ribosome binding sites or other sequences. Furthermore, expression efficiency can be enhanced by the introduction of an enhancer suitable for the used cell system (see, e.g., Scharf et al, Results Probl. Cell Differ. 20:125, 1994; and Bittner et al., Meth. Enzymol., 153:516, 1987). For example, an SV40 enhancer or a CMV enhancer may be used to increase expression in mammalian host cells.

The expression vector may also provide a secretion signal sequence to form a fusion protein containing a BCMA-binding polypeptide. Alternatively, a BCMA-binding antibody/polypeptide sequence may be linked to a signal sequence prior to insertion into the vector. In one preferred embodiment, a signal peptide comprises the amino acid sequence set forth in SEQ ID NO: 133. A vector used to accept the sequence encoding light and heavy chain variable domains of the BCMA-binding antibody may sometimes also encode a constant region or a portion thereof. Such vectors allow a variable region to be expressed as a fusion protein fused with a constant region, thereby resulting in the production of a complete antibody or a fragment thereof. Typically, such constant regions are human constant regions such as human IgG1 Fc regions. In one preferred embodiment, the Fc region fused with the variable region comprises the amino acid sequence set forth in SEQ ID NO: 132.

Host cells suitable for cloning or expressing vectors include prokaryotic or eukaryotic cells. For example, antibodies can be produced in bacteria, particularly when glycosylation and Fc effector functions are not required. Expression of antibody fragments and polypeptides in bacteria is described in, e.g., U.S. Pat. Nos. 5,648,237, 5,789, 199, and 5,840,523 (and also described in Charlton, K. A., Methods in Molecular Biology, Vol. 248, Lo, B.K.C. (eds.), Humana Press, Totowa, N.J. (2003), pp. 245-254, which describes expression of antibody fragments in *E. coli*). After expression, the antibodies can be separated from bacterial cell paste in a soluble fraction and can be further purified. In addition to prokaryotes, eukaryotic microorganisms such as filamentous fungi or yeasts are cloning or expression hosts suitable for antibody-encoding vectors and include fungal and yeast strains in which glycosylation pathway has been "humanized", and this results in the production of antibodies with partially or fully human glycosylation patterns. See Gerngross, Nat. Biotech. 22 (2004) 1409-1414; and Li, H. et al., Nat. Biotech (2006) 24:210-215. Host cells suitable for expression of glycosylated antibodies may also be derived from multicellular organisms (invertebrates and vertebrates). Examples of invertebrate cells include plant and insect cells. Numerous baculovirus strains have been identified, which can be used in conjunction with insect cells, particularly for transfection of *Spodoptera frugiperda* cells. Plant cell cultures may also be used as hosts. See, e.g., U.S. Pat. Nos. 5,959,177, 6,040,498, 6,420,548, 7,125,978 and 6,417,429 (describing the PLANTIBODIES™ technology for the production of antibodies in transgenic plants). Vertebrate cells that can be used as hosts include, for example, suspension growth adapted available mammalian cell lines. Other examples of available mammalian host cell lines include SV40 transformed monkey kidney CV1 lines (COS- 7); human embryonic kidney lines (293 or 293 cells as described, for example, in Graham, F. L. et al., J. Gen Virol. 36 (1997) 59); baby hamster kidney cells (BHK); mouse Sertoli cells (e.g., TM4 cells as described in Mather, J. P., Biol. Reprod. 23 (1980) 243-251); monkey kidney cells (CV1); Vero cells (VERO-76); human cervical cancer cells (HELA); canine kidney cells (MDCK); buffalo rat hepatocytes (BRL 3A); human lung cells (W138); human hepatocytes (Hep G2); mouse mammary tumor (MMT 060562); TRI cells, such as those described in Mather, J. P. et al., Annals N.Y. Acad. Sci. 383 (1982) 44-68; MRC 5 cells; and FS4 cells. Other available mammalian host cell lines include Chinese Hamster Ovary (CHO) cells including DHFR-CHO cells (Urlaub, G. et al., Proc. Natl. Acad. Sci. USA 77 (1980) 4216-4220), and myeloma cell lines such as Y0, NS0 and Sp2/0. A review of some mammalian host cell lines suitable for producing an antibody is described in, e.g., Yazaki, P. and Wu, A. M., Methods in Molecular Biology, Vol. 248, Lo. B.K.C. (eds.), Humana Press, Totowa, N.J. (2004) pp. 255-268. In some preferred embodiments, mammalian host cells are used to express and produce antibody polypeptides disclosed herein that bind to BCMA.

D. Screening, Identification and Characterization of Antibodies

The anti-BCMA antibodies provided herein can be screened, identified, or characterized for their physical/chemical properties and/or biological activities by various assays known in the art.

Yeasts that bind with high affinity to a target antigen can be selected from a display library of yeasts expressing human antibodies. Various methods for presenting or displaying antibodies or fragments thereof on the yeast surface and screening for the library are described in, e.g., US 20110076752 A1; U.S. Pat. No. 9,845,464 B2; Boder and Wittrup, 1997, Nat. Biotechnol., 15, 553-557; Blasie et al., 2004, Gene, 342, 211-218; Sazinsky et al., 2008, Proc. Natl. Acad. Sci. USA, 105, 20167-20172; Tasumi et al., 2009, Proc. Natl. Acad. Sci. USA, 106, 12891-12896, Kontermann and Dubel, 2010, Antibody Engineering, Springer Protocols; Kuroda and Ueda 2011, Biotechnol. Lett., 33, 1-9; Rakestraw et al., 2011, PEDS, 24, 525-530; and Shao Rongguang et al. (eds.), Research and Use of Antibody Drugs, People's Medical Publishing House (2013). The yeast display library can be screened, for example, by the following non-limiting means in which the screening can first be conducted by magnetic activated cell sorting (MACS™). For example, a yeast population presenting IgG or antibody fragments can be contacted with biotinylated target antigens for a period of time, then washed and incubated with streptavidin magnetic beads (available from Miltenyi; Biotec), and then yeast cells binding to the target antigens are captured on an LS magnetic column (available from Miltenyi; Biotec) and enriched. Thereafter, multiple rounds of enrichment can be conducted by FACS techniques. In FACS sorting, the yeast population can be contacted with the biotinylated target antigens with reduced concentrations (to screen for high affinity antibodies) or antigen homologues from different species (to screen for antibodies with a propensity to cross-reactivity of different species), followed by cell washing, resuspension in a two-standard solution (e.g., a mixture of streptavidin-PE and anti-human LC-FITC), incubation on ice, cell washing, and resuspension in a buffer such as a FACS wash buffer, and then yeast cells with LC-FITC positive (IgG presentation) and streptavidin-PE positive (target binding) phenotypes are sorted out on a flow cytometer such as FACSAria™ (BD Bioscience) for further propagation and selection. In FACS sorting, a negative selection reagent, such as a poly-specificity reagent (PSR) described in Xu et al. (Protein Engineering, Design & Selection, 2013, Vol 26, No. 10, pp 663-670), instead of the target antigen, can also be used to incubate with IgG-presenting yeasts to attenuate non-specific binding of antibodies and subsequent druggability concern by using the same two-standard solution and FACS sorting technique described above.

For the identification of antibodies, the antibodies disclosed herein can be identified or characterized with respect to the antigen binding activity thereof, e.g., by known methods such as ELISA, αLISA, western blots, antibodies or reverse phase arrays or the like, as well as the methods described in the examples.

For example, antibodies can be spotted on a glass or nitrocellulose chip. Slides are blocked and incubated with a BCMA-containing solution, washed to remove antibodies not binding to BCMA, and detected for antibodies that bind to BCMA by using corresponding fluorescently labeled secondary antibodies. Fluorescence signals are measured by a fluorescence slide scanner. Similarly, for a reverse phase array, recombinant BCMA, cell supernatant, cell or tissue lysate, body fluid and the like are spotted on a glass or nitrocellulose chip. Slides are blocked, and the array is incubated with antibodies directed against specific epitopes on BCMA. The antibodies not binding to BCMA are washed away, and the antibodies that bind to BCMA are detected by using corresponding fluorescently labeled secondary antibodies. Fluorescence signals are measured by a fluorescence slide scanner (Dernick, G. et al., J. Lipid Res., 52(2011) 2323-2331).

Antibodies can also be detected using a ForteBio™ assay. A ForteBio™ affinity assay can be conducted according to the method (Estep, P et al., High throughput solution Based measurement of antibody-antigen affinity and epitope binding. MAbs, 2013.5(2): p. 270-8) known in the art. For example, an AHQ Sensor® can be equilibrated for 30 minutes off-line in an assay buffer, and then detected online for 60 seconds to establish a baseline. Thereafter, the AHQ Sensor®, loaded on-line with purified antibodies, is exposed to 100 nM antigens for 5 minutes, and then transferred to the assay buffer for 5-min off-line measurement. Kinetic analysis is conducted using a 1:1 binding model.

Binding of antibodies to cells expressing BCMA on the surface can also be detected by flow cytometry. For example, H929 cells expressing BCMA can be incubated with serially diluted antibodies in PBS 1% BSA on ice for a period of time (e.g., 30 minutes), and then incubated with secondary antibodies (e.g., phycobilin-labeled secondary antibodies) in PBS 1% BSA on ice for a period of time (e.g., 30 minutes) in the absence of light. Then the cells are analyzed by flow cytometry after cell washing. The flow cytometry can be conducted on Accuri™ C6 system (BD Biosciences) and EC50 value is calculated using Graphpad software.

E. Fusions and Conjugates

In yet another aspect, the invention provides a fusion or conjugate comprising the antibody disclosed herein. The fusion or conjugate can be produced by fusing or conjugating the antibody disclosed herein to a heterologous molecule. In some embodiments, the antibody polypeptide disclosed herein may be fused or conjugated with one or more heterologous molecules, and the heterologous molecules include, but not limited to, proteins/polypeptides/peptides, labels, drugs, and cytotoxic agents. Methods for fusion or conjugation of proteins, polypeptides, peptides or chemical molecules with the antibody are known in the art. See, e.g., U.S. Pat. Nos. 5,336,603 and 5,622,929 and EP 367,166.

In one embodiment, the antibody disclosed herein is recombinantly fused with a heterologous protein, polypeptide or peptide to form a fusion protein. In yet another embodiment, the antibody disclosed herein is conjugated with a protein or non-protein molecule to produce a conjugate.

In some embodiments, the antibody disclosed herein may be fused or conjugated with a heterologous molecule in the form of a full-length antibody or an antibody fragment. In one preferred embodiment, the single-chain scFv antibody disclosed herein is used for fusion or conjugation. In a further preferred embodiment, the fusion protein comprising the single-chain scFv disclosed herein is provided. Such fusion proteins can be readily prepared by recombinant methods known in the art. In yet another preferred embodiment, a conjugate comprising the single-chain scFv disclosed herein is provided, e.g., a conjugate comprising the scFv disclosed herein and a non-protein drug molecule.

Linkers can be used to covalently link different entities in the fusions and/or conjugates disclosed herein. Linkers include chemical linkers or single-chain peptide linkers. In some embodiments, the single-chain antibody disclosed herein, e.g., an scFv antibody, is fused to another peptide fragment or protein via a peptide linker. In some embodiments, the single-chain antibody disclosed herein, e.g., an scFv antibody, is conjugated to another molecule, e.g., a label or a drug molecule, via a chemical linker.

Peptide linkers that may be used to form the antibody disclosed herein include peptides consisting of amino acid residues. Such peptide linkers are generally flexible, allowing the antigen-binding portion, such as an scFv, linked thereto to move independently. A peptide linker can have a length of e.g., at least 4-15 amino acids, or a greater length of e.g., about 20-25 amino acids, which can be readily determined by those skilled in the art according to actual conditions.

Chemical linkers that can be used to form the antibody disclosed herein include, for example, various coupling agents. Examples of the coupling agents include N-succinimidyl-3-(2-pyridyldithio) propionate (SPDP), succinimidyl-4-(N-maleimidomethyl) cyclohexane-1-carboxylate (SMCC), iminothiolane (IT), difunctional derivatives of imidoesters (e.g., dimethyladipimidate HCl), active esters (e.g., disuccinimidyl suberate), aldehydes (e.g., glutaraldehyde), diazide compounds (e.g., bis(p-azidobenzoyl)-hexanediamine), bis-diazo derivatives (e.g., bis-(p-diazoniumbenzoyl)-ethylenediamine), diisocyanates (e.g., toluene 2,6-diisocyanate), and bis-active fluorine compounds (e.g., 1,5-difluoro-2,4-dinitrobenzene). In addition, linkers may be "cleavable linkers" that facilitate release of the polypeptides following delivery to a target site. For example, acid-labile linkers, peptidase-sensitive linkers, photolabile linkers, dimethyl linkers or disulfide-containing linkers can be used (Chari et al., Cancer Research 52 (1992) 127-131; U.S. Pat. No. 5,208,020).

F. Methods and Compositions for Diagnosis and Detection

In one aspect, the invention provides the use of the anti-BCMA antibodies, the fusions or the conjugates disclosed herein in diagnosis and detection. Any of the anti-BCMA antibodies, the fusions or the conjugates provided herein can be used to detect the presence of human BCMA in a biological sample. The term "detection" used herein includes quantitative or qualitative detection. Exemplary detection methods include, but are not limited to, immunohistochemistry, immunocytochemistry, flow cytometry (e.g., FACS), magnetic beads complexed with antibody molecules, ELISA assays, and PCR-techniques (e.g., RT-PCR). In some embodiments, the biological sample comprises body fluid, cells or tissue. In certain embodiments, the biological sample is blood, serum, or other liquid samples of biological origin.

In one embodiment, a method for diagnosis or detection by using the anti-BCMA antibody, fusion or conjugate is provided. In a further aspect, a method for detecting the presence of BCMA in the biological sample is provided. In some embodiments, the method comprises the steps of contacting the biological sample with the anti-BCMA antibody, the fusion or the conjugate described herein under conditions that allow the anti-BCMA antibody, fusion or conjugate to bind to BCMA, and detecting whether a complex is formed between the anti-BCMA antibody, fusion or conjugate and BCMA. The method may be in vitro or in vivo. In one embodiment, the anti-BCMA antibody, the fusion or the conjugate is used to select a subject suitable for treatment with the anti-BCMA antibody, e.g., when BCMA is a biomarker for patient selection. Exemplary disorders that can be diagnosed using the antibodies, the fusions or the conjugates disclosed herein include B-cell related disorders, such as multiple myeloma. In some embodiments, a method for stratifying multiple myeloma (MM) patients by using the antibodies, the fusions or the conjugates disclosed herein is provided, and the method comprises the step of determining whether B cells, preferably malignant B cells, of the patients express BCMA proteins on the surface thereof, wherein the patients will likely respond to and be treated with a BCMA-targeted therapeutic agent (e.g., an anti-BCMA antibody) if the B cells express the BCMA proteins on the surface thereof. In some embodiments, the anti-BCMA antibody can be conjugated with a diagnostic or detectable agent. In some embodiments, a kit for diagnosis or detection is provided, and the kit comprises any of the anti-BCMA antibodies, the fusions or the conjugates disclosed herein.

G. Methods and Compositions for Treatment

In yet another aspect, the invention relates to a method for treating B cell-related disorders, comprising a step of administering to the subject an effective amount of the antibodies or the antigen binding fragments thereof, or the fusions or the conjugates disclosed herein.

The term "individual" or "subject" can be used interchangeably and refers to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In particular, a subject is a human.

The term "treatment" refers to clinical intervention intended to alter the natural course of a disease from which an individual undergoing treatment suffers. Desired therapeutic effects include, but are not limited to, preventing the occurrence or recurrence of diseases, alleviating symptoms, reducing any direct or indirect pathological outcomes of diseases, preventing metastasis, delaying disease progression, improving or alleviating conditions, and improving prognosis.

The B cell-related disorders are disorders associated with aberrant B cell activity, including, but not limited to, B cell malignancies, plasma cell malignancies and autoimmune diseases. Exemplary disorders that can be treated with anti-BCMA antibodies include, for example, multiple myeloma, non-Hodgkin's lymphoma, B-cell proliferation with indeterminate malignant potential, lymphomatoid granulomatosis, post-transplant lymphoproliferative disorder, immunomodulatory disorder, rheumatoid arthritis, myasthenia gravis, idiopathic thrombocytopenic purpura, antiphospholipid syndrome, Chagas disease, Graves' disease, Wegener's granulomatosis, polyarteritis nodosa, Sjogren's syndrome, pemphigus vulgaris, scleroderma, multiple sclerosis, ANCA-associated vasculitis, Goodpasture syndrome, Kawasaki disease, autoimmune hemolytic anemia, acute glomerulonephritis, heavy chain disease, primary or immune cell-associated amyloidosis, monoclonal gammopathy of undetermined significance, systemic lupus erythematosus, and rheumatic arthritis.

As shown in the examples, the inventors constructed the antibodies disclosed herein on the basis of antibody sequences screened from a human antibody library. Thus, advantageously, in some embodiments, the antibodies disclosed herein are fully human antibodies comprising fully humanized VH region and fully humanized VL region amino acid sequences, such as the antibodies shown in Table 1, and the single-chain scFv shown in Table 3 and scFv-Fc antibodies constructed therefrom comprising a human hFc fragment. In some embodiments, the conjugates and the fusions disclosed herein are conjugates and fusions comprising the fully human antibodies, e.g., conjugates and fusions of fully human single-chain scFv antibodies. Thus, in a preferred aspect, the antibodies, the fusions and the conjugates disclosed herein are particularly suitable for treatment of humans. In some preferred embodiments, the antibodies, the fusions and the conjugates disclosed herein are used to treat B-cell related disorders in humans, such as B-cell malignancies, preferably, multiple myeloma (MM) or non-Hodgkin's lymphoma (NHL). In some embodiments, anti-tumor effects of the anti-BCMA antibodies, the fusions and the conjugates disclosed herein include, but are not limited to, for example, a decrease in tumor volume, a decrease in number of tumor cells, a decrease in tumor cell proliferation, or a decrease in tumor cell viability.

In the case of multiple myeloma, a B-cell malignancy of mature plasma cells, clonal plasma cells in bone marrow proliferate abnormally and can invade adjacent bones and sometimes blood. Variants of multiple myeloma include: dominant multiple myeloma, smoldering multiple myeloma, plasma cell leukemia, non-secretory multiple myeloma, IgD multiple myeloma, osteosclerotic myeloma, solitary plasmacytoma of bone, and extramedullary plasmacytoma (see, e.g., Braunwald et al. (eds.), *Harrison's Principles of Internal Medicine*, 15th edition (McGraw-Hill 2001)).

Non-Hodgkin's lymphoma (NHL) presents in different types. For example, non-Hodgkin's lymphoma (NHL) can be classified to be aggressive (fast growing) and indolent (slow growing). Non-Hodgkin's lymphoma (NHL) includes: Burkitt's lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. Lymphoma that occurs after bone marrow or stem cell transplantation is typically B-cell non-Hodgkin's (NHL) lymphoma.

It will be appreciated that the anti-BCMA antibodies, the fusions and the conjugates disclosed herein can be administered in combination with other therapeutic modalities for treatment of the above-mentioned diseases, e.g., tumors. Other therapeutic modalities mentioned above include therapeutic agents, radiation, chemotherapy, transplantation, immunotherapy and the like. In some embodiments, the antibody molecules, the fusions and the conjugates disclosed herein are used in combination with other therapeutic agents. Exemplary therapeutic agents include cytokines, growth factors, steroids, NSAIDs, DMARDs, anti-inflammatory agents, chemotherapeutic agents, radiotherapeutic agents, therapeutic antibodies or other active agents and adjuvants, such as antineoplastic drugs.

H. Compositions and Preparations

The invention also contemplates compositions comprising any one or more of the BCMA-binding antibody molecules, the fusions, the conjugates, the polynucleotides, the vectors or the host cells herein. The compositions include, but are not limited to, pharmaceutical compositions. The pharmaceutical compositions can be administered to cells or animals alone or in combination with one or more other therapeutic modalities.

Pharmaceutical preparations containing the antibodies, the fusions and the conjugates disclosed herein can be prepared, for example, by mixing the antibodies, the fusions and the conjugates with desired purity with one or more optional pharmaceutically acceptable carriers (*Remington's Pharmaceutical Science*, 16th edition, Osol, A. (eds.) (1980)), in forms of a lyophilized preparation or an aqueous solution. The pharmaceutically acceptable carriers are generally non-toxic to a subject at dosages and concentrations employed, and include, but are not limited to, buffers such as phosphate, citrate and other organic acids; antioxidants, including ascorbic acid and methionine; preservatives (such as octadecyl dimethyl benzyl ammonium chloride; hiohex chloride; benzalkonium chloride; benzethonium chloride; phenol, butanol or benzyl alcohol; alkyl esters of p-hydroxybenzoic acid, such as methyl or propyl parabens; catechol; resorcinol; cyclohexanol; 3-pentanol; and m-cresol); low-molecular-weight (less than about 10 residues) polypeptides; proteins, such as serum albumin, gelatin or immunoglobulins; hydrophilic polymers such as poly(vinylpyrrolidone); amino acids such as glycine, glutamine, asparagine, histidine, arginine or lysine; monosaccharides, disaccharides, and other carbohydrates including glucose, mannose, or dextrins; chelating agents, such as EDTA; sugars such as sucrose, mannitol, trehalose or sorbitol; salt-forming counterions such as sodium; metal complexes (e.g., Zn-protein complexes); and/or non-ionic surfactants, such as polyethylene glycol (PEG).

An exemplary lyophilized antibody preparation is described in U.S. Pat. No. 6,267,958. The aqueous antibody preparation includes those described in U.S. Pat. No. 6,171, 586 and WO2006/044908, and the latter preparations include a histidine-acetate buffer.

The preparations herein may also comprise more than one active ingredient required by a treated particular indication, preferably active ingredients having complementarity activities without adversely affecting one another. Such active ingredients are suitably present in combination in an amount effective for an intended purpose.

The following examples are described to assist in understanding the invention. The examples are not intended and should not be interpreted in any way as limiting the protection scope of the invention.

EXAMPLES

Example 1. Screening for Fully Humanized Anti-BCMA Antibodies by Yeast Display

Six synthetic antibody libraries with a total diversity of greater than $1 \times 10^8$ were screened for fully humanized antibodies that specifically bind to BCMA by using yeast display (design and construction of the libraries can be found in WO2009036379, WO2010105256 and WO2012009568). Briefly, the screening procedure was as follows: first, the first round of screening was completed by screening for six synthetic antibody libraries by virtue of biotin-labeled, Fc-fused recombinant human BCMA in combination with magnetic-activated cell sorting (MACS™); the second round of screening was completed by virtue of monkey and murine BCMA fused to Fc in combination with fluorescence-activated cell sorting (FACS™), substantially as described by Chao et al. in *Nature Protocols,* 2006; in the third round of screening, antibodies in the antibody libraries were negatively selected by FACS techniques by using a poly-specificity reagent (PSR) to attenuate non-specific binding of antibodies and subsequent druggability concern, substantially as described by Xu et al. in *Protein Engineering, Design & Selection,* 2013; the fourth round of screening was completed by FACS techniques by using His-tagged human BCMA monomer proteins; the last round of screening was to enrich human, monkey and murine BCMA-specific antibodies by FACS techniques, respectively.

Batch optimization is a routine step for preliminary screening. Briefly, this was done by isolating the heavy chain regions (the diversity at this stage was between $10^3$ and $10^4$) of an antibody population enriched in the preliminary screening and recombining the heavy chain regions with a natural human light chain sequence library in yeast. This process is called light chain batch shuffle (LCBS). Finally, an antibody library possessing a human BCMA binding propensity and a heavy/light chain pairing diversity of $10^7$ to $10^8$ was prepared. One round of magnetic bead screening and four rounds of flow screening as described in the above paragraph were further performed for the antibody library to enrich human, monkey, and murine BCMA specific antibodies. As described above, in this process, fusion proteins of human, monkey and murine BCMA and Fc, and His-tagged human BCMA monomer proteins were used for positive screening, and PSR was used for negative screening.

After the above screening process was completed, the enriched yeast population containing a specific antibody sequence was spread on an agar plate, and a yeast monoclonal colony containing a specific antibody gene could be obtained. A clone was isolated and its variable regions were sequenced by Sanger® sequencing, and approximately 460 antibodies having unique H3:L3 sequences (i.e., antibodies having unique heavy chain CDR3 region and light chain CDR3 region pairs) were identified. Some antibodies were then obtained by yeast expression and protein A affinity chromatography purification.

By further testing the binding ability of the antibodies with various recombinant BCMA proteins, CHO-S™ cell lines stably transfected by BCMA, and BCMA-positive tumor cell line NCI-H929, ten clone strains showing good affinity with NCI-H929 were finally obtained for further analysis. These antibodies also showed certain cross-reactivity with monkey BCMA. The amino acid sequences and corresponding nucleotide sequences of the ten antibody molecules are shown in Table 1 above.

Example 2. Verification for the Affinities of Yeast-Expressed Antibodies with NCI-H929 Cells The binding of above-mentioned ten yeast-expressed antibodies showing good affinity with NCI-H929 and an antibody (ADI-34819, as a negative control) showing no affinity with NCI-H929 to cells was further verified by flow cytometry. The method is specifically as follows:

1. A human NCI-H929 (ATCC, CRL-9068) cell suspension was taken, adjusted to a cell density of $2 \times 10^6$ cells/mL, and added to a 96-well microplate at 100 μL/well. The cell suspension was centrifuged at 400 G for 5 min and the supernatant was removed.
2. The anti-BCMA antibody solution was serially diluted in 3-fold gradient in PBS containing 0.1% bovine serum albumin (BSA) from a concentration of 400 nM for a total of 12 points, 100 μL of the dilution of the antibody was added to each well, and then the plate was incubated at 4° C. for 30 min.
3. The mixture was centrifuged at 400 G for 5 min, and washed twice with PBS, and 100 μL of a dilution of a secondary antibody (a phycoerythrin (PE) labeled goat anti-human IgG antibody, SouthernBiotech, final concentration: 5 μg/mL) in PBS (1% BSA) was added to each well. The plate was incubated at 4° C. for 30 min (in the dark).
4. Then the resulting solution was centrifuged at 400 G for 5 min, and washed twice with PBS, and the cells were resuspended with 100 μL of PBS per well. Flow cytometry was performed on an Accuri C6™ system (BD Bioscience) to detect PE positive signals, and MFI was calculated based on C6™ software. The EC50 values were calculated using GraphPad™ software.

The results are shown in FIG. 1 and Table 4 below. It can be confirmed from the experimental results that the ten antibodies all have a relatively high affinity with NCI-H929 cells at a concentration of 400 nM, and have an affinity with NCI-H929 gradually reduced as the concentration of the antibody decreases gradually.

TABLE 4

| EC50 values for the binding of ten antibodies to NCI-H929 cells | |
|---|---|
| Antibody | EC50 (nM) |
| ADI-34832 | 34.14 |
| ADI-34846 | 136.1 |
| ADI-34848 | 24.83 |
| ADI-34849 | 9.107 |
| ADI-34850 | 12.12 |
| ADI-34854 | 83.24 |
| ADI-34857 | 25.21 |
| ADI-34859 | 85.85 |
| ADI-34860 | 143.5 |
| ADI-34861 | 65.13 |
| ADI-34819 | N/A |

Example 3. Construction of Expression Vectors for scFv-hFc Recombinant Single-Chain Antibodies In order to verify the affinity of a candidate antibody in the form of scFv with a target, expression vectors were constructed for recombinant proteins formed by single-chain variable regions (scFvs) of the above-mentioned ten antibodies and human Fc fragments. Meanwhile, an expression vector for a recombinant single-chain antibody of the ADI-34819 antibody (as a negative control) and an expression vector for a recombinant single-chain antibody based on the huBCMA-10 sequence disclosed in US20170226216 A1 (as a standard control) were also constructed. The amino acid sequences of the constructed scFv-Fc recombinant proteins and the corresponding coding nucleotide sequences thereof are shown in Table 3 above.

Expression vectors expressing the scFv-Fc recombinant proteins listed in Table 3 were constructed.

Figure 2:
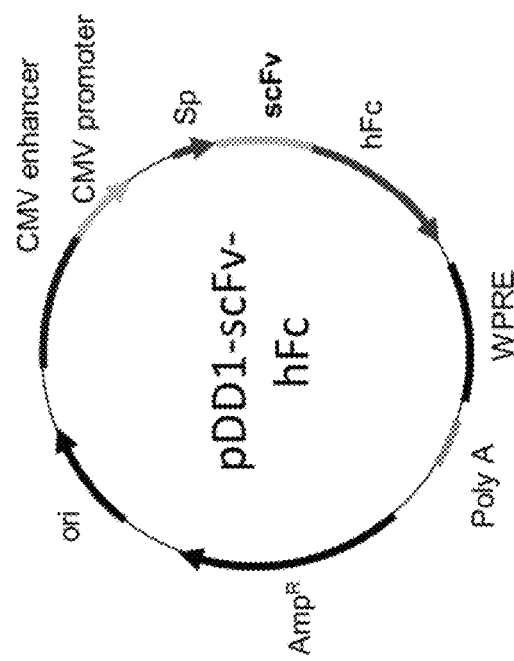
FIG. 2 schematically shows an expression vector cloning strategy of an exemplary recombinant single-chain scFv-hFc antibody of the invention.
Figure 2:
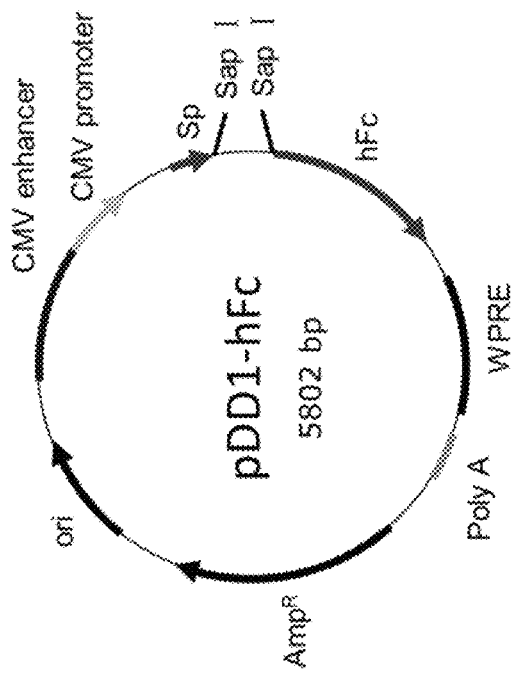

Briefly, a pDD1-hFc vector with a murine κ light chain signal peptide (METDTLLLWVLLLWVPGSTG, SEQ ID NO: 133; coding sequence: ATGGA- GACCGACACCCTGCTGCTCTGGGTCCTGCTGC TGTGGGT GCCCG GATCCACAGGA, SEQ ID NO: 134) and a human IgG1 Fc coding sequence (SEQ ID NO: 132) (a pDD1-hFc vector based on a pTT5™ vector was constructed by inserting the signal peptide and a hFc coding gene) was digested with a restriction enzyme, and the synthesized scFv sequence was cloned, by homologous recombination, between the light chain signal peptide and the hFc coding gene to form fusion expression. A schematic of the vector construction is shown in FIG. 2.

Example 4. Expression of scFv-hFc Recombinant Single-Chain Antibodies

1. HEK293 cells were subcultured according to the desired transfection volume and the cell density was adjusted to $1.2 \times 10^6$ cells/mL the day before transfection.
2. 3 mL of OptiMEM™ medium (Gibco, 31985-070), as a transfection buffer, was thoroughly mixed with 30 µg of a plasmid carrying the encoding gene for a corresponding scFv-hFc recombinant single-chain antibody, and then the mixture was filtered and stood for 5 min.
3. 90 µL of 1 mg/mL polyethyleneimine (PEI) (Polysciences, 23966) was added to the plasmid-OptiMEM™ mixture, and the resulting mixture was well mixed and incubated at room temperature for 15 min. The mixture was poured gently to the cell suspension, and then the cells were cultivated at 36.5° C. and 8% $CO_2$.
4. 20 h later, 0.6 mL of 200 g/L FEED (soya peptone (BD, 211906) in equal proportion to phytone (BD, 210931)), 0.3 mL of 200 g/L dextrose stock solution, and 30 µL of 2.2 M valproic acid sodium salt (VPA) (Sigma, P4543) were added.
5. The cells were continuously cultured until the cell viability was lower than 60%, and then the supernatant was collected, filtered, and purified by affinity chromatography.

Example 5. Purification of scFv-hFc Recombinant Single-Chain Antibodies by the Protein a Method 1. Packings and gravity columns were washed with ultrapure water to remove the packing protection liquid.
2. The gravity columns and the packings were soaked with 0.1 M NaOH for 2 h. 300 µL of protein A affinity chromatography media (Mabselect SuRe™) (GE Healthcare, 17-5438-03) was packed in each gravity column.
3. The cell suspension was centrifuged at 8,000 r/min for 40 min, filtered with a 0.45-µm filter, and stored at 4° C. for further use.
4. The gravity columns and packings were washed with a large amount of ultrapure water to remove alkali liquor.
5. The packings were equilibrated with 10 mL of binding/washing buffer (20 mM Tris+150 mM NaCl (pH 7.2)) prior to purification.
6. The sample, namely, the supernatant to be purified, was loaded on the column.
7. The packings were washed with 5 to 10 mL of binding/washing buffer (20 mM Tris+150 mM NaCl (pH 7.2)) to remove non-specifically binding proteins.
8. The packings were rinsed with 1 mL of elution buffer (100 mM sodium citrate/citric acid buffer, pH 3.5) to collect specifically binding proteins.
9. A neutralization buffer (2 M Tris) was added to the collected solution at a ratio of 85 µL/mL to achieve a pH of 6-7.

Example 6. Fortebio™ Assay for scFv-hFc Recombinant Single-Chain Antibodies

The kinetic constants of the antibody molecules were determined based on the biofilm layer interferometry (BLI) of a fiber optic biosensor.

The basic principle of BLI is: when biomolecules bind to the surface of the sensor, a layer of biofilm is formed and causes an interference phenomenon to the waveform of light transmitted through the sensor, and the interference phenomenon is detected in a phase-shift manner, so that the change in the number of molecules binding to the sensor can be detected; and a kinetic curve is fitted from the changes of real-time response values, and the binding constant ($K_{on}$), the dissociation constant ($K_{dis}$), and the affinity ($K_D$) are calculated.

The Fortebio™ instrument model used in the experiment was Octet® Red96, and a ForteBio affinity assay was performed according to the existing method (Estep, P et al., High throughput solution Based measurement of antibody-antigen affinity and epitope binning. MAbs, 2013.5 (2): p. 270-8). The assay is specifically as follows:
1. Half an hour before the experiment, an appropriate number of AHC sensors were taken according to the number of samples and soaked in the SD buffer (50 mL PBS+0.1% BSA+0.05% Tween-20).
2. SD buffer, scFv-hFc antibodies and human BCMA-His antigens (ACRO BIOSYSTEMS, BCA-H522Y), each of 100 µL, were added to a 96-well half-area black polystyrene microplate respectively.
3. The plates were arranged according to the positions of the samples, the positions of the sensors were selected, and the operation procedures were set as: Baseline, Loading ~1 nm, Baseline, Association, and Dissociation, each running for a time depending on the binding and dissociation rates of the sample, at a rotation speed of 1,000 rpm and a temperature of 30° C.
4. The assay results for the affinities of the ten scFv-hFc recombinant single-chain antibodies with human BCMA-His are shown in Table 5.

TABLE 5

Fortebio ™ assay results for the affinity of scFv-hFc with human BCMA-His

| Molecule ID | KD (M) hBCMA-His | Kon(1/Ms) hBCMA-His | Kdis(1/s) hBCMA-His |
|---|---|---|---|
| ADI-34832 scFv-hFc | 7.07E−08 | 1.86E+05 | 1.31E−02 |
| ADI-34846 scFv-hFc | 1.14E−08 | 1.28E+05 | 1.46E−03 |
| ADI-34848 scFv-hFc | 7.11E−08 | 2.04E+05 | 1.45E−02 |
| ADI-34849 scFv-hFc | 4.91E−08 | 4.19E+05 | 2.06E−02 |
| ADI-34850 scFv-hFc | 3.31E−08 | 2.75E+05 | 9.11E−03 |
| ADI-34854 scFv-hFc | 2.08E−08 | 9.17E+04 | 1.91E−03 |
| ADI-34857 scFv-hFc | 6.44E−09 | 7.29E+05 | 4.69E−03 |
| ADI-34859 scFv-hFc | 3.95E−08 | 2.00E+05 | 7.88E−03 |
| ADI-34860 scFv-hFc | 8.68E−09 | 1.69E+05 | 1.47E−03 |
| ADI-34861 scFv-hFc | 2.27E−08 | 1.46E+05 | 3.31E−03 |
| ADI-34819 scFv-hFc |  | N.B |  |
| Reference scFv-hFc* | 5.97E−09 | 9.28E+05 | 5.54E−03 |

Reference scFv-Fc* is the affinity level of a scFv-hFc recombinant protein constructed from scFv in a BCMA-10 sequence according to US 20170226216 A1 (see example 3, SEQ ID NO: 131).

As can be seen from the data in the above table, the affinities ($K_D$ values) of the ten single-chain antibodies with the monovalent human BCMA (BCMA-His) were comparable to that of the reference single-chain antibody with BCMA-His. Wherein, the affinities of the two single-chain antibodies ADI-34857 and ADI-34860 with BCMA-His were most similar to that of the reference single-chain antibody with BCMA-His.

Example 7. Assay for the Affinities of scFv-hFc Recombinant Single-Chain Antibodies with NCI-H929

After the scFv-hFc fusion antibodies were prepared, the affinities of the scFv-hFc fusion antibodies with NCI-H929 were further verified. The method is specifically as follows:
1. A human NCI-H929 (ATCC, CRL-9068) cell suspension was taken, adjusted to a cell density of $2 \times 10^6$ cells/mL, and added to a 96-well microplate at 100 μL/well. The cell suspension was centrifuged at 400 G for 5 min and the supernatant was removed.
2. The scFv-hFc antibody solution was serially diluted in 3-fold gradient in PBS containing 0.1% bovine serum albumin (BSA) from a concentration of 400 nM for a total of 12 points, 100 μL of the dilution of the antibody was added to each well, and then the plate was incubated at 4° C. for 30 min.
3. The mixture was centrifuged at 400 G for 5 min, and washed twice with PBS, and 100 μL of a dilution of a secondary antibody (a phycoerythrin (PE) labeled goat anti-human IgG antibody, SouthernBiotech, final concentration: 5 μg/mL) in PBS (1% BSA) was added to each well. The plate was incubated at 4° C. for 30 min (in the dark).
4. Then the resulting solution was centrifuged at 400 G for 5 min, and washed twice with PBS, and the cells were resuspended with 100 μL of PBS per well. Flow cytometry was performed on an Accuri™ C6 system (BD Bioscience) to detect PE positive signals, and MFI was calculated based on C6™ software. The EC50 values were calculated using GraphPad™ software.

Figure 3:
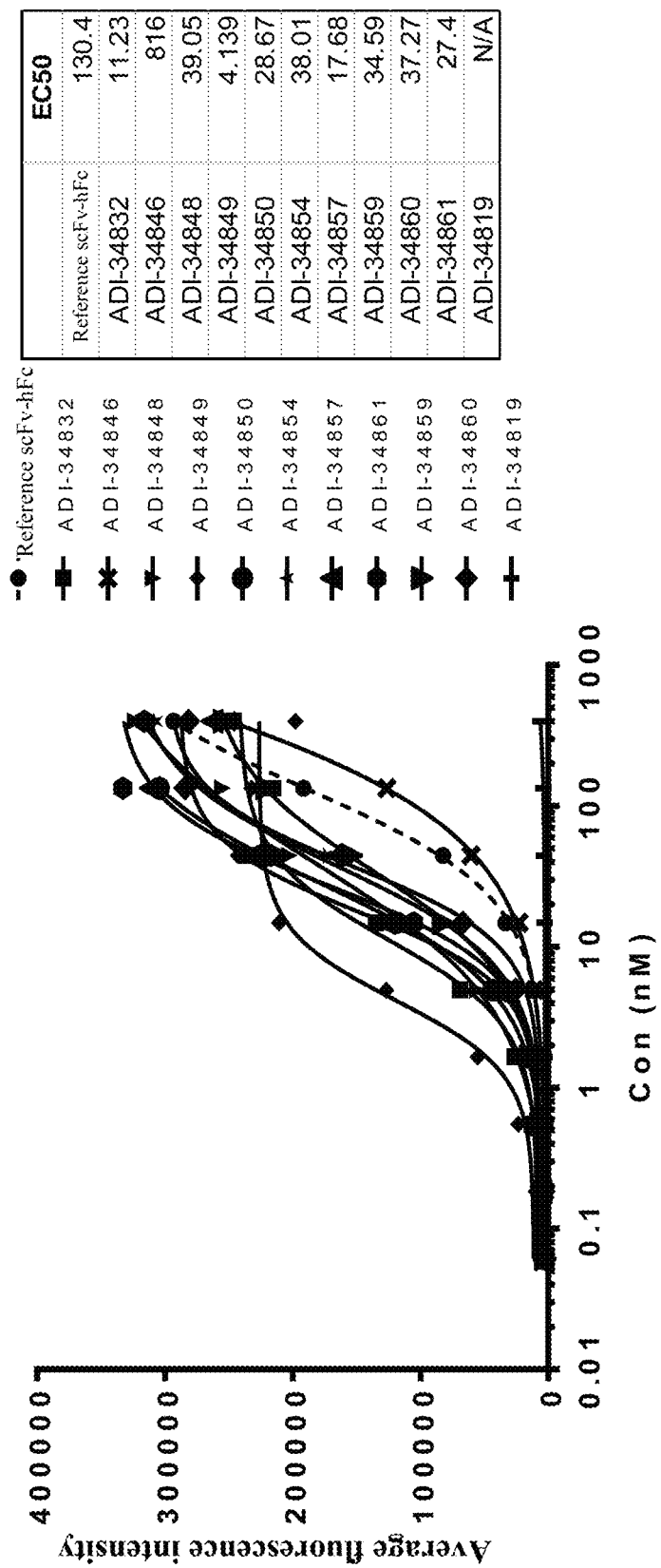
FIG. 3 shows the affinity of exemplary recombinant single-chain scFv-hFc antibodies disclosed herein of the invention with NCI-H929 cells as determined by flow cytometry.

The results are shown in FIG. 3 and Table 6 below. As can be seen from the results in the figure, the affinities (EC50 values) of the single-chain antibodies with NCI-H929 cells are all superior to that of the reference single-chain antibody with NCI-H929 cells, except for the single-chain antibody ADI-34846.

TABLE 6

| Affinities (EC50 values) of the single-chain antibodies with NCI-H929 cells | |
|---|---|
| Antibody | EC50 (nM) |
| Reference scFv-hc | 130.4 |
| ADI-34832 scFv-hc | 11.23 |
| ADI-34846 scFv-hc | 816.0 |
| ADI-34848 scFv-hc | 39.05 |
| ADI-34849 scFv-hc | 4.139 |
| ADI-34850 scFv-hc | 28.67 |
| ADI-34854 scFv-hc | 38.01 |
| ADI-34857 scFv-hc | 17.68 |
| ADI-34859 scFv-hc | 34.59 |
| ADI-34860 scFv-hc | 37.27 |
| ADI-34861 scFv-hc | 27.40 |
| ADI-34819 scFv-hc | N/A |

The invention claimed is:

1. An isolated antibody or an antigen-binding fragment thereof specifically binding to B-cell maturation antigen (BCMA), wherein the antibody or antigen-binding fragment thereof comprises:
   (i) three heavy chain complementarity determining regions HCDR1, HCDR2 and HCDR3 sequences of a heavy chain variable region set forth in SEQ ID NO: 4 or 5, and three light chain complementarity determining regions LCDR1, LCDR2 and LCDR3 sequences of a light chain variable region set forth in SEQ ID NO: 31, 41 or 42,
   (ii) HCDR1, HCDR2 and HCDR3 sequences of a heavy chain variable region set forth in SEQ ID NO: 10, and LCDR1, LCDR2 and LCDR3 sequences of a light chain variable region set forth in SEQ ID NO: 46,
   (iii) HCDR1, HCDR2 and HCDR3 sequences of a heavy chain variable region set forth in SEQ ID NO: 16 or 17, and LCDR1, LCDR2 and LCDR3 sequences of a light chain variable region set forth in SEQ ID NO: 50 or 58,
   (iv) HCDR1, HCDR2 and HCDR3 sequences of a heavy chain variable region set forth in SEQ ID NO: 23, and LCDR1, LCDR2 and LCDR3 sequences of a light chain variable region set forth in SEQ ID NO: 64, or
   (v) HCDR1, HCDR2 and HCDR3 sequences of a heavy chain variable region set forth in SEQ ID NO: 27, and LCDR1, LCDR2 and LCDR3 sequences of a light chain variable region set forth in SEQ ID NO: 59, 71 or 72.

2. The isolated antibody or antigen-binding fragment thereof of claim 1 comprising three heavy chain complementarity determining regions (HCDRs) and three light chain complementarity determining regions (LCDRs) of the following:
   (a) an HCDR1 comprising an amino acid sequence set forth in SEQ ID NO: 1, an HCDR2 comprising an amino acid sequence set forth in SEQ ID NO: 2, an HCDR3 comprising an amino acid sequence set forth in SEQ ID NO: 3, an LCDR1 comprising an amino acid sequence set forth in SEQ ID NO: 28, an LCDR2 comprising an amino acid sequence set forth in SEQ ID NO: 29, and an LCDR3 comprising an amino acid sequence set forth in SEQ ID NO: 30;
   (b) an HCDR1 comprising an amino acid sequence set forth in SEQ ID NO: 1, an HCDR2 comprising an amino acid sequence set forth in SEQ ID NO: 2, an HCDR3 comprising an amino acid sequence set forth in SEQ ID NO: 3, an LCDR1 comprising an amino acid sequence set forth in SEQ ID NO: 32, an LCDR2 comprising an amino acid sequence set forth in SEQ ID NO: 35, and an LCDR3 comprising an amino acid sequence set forth in SEQ ID NO: 38;
   (c) an HCDR1 comprising an amino acid sequence set forth in SEQ ID NO: 1, an HCDR2 comprising an amino acid sequence set forth in SEQ ID NO: 2, an HCDR3 comprising an amino acid sequence set forth in SEQ ID NO: 3, an LCDR1 comprising an amino acid sequence set forth in SEQ ID NO: 33, an LCDR2 comprising an amino acid sequence set forth in SEQ ID NO: 36, and an LCDR3 comprising an amino acid sequence set forth in SEQ ID NO: 39;
   (d) an HCDR1 comprising an amino acid sequence set forth in SEQ ID NO: 7, an HCDR2 comprising an amino acid sequence set forth in SEQ ID NO: 8, an HCDR3 comprising an amino acid sequence set forth in SEQ ID NO: 9, an LCDR1 comprising an amino acid sequence set forth in SEQ ID NO: 32, an LCDR2 comprising an amino acid sequence set forth in SEQ ID NO: 44, and an LCDR3 comprising an amino acid sequence set forth in SEQ ID NO: 45;
   (e) an HCDR1 comprising an amino acid sequence set forth in SEQ ID NO: 11, an HCDR2 comprising an amino acid sequence set forth in SEQ ID NO: 12, an HCDR3 comprising an amino acid sequence set forth in SEQ ID NO: 13, an LCDR1 comprising an amino acid sequence set forth in SEQ ID NO: 47, an LCDR2 comprising an amino acid sequence set forth in SEQ ID NO: 48, and an LCDR3 comprising an amino acid sequence set forth in SEQ ID NO: 49;
   (f) an HCDR1 comprising an amino acid sequence set forth in SEQ ID NO: 11, an HCDR2 comprising an amino acid sequence set forth in SEQ ID NO: 12, an HCDR3 comprising an amino acid sequence set forth in SEQ ID NO: 14, an LCDR1 comprising an amino acid sequence set forth in SEQ ID NO: 51, an LCDR2 comprising an amino acid sequence set forth in SEQ ID NO: 54, and an LCDR3 comprising an amino acid sequence set forth in SEQ ID NO: 55;
(g) an HCDR1 comprising an amino acid sequence set forth in SEQ ID NO: 20, an HCDR2 comprising an amino acid sequence set forth in SEQ ID NO: 21, an HCDR3 comprising an amino acid sequence set forth in SEQ ID NO: 22, an LCDR1 comprising an amino acid sequence set forth in SEQ ID NO: 61, an LCDR2 comprising an amino acid sequence set forth in SEQ ID NO: 62, and an LCDR3 comprising an amino acid sequence set forth in SEQ ID NO: 63;
(h) an HCDR1 comprising an amino acid sequence set forth in SEQ ID NO: 24, an HCDR2 comprising an amino acid sequence set forth in SEQ ID NO: 25, an HCDR3 comprising an amino acid sequence set forth in SEQ ID NO: 26, an LCDR1 comprising an amino acid sequence set forth in SEQ ID NO: 52, an LCDR2 comprising an amino acid sequence set forth in SEQ ID NO: 62, and an LCDR3 comprising an amino acid sequence set forth in SEQ ID NO: 56;
(i) an HCDR1 comprising an amino acid sequence set forth in SEQ ID NO: 24, an HCDR2 comprising an amino acid sequence set forth in SEQ ID NO: 25, an HCDR3 comprising an amino acid sequence set forth in SEQ ID NO: 26, an LCDR1 comprising an amino acid sequence set forth in SEQ ID NO: 65, an LCDR2 comprising an amino acid sequence set forth in SEQ ID NO: 62, and an LCDR3 comprising an amino acid sequence set forth in SEQ ID NO: 68; or
(j) an HCDR1 comprising an amino acid sequence set forth in SEQ ID NO: 24, an HCDR2 comprising an amino acid sequence set forth in SEQ ID NO: 25, an HCDR3 comprising an amino acid sequence set forth in SEQ ID NO: 26, an LCDR1 comprising an amino acid sequence set forth in SEQ ID NO: 66, an LCDR2 comprising an amino acid sequence set forth in SEQ ID NO: 62, and an LCDR3 comprising an amino acid sequence set forth in SEQ ID NO: 69.

3. The antibody or the antigen-binding fragment thereof of claim 2, wherein the antibody or antigen-binding fragment thereof comprises a heavy chain variable region VH selected from:
(a) a VH comprising an amino acid sequence selected from SEQ ID NOs: 4 and 5, or an amino acid sequence having at least 80%, 85%, 90%, 92%, 95%, 97%, 98%, 99% or higher identity thereto, or an amino acid sequence comprising no more than 10 or no more than 5 amino acid alterations compared thereto;
(b) a VH comprising an amino acid sequence of SEQ ID NO: 10, or an amino acid sequence having at least 80%, 85%, 90%, 92%, 95%, 97%, 98%, 99% or higher identity thereto, or an amino acid sequence comprising no more than 10 or no more than 5 amino acid alterations compared thereto;
(c) a VH comprising an amino acid sequence selected from SEQ ID NOs: 16 and 17, or an amino acid sequence having at least 80%, 85%, 90%, 92%, 95%, 97%, 98%, 99% or higher identity thereto, or an amino acid sequence comprising no more than 10 or no more than 5 amino acid alterations compared thereto;
(d) a VH comprising an amino acid sequence of SEQ ID NO: 23, or an amino acid sequence having at least 80%, 85%, 90%, 92%, 95%, 97%, 98%, 99% or higher identity thereto, or an amino acid sequence comprising no more than 10 or no more than 5 amino acid alterations compared thereto; and
(e) a VH comprising an amino acid sequence of SEQ ID NO: 27, or an amino acid sequence having at least 80%, 85%, 90%, 92%, 95%, 97%, 98%, 99% or higher identity thereto, or an amino acid sequence comprising no more than 10 or no more than 5 amino acid alterations compared thereto,
and/or wherein the antibody or antigen-binding fragment thereof comprises a light chain variable region VL selected from:
(a) a VL comprising an amino acid sequence selected from SEQ ID NOs: 31, 41 and 42, or an amino acid sequence having at least 90%, 92%, 95%, 97%, 98%, 99% or higher identity thereto, or an amino acid sequence comprising no more than 10 or no more than 5 amino acid alterations compared thereto;
(b) a VL comprising an amino acid sequence of SEQ ID NO: 46, or an amino acid sequence having at least 90%, 92%, 95%, 97%, 98%, 99% or higher identity thereto, or an amino acid sequence comprising no more than 10 or no more than 5 amino acid alterations compared thereto;
(c) a VL comprising an amino acid sequence selected from SEQ ID NOs: 50 and 58, or an amino acid sequence having at least 80%, 85%, 90%, 92%, 95%, 97%, 98%, 99% or higher identity thereto, or an amino acid sequence comprising no more than 10 or no more than 5 amino acid alterations compared thereto;
(d) a VL comprising an amino acid sequence of SEQ ID NO: 64, or an amino acid sequence having at least 80%, 85%, 90%, 92%, 95%, 97%, 98%, 99% or higher identity thereto, or an amino acid sequence comprising no more than 10 or no more than 5 amino acid alterations compared thereto; and
(e) a VL comprising an amino acid sequence selected from SEQ ID NOs: 59, 71 and 72, or an amino acid sequence having at least 80%, 85%, 90%, 92%, 95%, 97%, 98%, 99% or higher identity thereto, or an amino acid sequence comprising no more than 10 or no more than 5 amino acid alterations compared thereto.

4. The isolated antibody or the antigen-binding fragment thereof of claim 2, wherein the antibody or antigen-binding fragment thereof comprises a heavy chain variable region VH and a light chain variable region VL, and the VH and the VL are selected from:
(a) a VH comprising an amino acid sequence of SEQ ID NO: 4, and a VL comprising an amino acid sequence of SEQ ID NO: 31;
(b) a VH comprising an amino acid sequence of SEQ ID NO: 5, and a VL comprising an amino acid sequence of SEQ ID NO: 41;
(c) a VH comprising an amino acid sequence of SEQ ID NO: 5, and a VL comprising an amino acid sequence of SEQ ID NO: 42;
(d) a VH comprising an amino acid sequence of SEQ ID NO: 10, and a VL comprising an amino acid sequence of SEQ ID NO: 46;
(e) a VH comprising an amino acid sequence of SEQ ID NO: 16, and a VL comprising an amino acid sequence of SEQ ID NO: 50;
(f) a VH comprising an amino acid sequence of SEQ ID NO: 17, and a VL comprising an amino acid sequence of SEQ ID NO: 58;
(g) a VH comprising an amino acid sequence of SEQ ID NO: 23, and a VL comprising an amino acid sequence of SEQ ID NO: 64;

(h) a VH comprising an amino acid sequence of SEQ ID NO: 27, and a VL comprising an amino acid sequence of SEQ ID NO: 59;
(i) a VH comprising an amino acid sequence of SEQ ID NO: 27, and a VL comprising an amino acid sequence of SEQ ID NO: 71; and
(j) a VH comprising an amino acid sequence of SEQ ID NO: 27, and a VL comprising an amino acid sequence of SEQ ID NO: 72.

5. The antibody or the antigen-binding fragment thereof of claim 1, wherein the antibody or antigen-binding fragment thereof has one or more of the following properties:
(i) binding to human BCMA with a $K_D$ of less than 100 nM, less than 50 nM, or less than 10 nM;
(ii) binding to human BCMA with an $EC_{50}$ of less than 100 nM, less than 50 nM, less than 20 nM, or less than 10 or 5 nM;
(iii) binding to human BCMA with a dissociation rate constant ($K_d$) of less than $3\times10^{-2}$, $1.5\times10^{-2}$, $5\times10^{-3}$, or $3\times10^{-3}$ $s^{-1}$;
(iv) specifically binding to an epitope on an extracellular domain (ECD) of human BCMA; and
(v) blocking and inhibiting growth of cells expressing human BCMA, and/or killing the cells.

6. The antibody or the antigen-binding fragment thereof of claim 1, wherein the antibody or antigen-binding fragment thereof is fully humanized.

7. The antibody or the antigen-binding fragment thereof of claim 2, wherein the antibody is a single-chain antibody.

8. The antibody of claim 7, wherein the antibody is a single-chain scFv antibody, wherein the single-chain scFv antibody comprises VL domain-linker-VH domain or VH domain-linker-VL domain from N terminus to C terminus, optionally the linker comprising an amino acid sequence of SEQ ID NO: 93.

9. The antibody of claim 8, wherein the single-chain scFv antibody comprises an amino acid sequence selected from SEQ ID NOs: 99, 102, 105, 108, 111, 114, 117, 120, 123, and 126, or an amino acid sequence having at least 90%, 92%, 95%, 97%, 98%, 99% or higher identity thereto, or an amino acid sequence comprising at least one, two, or three, but no more than 30, 20 or 10 amino acid alterations compared thereto.

10. The antibody of claim 8, wherein the single-chain scFv antibody is connected to a Fc region, optionally by a hinge region, further optionally the hinge region is a CD8 hinge region that comprises an amino acid sequence set forth in SEQ ID NO: 95 or an amino acid sequence having at least one, two or three, but no more than 5 amino acid alterations compared to the amino acid sequence of SEQ ID NO: 95.

11. The antibody of claim 10, wherein the Fc region is a human IgG1 or IgG4 Fc region, optionally the Fc region is low- or non-fucosylated.

12. The antibody of claim 2, wherein the antibody comprises an amino acid sequence selected from SEQ ID NOs: 101, 104, 107, 110, 113, 116, 119, 122, 125, and 128, or an amino acid sequence comprising at least one, two, or three, but no more than 20, 10, or 5 amino acid alterations compared thereto, or an amino acid sequence having at least 80%, 85%, 90%, 92%, 95%, 97%, 98%, 99% or higher identity thereto.

13. An isolated nucleic acid encoding the isolated antibody or the antigen-binding fragment thereof of claim 1.

14. A vector comprising the nucleic acid of claim 13.

15. A host cell comprising the vector of claim 14.

16. A method for preparing the isolated antibody or the antigen-binding fragment thereof of claim 1, comprising cultivating a host cell comprising a nucleic acid encoding the antibody or the antigen-binding fragment thereof, under a condition suitable for expressing the antibody or the antigen-binding fragment thereof.

17. A conjugate or a fusion comprising the antibody of claim 1.

18. A pharmaceutical composition, comprising the isolated antibody or the antigen-binding fragment thereof of claim 1, and optionally a pharmaceutically acceptable carrier.

19. A method for detecting BCMA in a sample, comprising
(a) contacting the sample with the isolated antibody or the antigen-binding fragment thereof of claim 1; and
(b) detecting the formation of a complex of the antibody or the antigen-binding fragment thereof with BCMA.

* * * * *